US012246113B2

(12) United States Patent
Padilla et al.

(10) Patent No.: US 12,246,113 B2
(45) Date of Patent: Mar. 11, 2025

(54) FABRICATION OF POROUS SCAFFOLDS USING ADDITIVE MANUFACTURING WITH POTENTIAL APPLICATIONS IN BONE TISSUE ENGINEERING

(71) Applicant: Ohio State Innovation Foundation, Columbus, OH (US)

(72) Inventors: Hernan Lara Padilla, Columbus, OH (US); David Dean, Columbus, OH (US); Ciro Rodriguez, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 793 days.

(21) Appl. No.: 17/266,807

(22) PCT Filed: Aug. 7, 2019

(86) PCT No.: PCT/US2019/045588
§ 371 (c)(1),
(2) Date: Feb. 8, 2021

(87) PCT Pub. No.: WO2020/033607
PCT Pub. Date: Feb. 13, 2020

(65) Prior Publication Data
US 2021/0316367 A1 Oct. 14, 2021

Related U.S. Application Data

(60) Provisional application No. 62/715,596, filed on Aug. 7, 2018.

(51) Int. Cl.
*B33Y 10/00* (2015.01)
*A61L 27/16* (2006.01)
(Continued)

(52) U.S. Cl.
CPC ............... *A61L 27/56* (2013.01); *A61L 27/16* (2013.01); *B22F 10/12* (2021.01); *B22F 10/14* (2021.01); *B22F 10/18* (2021.01); *B22F 10/25* (2021.01); *B22F 10/28* (2021.01); *B22F 10/36* (2021.01); *B22F 10/38* (2021.01); *B22F 10/85* (2021.01); *B22F 12/90* (2021.01); *B29C 64/165* (2017.08); *B29C 64/393* (2017.08); *B33Y 10/00* (2014.12);
(Continued)

(58) Field of Classification Search
None
See application file for complete search history.

(56) References Cited

U.S. PATENT DOCUMENTS 5,182,056 A    1/1993  Spence et al.
6,048,954 A    4/2000  Barlow et al.
(Continued)

OTHER PUBLICATIONS

Communication pursuant to Article 94(3) EPC dated Jul. 18, 2023, for European Application No. 19846543.7. 7 pages.
(Continued)

*Primary Examiner* — Yung-Sheng M Tsui
(74) *Attorney, Agent, or Firm* — Meunier Carlin & Curfman LLC

(57) ABSTRACT

The present disclosure describes additive manufacturing methods, in particular methods for optimizing the manufacture of objects by three-dimensional printing processes. Also provided are bioreactors as well as methods of using thereof.

18 Claims, 19 Drawing Sheets

(51) Int. Cl.
| | |
|---|---|
| *A61L 27/56* | (2006.01) |
| *B22F 10/12* | (2021.01) |
| *B22F 10/14* | (2021.01) |
| *B22F 10/18* | (2021.01) |
| *B22F 10/25* | (2021.01) |
| *B22F 10/28* | (2021.01) |
| *B22F 10/36* | (2021.01) |
| *B22F 10/38* | (2021.01) |
| *B22F 10/85* | (2021.01) |
| *B22F 12/90* | (2021.01) |
| *B29C 64/165* | (2017.01) |
| *B29C 64/393* | (2017.01) |
| *B33Y 50/02* | (2015.01) |
| *B33Y 80/00* | (2015.01) |
| *C12M 1/00* | (2006.01) |
| *C12M 3/00* | (2006.01) |

(52) U.S. Cl.
CPC ............... *B33Y 50/02* (2014.12); *B33Y 80/00* (2014.12); *C12M 23/44* (2013.01); *C12M 29/10* (2013.01); *A61L 2430/02* (2013.01)

(56) References Cited

U.S. PATENT DOCUMENTS

| | | | |
|---|---|---|---|
| 2009/0256284 | A1 | 10/2009 | McGuire et al. |
| 2015/0314039 | A1 | 11/2015 | Dean et al. |
| 2017/0057178 | A1* | 3/2017 | FrantzDale ............ B33Y 50/02 |
| 2017/0297097 | A1 | 10/2017 | Gibson et al. |

OTHER PUBLICATIONS

Partial Supplementary European Search Report issued for Application No. 19846543.7, dated Feb. 24, 2022.
International Preliminary Report on Patentability issued for Application No. PCT/US2019/045588, dated Feb. 18, 2021.
Abhay, Sanan, and Stephen J. Haines. "Repairing Holes in the Head: A History of Cranioplasty." Neurosurgery, Mar. 1997, 588-603. https://doi.org/10.1097/0006123-199703000-00033.
Banic, Andrej, and Ralph Hertel. 1993. "Double Vascularized Fibulas for Reconstruction of Large Tibial Defects." Journal of Reconstructive Microsurgery 9 (06): 421-28. https://doi.org/10.1055/s-2007-1006751.
Basu, Bikramjit. 2017. "Natural Bone and Tooth: Structure and Properties." In Biomaterials for Musculoskeletal Regeneration, 45-85. Indian Institute of Metals Series. Springer, Singapore. https://doi.org/10.1007/978-981-10-3059-8.
Béchet, E., J.-C. Cuilliere, and F. Trochu. 2002. "Generation of a Finite Element MESH from Stereolithography (STL) Files." Computer-Aided Design 34 (1): 1-17. https://doi.org/10.1016/S0010-4485(00)00146-9.
Van Bochove, Bas, Gerjon Hannink, Pieter Buma, and Dirk W. Grijpma. 2016. "Preparation of Designed Poly(Trimethylene Carbonate) Meniscus Implants by Stereolithography: Challenges in Stereolithography." Macromolecular Bioscience 16 (12): 1853-63. https://doi.org/10.1002/mabi.201600290.
Burr, David B., A. G. Robling, and C. H. Turner. 2002. "Effects of Biomechanical Stress on Bones in Animals." Bone 30 (5): 781-86.
Choi, Jae-Won, Ryan Wicker, Seok-Hee Lee, Kyung-Hyun Choi, Chang-Sik Ha, and Ildoo Chung. 2009. "Fabrication of 3D Biocompatible/Biodegradable Micro-Scaffolds Using Dynamic Mask Projection Microstereolithography." Journal of Materials Processing Technology 209 (15): 5494-5503. https://doi.org/10.1016/j.jmatprotec.2009.05.004.
Cignoni, Paolo, Marco Callieri, Massimiliano Corsini, Matteo Dellepiane, Fabio Ganovelli, and Guido Ranzuglia. 2008. MeshLab: An Open-Source Mesh Processing Tool. The Eurographics Association. http://dx.doi.org/10.2312/LocalChapterEvents/ItalChap/ItalianChapConf2008/129-136.
Dean, David, Jonathan Wallace, Ali Siblani, Martha O. Wang, Kyobum Kim, Antonios G. Mikos, and John P. Fisher. 2012. "Continuous Digital Light Processing (CDLP): Highly Accurate Additive Manufacturing of Tissue Engineered Bone Scaffolds." Virtual and Physical Prototyping 7 (1): 13-24. https://doi.org/10.1080/17452759.2012.673152.
DeCoster, Thomas A., Rick J. Gehlert, Elizabeth A. Mikola, and Miguel A. Pirela-Cruz. 2004. "Management of Posttraumatic Segmental Bone Defects." The Journal of the American Academy of Orthopaedic Surgeons 12 (1): 28-38.
Gardel, Leandro S., Luís A. Serra, Rui L. Reis, and Manuela E. Gomes. 2014. "Use of Perfusion Bioreactors and Large Animal Models for Long Bone Tissue Engineering." Tissue Engineering. Part B, Reviews 20 (2): 126-46. https://doi.org/10.1089/ten.TEB.2013.0010.
Geuzaine, Christophe, and Jean-François Remacle. 2009. "Gmsh: A 3-D Finite Element Mesh Generator with Built-in Pre- and Post-Processing Facilities." International Journal for Numerical Methods in Engineering 79 (11): 1309-31. https://doi.org/10.1002/nme.2579.
Giannitelli, S. M., D. Accoto, M. Trombetta, and A. Rainer. 2014. "Current Trends in the Design of Scaffolds for Computer-Aided Tissue Engineering." Acta Biomaterialia 10 (2): 580-94. https://doi.org/10.1016/j.actbio.2013.10.024.
Giannitelli, S. M., P. Mozetic, M. Trombetta, and A. Rainer. 2015a. "Combined Additive Manufacturing Approaches in Tissue Engineering." Acta Biomaterialia 24 (Sep.): 1-11. https://doi.org/10.1016/j.actbio.2015.06.032.
Giannoudis, Peter V., Haralambos Dinopoulos, and Eleftherios Tsiridis. 2005. "Bone Substitutes: An Update." Injury 36 Suppl 3 (Nov.): S20-27. https://doi.org/10.1016/j.injury.2005.07.029.
Griffin, Kaitlyn S., Korbin M. Davis, Todd O. McKinley, Jeffrey O. Anglen, Tien-Min G. Chu, Joel D. Boerckel, and Melissa A. Kacena. 2015. "Evolution of Bone Grafting: Bone Grafts and Tissue Engineering Strategies for Vascularized Bone Regeneration." Clinical Reviews in Bone and Mineral Metabolism 13 (4): 232-44. https://doi.org/10.1007/s12018-015-9194-9.
Haj, A. J. El, and S. H. Cartmell. 2010. "Bioreactors for Bone Tissue Engineering." Proceedings of the Institution of Mechanical Engineers, Part H: Journal of Engineering in Medicine 224 (12): 1523-32. https://doi.org/10.1243/09544119JEIM802.
Hollister, Scott J. 2005a. "Porous Scaffold Design for Tissue Engineering." Nature Materials 4 (7): 518-24. https://doi.org/10.1038/nmat1421.
Holzapfel, Boris Michael, Johannes Christian Reichert, Jan-Thorsten Schantz, Uwe Gbureck, Lars Rackwitz, Ulrich Nöth, Franz Jakob, Maximilian Rudert, Jürgen Groll, and Dietmar Werner Hutmacher. 2013a. "How Smart Do Biomaterials Need to Be? A Translational Science and Clinical Point of View." Advanced Drug Delivery Reviews, Bionics—Biologically inspired smart materials, 65 (4): 581-603. https://doi.org/10.1016/j.addr.2012.07.009.
Huang, You-Min, and Cho-Pei Jiang. 2005. "On-Line Force Monitoring of Platform Ascending Rapid Prototyping System." Journal of Materials Processing Technology 159 (2): 257-64. https://doi.org/10.1016/j.jmatprotec.2004.05.015.
Hutmacher, D. W. 2000. "Scaffolds in Tissue Engineering Bone and Cartilage." Biomaterials 21 (24): 2529-43.
Ibrahim, A. 2018. "13—3D Bioprinting Bone." In 3D Bioprinting for Reconstructive Surgery, edited by Daniel J. Thomas, Zita M. Jessop, and Iain S. Whitaker, 245-75. Woodhead Publishing. https://doi.org/10.1016/B978-0-08-101103-4.00015-6.
"Introduction to Reliability Engineering." 2011. In Practical Reliability Engineering, by Patrick D. T. O'Connor and Andre Kleyner, 1-18. Chichester, UK: John Wiley & Sons, Ltd. https://doi.org/10.1002/9781119961260.ch1.
Ivanovski, S., C. Vaquette, S. Gronthos, D. W. Hutmacher, and P. M. Bartold. 2014. "Multiphasic Scaffolds for Periodontal Tissue Engineering." Journal of Dental Research 93 (12): 1212-21. https://doi.org/10.1177/0022034514544301.
Jariwala, Shailly H., Gregory S. Lewis, Zachary J. Bushman, James H. Adair, and Henry J. Donahue. 2015. "3D Printing of Personalized Artificial Bone Scaffolds." 3d Printing and Additive Manufacturing 2 (2): 56-64. https://doi.org/10.1089/3dp.2015.0001.

(56) References Cited

OTHER PUBLICATIONS

Karageorgiou, Vassilis, and David Kaplan. 2005. "Porosity of 3D Biomaterial Scaffolds and Osteogenesis." Biomaterials 26 (27): 5474-91. https://doi.org/10.1016/j.biomaterials.2005.02.002.

Karande, Tejas S., Joo L. Ong, and C. Mauli Agrawal. 2004. "Diffusion in Musculoskeletal Tissue Engineering Scaffolds: Design Issues Related to Porosity, Permeability, Architecture, and Nutrient Mixing." Annals of Biomedical Engineering 32 (12): 1728-43.

Kinaci, Ahmet, Valentin Neuhaus, and David C. Ring. 2014. "Trends in Bone Graft Use in the United States." Orthopedics 37 (9): e783-788. https://doi.org/10.3928/01477447-20140825-54.

Kovalenko, Jaroslav, Sylvain Verron, Maryna Garan, Jiří Šafka, and Michal Moučka. 2017. "Implementation of Non-Destructive Evaluation and Process Monitoring in DLP-Based Additive Manufacturing." Open Engineering 7 (1): 100-105. https://doi.org/10.1515/eng-2017-0016.

Langer, R., and J. P. Vacanti. 1993. "Tissue Engineering." Science (New York, N.Y.) 260 (5110): 920-26.

Laurencin, Cato, Yusuf Khan, and Saadiq F. El-Amin. 2006. "Bone Graft Substitutes." Expert Review of Medical Devices 3 (1): 49-57. https://doi.org/10.1586/17434440.3.1.49.

Lian, Qin, Fei Yang, Hua Xin, and Dichen Li. 2017. "Oxygen-Controlled Bottom-up Mask-Projection Stereolithography for Ceramic 3D Printing." Ceramics International 43 (17): 14956-61. https://doi.org/10.1016/j.ceramint.2017.08.014.

Melchels, Ferry P. W., Jan Feijen, and Dirk W. Grijpma. 2009. "A Poly(D,L-Lactide) Resin for the Preparation of Tissue Engineering Scaffolds by Stereolithography." Biomaterials 30 (23-24): 3801-9. https://doi.org/10.1016/j.biomaterials.2009.03.055.

Meyer, Ulrich. 2009. "The History of Tissue Engineering and Regenerative Medicine in Perspective." In Fundamentals of Tissue Engineering and Regenerative Medicine, 5-12. Springer, Berlin, Heidelberg. https://doi.org/10.1007/978-3-540-77755-7_1.

Meyer, Ulrich, Hans Peter Wiesmann, Jörg Handschel, and Norbert R. Kübler. 2009. "Bone Tissue Engineering." In Fundamentals of Tissue Engineering and Regenerative Medicine, 211-32. Springer, Berlin, Heidelberg. https://doi.org/10.1007/978-3-540- 77755-7_17.

Mott, Eric J., Mallory Busso, Xinyi Luo, Courtney Dolder, Martha O. Wang, John P. Fisher, and David Dean. 2016. "Digital Micromirror Device (DMD)-Based 3D Printing of Poly(Propylene Fumarate) Scaffolds." Materials Science & Engineering. C, Materials for Biological Applications 61 (Apr.): 301-11. https://doi.org/10.1016/j.msec.2015.11.071.

Nerem, Robert M., and Stacey C. Schutte. 2014. "Chapter 2—The Challenge of Imitating Nature." In Principles of Tissue Engineering (Fourth Edition), 9-24. Boston: Academic Press. https://doi.org/10.1016/B978-0-12-398358-9.00002-1.

Ng, Vincent Y. 2012. "Risk of Disease Transmission with Bone Allograft." Orthopedics 35 (8): 679-81. https://doi.org/10.3928/01477447-20120725-04.

Pan, Yayue, Haiyang He, Jie Xu, and Alan Feinerman. 2017. "Study of Separation Force in Constrained Surface Projection Stereolithography." Rapid Prototyping Journal 23 (2): 353-61. https://doi.org/10.1108/RPJ-12-2015-0188.

Pangborn, Christine A., and Kyriacos A. Athanasiou. 2005. "Growth Factors and Fibrochondrocytes in Scaffolds." Journal of Orthopaedic Research: Official Publication of the Orthopaedic Research Society 23 (5): 1184-90. https://doi.org/10.1016/j.orthres.2005.01.019.

Rodriguez, Ciro A., Hernan Lara-Padilla, and David Dean. 2018. "Bioceramics for Musculoskeletal Regenerative Medicine: Materials and Manufacturing Process Compatibility for Synthetic Bone Grafts and Medical Devices." In 3D Printing and Biofabrication, 1-33. Reference Series in Biomedical Engineering. Springer, Cham. https://doi.org/10.1007/978-3-319-40498-1_22-1.

Rosser, J., and D. J. Thomas. 2018. "10—Bioreactor Processes for Maturation of 3D Bioprinted Tissue." In 3D Bioprinting for Reconstructive Surgery, 191-215. Woodhead Publishing. https://doi.org/10.1016/B978-0-08-101103-4.00010-7.

Salgado, António J., Olga P. Coutinho, and Rui L. Reis. 2004. "Bone Tissue Engineering: State of the Art and Future Trends." Macromolecular Bioscience 4 (8): 743-65. https://doi.org/10.1002/mabi.200400026.

Schneider, Caroline A., Wayne S. Rasband, and Kevin W. Eliceiri. 2012. "NIH Image to ImageJ: 25 Years of Image Analysis." Nature Methods 9 (7): 671-75.

Sela, Jona J., and Itai A. Bab. 2012. "Healing of Bone Fracture: General Concepts." In Principles of Bone Regeneration, 1-8. Springer, Boston, MA. https://doi.org/10.1007/978-1-4614-2059-0_1.

Sipos, Wolfgang, Ursula Föger-Samwald, and Peter Pietschmann. 2014. "Supporting Apparatus of Vertebrates: Skeleton and Bones." In Comparative Medicine, 35-44. Springer, Vienna. https://doi.org/10.1007/978-3-7091-1559-6_3.

Sladkova, Martina, and Giuseppe Maria de Peppo. 2014. "Bioreactor Systems for Human Bone Tissue Engineering." Processes 2 (2): 494-525. https://doi.org/10.3390/pr2020494.

Sun, C., N. Fang, D. M. Wu, and X. Zhang. 2005. "Projection Micro-Stereolithography Using Digital Micro-Mirror Dynamic Mask." Sensors and Actuators A: Physical 121 (1): 113-20. https://doi.org/10.1016/j.sna.2004.12.011.

Taubin, G. 1995. "Curve and Surface Smoothing without Shrinkage." In Proceedings of IEEE International Conference on Computer Vision, 852-57. https://doi.org/10.1109/ICCV.1995.466848.

Walker, Jason M., Emily Bodamer, Alex Kleinfehn, Yuanyuan Luo, Matthew Becker, and David Dean. 2017. "Design and Mechanical Characterization of Solid and Highly Porous 3D Printed Poly(Propylene Fumarate) Scaffolds." Progress in Additive Manufacturing 2 (1-2): 99-108. https://doi.org/10.1007/s40964-017-0021-3.

Wendt, D., S. A. Riboldi, M. Cioffi, and I. Martin. 2009. "Bioreactors in Tissue Engineering: Scientific Challenges and Clinical Perspectives." Advances in Biochemical Engineering/Biotechnology 112: 1-27. https://doi.org/10.1007/978-3-540-69357-4_1.

Wu, Xiangquan, Qin Lian, Dichen Li, and Zhongmin Jin. 2017. "Tilting Separation Analysis of Bottom-up Mask Projection Stereolithography Based on Cohesive Zone Model." Journal of Materials Processing Technology 243 (May): 184-96. https://doi.org/10.1016/j.jmatprotec.2016.12.016.

Yeatts, Andrew B., and John P. Fisher. 2011. "Bone Tissue Engineering Bioreactors: Dynamic Culture and the Influence of Shear Stress." Bone 48 (2): 171-81. https://doi.org/10.1016/j.bone.2010.09.138.

Zhou, Chi, Yong Chen, Zhigang Yang, and Behrokh Khoshnevis. 2013. "Digital Material Fabrication Using Mask-image-projection-based Stereolithography." Rapid Prototyping Journal 19 (3): 153-65. https://doi.org/10.1108/13552541311312148.

International Search Report and Written Opinion issued by the International Searching Authority (ISA/US) in PCT Application No. PCT/US2019/045588 on Nov. 21, 2019. 12 pages.

Extended European Search report issued for Application No. 19846543.7, dated May 30, 2022.

\* cited by examiner

FABRICATION OF POROUS SCAFFOLDS USING ADDITIVE MANUFACTURING WITH POTENTIAL APPLICATIONS IN BONE TISSUE ENGINEERING

CROSS-REFERENCE TO RELATED APPLICATIONS

This application is a national stage application filed under 35 U.S.C. § 371 of PCT/US2019/045588 filed Aug. 7, 2019, which claims the benefit of U.S. Provisional Application No. 62/715,596, filed Aug. 7, 2018, the disclosure of which is incorporated herein by reference in its entirety.

STATEMENT OF GOVERNMENT SUPPORT

This invention was made with government support under W81XWH-14-2-0004 awarded by the ARMY Medical Research and Material Command. The government has certain rights in the invention.

TECHNICAL FIELD

This disclosure related to additive manufacturing methods, and more particularly to methods for optimizing three-dimensional printing processes. Also described are bioreactor designs as well as methods of using thereof.

BACKGROUND

Bones provide several functions, from load-bearing, structural integrity and protection to hematopoietic and immunological cell creation. The types of bone have been classified according to their functions, shapes and sizes ("Atlas of Human Anatomy-6th Edition" n.d.). The main two components of mineralized tissue are cortical bone and cancellous bone. Cortical bone is also called "compact bone" as it is much denser and forms the hard exterior of bones. Its main function is mechanical, supporting and/or protecting organs. It also serves as mineral (especially calcium) storage, comprising about 80% of the total bone mass in an adult. Cancellous bone is also known as trabecular of spongy bone tissue, and is an open cell porous network, which makes it ideal for metabolic activities. It is rich in bone marrow and hematopoietic stem cells, and blood vessels. It comprises about 20% of the adult human's total bone mass. Cancellous bone is typically found at the end of long bones, near joints and within the interior.

In general, the bone is regarded as a tough matrix that is mineralized that gives it its strength. The matrix is about 30% of the bone and over 90% is based on collagen fibers, the rest is a gel-like substance in the extracellular space that comprises of all components of the extracellular matrix. The remaining 70% of the bone is comprised of minerals and salts that provide strength ("Guyton and Hall Textbook of Medical Physiology—12th Edition" n.d.). Minerals in bone are mostly calcium phosphate in the form of hydroxyapatite. All these are created by bone-forming cells, known as osteoblasts that produce mostly type 1 collagen. Osteoblasts secretes these collagen fibers all around themselves and then they deposit calcium phosphate. This new bone is called osteoid. Once the Osteoblast is trapped, it is known as an Osteocyte. Osteoclasts are large cells that resorb the bone, in a never-ending remodeling that is balanced by osteoblasts, and that are also play an important role in calcium homeostasis ("Guyton and Hall Textbook of Medical Physiology—12th Edition" n.d.). The key regulator of osteoblast and osteoclast activity is mechanical strain, such as when there's increased load, the bone will adapt and add new bone in response to it or remove in response to unloading (Burr, Robling, and Turner 2002).

Bone defects are a common occurrence in life that come from several etiologies, such as high-energy trauma, birth defects, injuries, osteoporosis derived pathological fractures, gunshot trauma, iatrogenic resection of infected or neoplastic bone lesions and a whole myriad of causes that can affect patients in the long term. These defects are dependent on the size, place, and type of bone in which they occur. The ability to repair them depend on the available stock for bone grafting. Critical size segmental defects are generally considered as defects that will never heal on their own without any intervention by a surgeon. Bone grafting requires placing plates, screws and guides, and sometimes other measures. Critical size defects are the most difficult to treat, and prior to the advent of complex reconstructive surgical procedures, most of them ended up in amputation or permanent functional deficits. Unfortunately, there are no artificial bone grafts that can restore full functionality and that can be well tolerated by the patients undergoing the approach (Gugala, Lindsey, and Gogolewski 2007). Because life expectancy continues to increase, these cases are rising in occurrence, being the most demanding spinal fusion and nonunion fractures (Kinaci, Neuhaus, and Ring 2014).

Today, the use of bone grafting remains the standard-of-cap in the clinic for longbone segmental defects, but the results are far from perfect. It is estimated that every year around 1 million bone allografts are used (Ng 2012). They come with complications that are way too common, from rejection to infection, take too long to heal, they never approach full range of function and some poor outcomes in general. These interventions include the more common treatment using cancellous bone grafting, as well as cortical allografts, vascularized bone grafts, and distraction osteogenesis (DeCoster et al. 2004). The major shortcomings of these interventions are due to several factors, being the most important lack of structural integrity and high failure in large bone defects due to rapid graft resorption. They come with the added restrictions that are limited availability and morbidity of the donor site (Banic and Hertel 1993).

These problems have pushed practice to look for other approaches, being bone graft substitutes a huge area of research. These strides have focused on osteogenic options such as bone marrow aspirate and blood concentration to remove platelet-rich plasma, as well as osteoconductive fillers, comprising ceramics, cements, and polymers (synthetic or natural) as well as addition of osteoinductive molecules like growth factors and cytokines. Tissue engineering has tested several constructs and as of today, the most potent osteoinductive additions are demineralized bone matrix and recombinant human morphogenetic proteins approved for use in bone deficiencies (Gugala, Lindsey, and Gogolewski 2007).

It is important to mention that even though autologous and allogenic bone grafts are being used, they often require a frame and a vascularization (e.g muscle and/or arterial graft) to allow for tissue to be regenerated, and that is the common focus on research today. The use of a scaffold in combination with bone substitutes and/or aggregates may allow better results and expand the use of allografting as we know it or even supplement it. The push in today's biomaterials' research has focused on implants that aide in the structure, vascularization, and grow factors for implanted bone grafts (Griffin et al. 2015). The search for a successful bone scaffold seeks three main properties: osteoconditivity, osteointegration and osteoinductivity. Cancellous grafts have mild-to moderate osteoconductive properties, mild osteoinductive ones, and practically no structural strength. Cortical bone grafts provide great strength and stability but are very poor in osteoinduction (Giannoudis, Dinopoulos, and Tsiridis 2005).

The generation of a "artificial bone" substitute to repair skeletal defects has been the concern of mankind for thousands of years. The substitution of bone parts can be considered as early efforts to use biomaterials in reconstructive medicine. For instance, diversity of methods has been proposed for cranium reconstruction from prehistory to modern medicine attests to the engaging nature of the problem (Abhay and Haines 1997). During the last decades, this concept became feasible and has been recently introduced in medicine. Tissue engineering and regenerative medicine are terms for the field in biomedicine that deal with the transformation of these fundamental ideas to practical approaches (Meyer 2009).

Current approaches to skeletal reconstructive surgery use biomaterials, autografts or allografts, although restrictions on all these techniques exist. These restrictions include donor site morbidity, pain and donor shortage for autografts, immunological rejection, and the risk of transmitting infectious diseases (Laurencin, Khan, and El-Amin 2006). Many artificial tissue substitutes containing metals, ceramics, and polymers were introduced to maintain skeletal function. However, each material has specific disadvantages, and none of these can perfectly substitute for autografts in current clinical practice. The use of biomaterials is a common treatment option in clinical practice. One reason for the priority of tissue grafts over nonliving biomaterials is that they contain cells and tissue-inducing substances, thereby possessing biological plasticity (Meyer et al. 2009). Research is currently in progress to develop cell-containing hybrid materials and to create replacements for bone tissue that are bioactive after implantation, imparting physiological functions as well as structure to the tissue or organ damaged by disease or trauma.

Additive manufacturing technologies have unlocked new possibilities for bone tissue engineering (BTE). Long-term regeneration of regular anatomic structure, shape, and function is clinically essential after bone trauma, tumor, infection, nonunion after fracture, or congenital abnormality. Additive manufacturing could provide the ability to print bone substitute materials with controlled chemistry, shape, porosity, and topography, thus allowing printing of personalized bone grafts customized to the patient and the specific clinical condition (Jariwala et al. 2015).

While there is no clinically available "bone substitute", potentially promising process for the generation of a synthetic bone graft has been suggested by (Rodriguez, Lara-Padilla, and Dean 2018). Briefly, based on the type of the bone defect, the initial point will be synthetic bone graft design. At the next stage, a scaffold is manufactured. The subsequent stage involves combining cells with the scaffold to constitute a synthetic bone graft. Growth factors may be added at this stage. In some cases, the scaffold alone (cell-free scaffold) is used as the graft. Finally, the synthetic bone graft is implanted into the bone defect to promote the regeneration of new tissue.

There is a clear need for novel methods and apparatuses for the manufacture of porous scaffolds for use in tissue engineering applications. Further, while methods and apparatuses for the manufacture of porous scaffolds can find use in tissue engineering applications, these insights may more broadly inform additive manufacturing processes in general.

SUMMARY

The present disclosure provides methods for optimizing the manufacture of three-dimensional objects (e.g., including situation-specific external shapes with porous internal surfaces) using three-dimensional printing processes. Methods are provided that help reduce the failure rate during manufacturing of these objects by 3D printing processes, an issue of significance due to the high tendency to fail during fabrication either due to stress concentrations in small regions, the use of relatively weak materials, or both.

Thus in one aspect, a method for optimizing an additive manufacturing process for the production of a three-dimensional object using an additive manufacturing device is provided, the method comprising:
evaluating inter-layer green strength for two layers of a build;
evaluating forces acting on the build during the additive manufacturing process;
comparing the inter-layer green strength to the forces acting on the build; and
altering one or more process parameters of the additive manufacturing process when the forces acting on the build are greater than the inter-layer green strength.

In some embodiment, the forces acting on the build comprise one or more of stretching of the build, torsion of the build (e.g., on the part while it is being built), shrinking of the build, compression of the build, elongation of the build, adhesion of the build, or any combination thereof. In some embodiments, altering one or more process parameters comprises changing the orientation of the build with respect to the additive manufacturing device. In some embodiments, changing the orientation of the build comprises selecting a new orientation wherein the forces acting on the build are less than the inter-layer green strength. In some embodiments, altering one or more process parameters comprises selecting a different additive manufacturing device for production of the three-dimensional object. In some embodiments, altering one or more process parameters comprises modifying structural elements of the build. In some embodiments, modifying structural elements of the build comprises increasing cross-sectional overlap between the two layers of the build. In some embodiments, modifying structural elements of the build increases the inter-layer green strength such that it is greater than the forces acting on the build during the additive manufacturing process.

In some embodiments, wherein altering one or more process parameters comprises altering a material used to form the build during the additive manufacturing process. the material used to form the build during the additive manufacturing process comprises a light polymerizable material, and wherein altering the material comprises selecting a different light polymerizable material. In some embodiments, the different light polymerizable material exhibits different rheological properties than the material used to form the build during the additive manufacturing process. In some embodiments, the material used to form the build during the additive manufacturing process comprises a light polymerizable material, and wherein altering one or more process parameters comprises altering incident energy applied to the light polymerizable material to induce crosslinking. In some embodiments, altering incident energy comprises varying a wavelength of incident light, varying an intensity of incident light, varying a duration of incident light, or any combination thereof.

In some embodiments, evaluating inter-layer green strength for two layers of the build comprises measuring the inter-layer green strength. evaluating inter-layer green strength for two layers of the build comprises modeling the inter-layer green strength. In some embodiments, modeling the inter-layer green strength comprises computational modeling. In some embodiments, modeling the inter-layer green strength comprises measuring the inter-layer green strength of a model of the build.

In some embodiments, evaluating forces acting on the build comprises measuring forces acting on the build during the manufacturing process. In some embodiments, evaluating forces acting on the build comprises modeling the forces acting on the build. In some embodiments, modeling the forces acting on the build comprises computation modeling. In some embodiments, modeling the forces acting on the build comprises measuring forces acting on a model of the build. In some embodiments, the model of the build further comprises internal force sensors.

In another aspect, a method for optimizing the manufacture of a layer of an object using an additive manufacturing process is provided, wherein the object is subjected to one or more forces during its manufacture, the method comprising:
 (a) determining the inter-layer green strength of the layer;
 (b) determining each quantity of force applied to the layer as the object is built layer-by-layer;
 (c) comparing the inter-layer green strength to each quantity of force experience by the layer at any point of the manufacturing process;
 wherein if a quantity of force applied is greater than the inter-layer green strength, the design of the structure of the layer is modified to increase cross-sectional overlap of layer with one or more adjacent layers.

In another aspect, a method for optimizing the manufacture of a layer of an object using an additive manufacturing process, wherein the object is composed of a material, and wherein the object is subjected to one or more forces during its manufacture, the method comprising:
 (a) determining the inter-layer green strength of the layer;
 (b) determining each quantity of force applied to the layer as the object is built layer-by-layer;
 (c) comparing the inter-layer green strength to each quantity of force experience by the layer at any point of the manufacturing process;
 wherein if a quantity of force applied is greater than the inter-layer green strength, the manufacture of the object is modified to replace the material from which it is composed with a second material that has an inter-layer green strength greater than any quantity of force applied to the layer.

In another aspect, a method for selecting between a first orientation and a second orientation for manufacturing an object using an additive manufacturing process, wherein the object is manufactured in the first orientation out of a first plurality of layers and in the second orientation out of a second plurality of layers, and wherein the object is subjected to one or more forces during its manufacture, the method comprising:
 (a) determining the ratio of an average of the force applied to each layer of the first plurality of layers to the average of the inter-layer green strength of each layer of the first plurality of layers to provide a first force to green strength ratio;
 (b) determining ratio of an average of the force applied to each layer of the second plurality of layers to the average of the inter-layer green strength of each layer of the second plurality of layers to provide a second force to green strength ratio;
 (c) comparing the first force to green strength ratio to the second force to green strength ratio; and
 (d) selecting the orientation for manufacture that is associated with the lesser of the first force to green strength ratio and the second force to green strength ratio.

In some embodiments, the additive manufacturing process is selected from a material extrusion process, a powder bed fusion process, a binder jetting process, a stereolithography process, a computed axial lithography process, a liquid additive (e.g., hydrogel bioprinting, hydrogel bioassembly, or photocrosslinked hydrogel) manufacturing process, or a directed energy deposition (DED) process. In some embodiments, the additive manufacturing process is continuous digital processing (cDLP).

In some embodiments, the force applied to the object is a separation force.

In some embodiments, the object is manufactured from a resin composition comprising a liquid light-curable material and a photoinitiator.

In some embodiments, the separation force of a layer is determined by:
 (a) providing an additive manufacturing apparatus including a Digital Micromirror Device (DMD) that is part of a cDLP 3D printer, a transparent or translucent basement plate, and a build plate operatively coupled to a force sensor;
 (b) depositing an amount of the resin composition above the basement plate;
 (c) activating the DMD to expose a portion of the resin composition to light to at least partially crosslink the liquid light-curable polymerizable material therein to form the layer of the three-dimensional object;
 (d) actuating the build plate or the basement plate to increase the distance between the build plate and the basement plate such that the layer of the three-dimensional object is separated from the basement plate;
 (e) measuring the separation force required to separate the layer of the three-dimensional object from the basement plate with the force sensor during step (d).

In some embodiments, the inter-layer green strength of the material is determined by:
 (a) providing an additive manufacturing apparatus including a Digital Micromirror Device (DMD), a transparent or translucent basement plate, and a build plate operatively coupled to a force sensor;
 (b) depositing an amount of the resin composition above the basement plate;
 (c) actuating the DMD to expose a portion of the resin composition to light to at least partially crosslink the liquid light-curable polymerizable material therein to form the first layer having a first cross-sectional area;
 (d) actuating the build plate or the transparent or translucent basement plate to increase the distance between the build plate and the basement plate to separate the first layer from the basement plate;
 (e) actuating the DMD to expose an additional portion of the resin composition to light to at least partially crosslink the liquid light-curable polymerizable material to form a second layer having a second cross-sectional area and to at least partially overcure at least some of the first layer to the second layer to cause at least some interlayer binding between the first layer and the second layer, wherein the second cross-sectional area is greater than the first cross-section area;
 (f) actuating the build plate or the basement plate to separate the second from the basement plate, wherein the force sensor measures the separation force required to separate the second layer from the basement plate;

(g) measuring the separation force required to separate the second layer from the basement plate with the force sensor during step (f);

(h) repeating steps (e), (f) and (g) to form one or more additional layers have one or more additional cross-sectional areas until there is a failure of the interlayer binding of any two of the layers upon actuation of the build plate or basement plate, wherein each additional cross-sectional area is greater than the cross-sectional area of the previous layer;

(i) calculating the inter-layer green strength by dividing the separation force measured for the most recent additional layer manufactured during step (h) upon failure of interlayer binding by the additional cross-sectional area of the most recent additional layer.

In another aspect, a method for optimizing the manufacture of a layer of an object using continuous digital light processing (cDLP), wherein the layer has a cross-sectional area, and wherein the object is composed of a material manufactured from a resin composition comprising a liquid light-curable polymer and a photoinitiator, the method comprising:

(a) measuring the separation force for a test layer having substantially the same cross-sectional area as the layer of the three-dimensional object using the method described above;

(b) measuring the inter-layer green strength of the material using the method described above;

(c) calculating the probability of structural failure of the layer by comparing the separation force of the test layer with the inter-layer green force of the material, wherein if the separation force of the test layer is greater than the inter-layer green force of the material, the resin composition is modified.

In another aspect, a method for optimizing the manufacture of a layer of a three-dimensional object using continuous digital light processing (cDLP), wherein the layer has a cross-sectional area, and wherein the object is composed of a material manufactured from a resin composition comprising a liquid light-curable polymer and a photoinitiator, the method comprising:

(a) measuring the separation force for a test layer having substantially the same cross-sectional area as the layer of the three-dimensional object using the method described above;

(b) measuring the inter-layer green strength of the material using the method described above;

(c) calculating the probability of structural failure of the layer by comparing the separation force of the test layer with the inter-layer green force of the material, wherein if the separation force of the test layer is greater than the inter-layer green force of the material, the structure of the layer of the three-dimensional object such that cross-sectional overlap between the layer and one or more adjacent layers is increased.

In some embodiments, the three-dimensional object is a tissue engineering scaffold. In some embodiments, the produced scaffold includes pores having openings with diameters in the range of 50 to 1600 micrometers. In some embodiments, the scaffold includes pores having a substantially cylindrical structure. In some embodiments, the scaffold includes pores having a substantially oblique structure.

In some embodiments, the liquid light-polymerizable material has a molecular weight of approximately 4,000 Daltons or less. In some embodiments, the liquid light-polymerizable material includes poly(propylene fumarate) (PPF). In some embodiments, the resin composition further comprises a dye. In some embodiments, the ratio of dye to photoinitiator is selected to control the depth of penetration of light. In some embodiments, the dye includes 2-hydroxy-4-methoxybenzophenone. In some embodiments, the photoinitiator includes bis(2,4,6-trimethylbenzoyl)phenylphosphine oxide (BAPO). In some embodiments, the photoinitiator includes bis[2,6-difluoro-3-(1-hydroxypyrrol-1-yl)phenyl]titanocene. In some embodiments, the resin composition further comprises a solvent. In some embodiments, the resin composition further comprises diethyl fumarate (DEF).

In another aspect, a direct perfusion bioreactor system for three-dimensional tissue culture of a tissue engineering scaffold is provided comprising:

At least one perfusion chamber for housing the tissue engineering scaffold having a chamber flow inlet and a chamber flow outlet;

An in-line peristaltic pump having a pump flow inlet and a pump flow outlet;

a culture medium reservoir having a reservoir flow inlet and a reservoir flow outlet;

wherein the pump flow outlet is in fluid communication with the chamber flow inlet;

wherein the chamber flow outlet is in fluid communication with the reservoir flow inlet; and wherein the reservoir flow outlet is in fluid communication with the pump flow inlet.

In some embodiments, the perfusion chamber and culture medium reservoir are housed within an incubator. In some embodiments, the peristaltic pump is housed outside an incubator. In some embodiments, the perfusion chamber is composed of a disposable material. In some embodiments, the perfusion chamber is a syringe. In some embodiments, the perfusion chamber is composed of soft tubing. In some embodiments, the soft tubing is subjected to an external pressure to conform the tubing to the shape of the tissue engineering scaffold. In some embodiments, the bioreactor system comprises two or more perfusion chambers. In some embodiments, the pump flow outlet is in fluid communication with the chamber flow inlet by plastic tubing. In some embodiments, the chamber flow outlet is in fluid communication with the reservoir flow inlet by plastic tubing. In some embodiments, the reservoir flow outlet is in fluid communication with the pump flow inlet by plastic tubing. In some embodiments, the tissue engineering scaffold is held in place within the at least one perfusion chamber by a pair of conical springs.

The details of one or more embodiments of the disclosure are set forth in the accompanying drawings and the description below. Other features, objects, and advantages of the disclosure will be apparent from the description and the drawings, and from the claims.

DETAILED DESCRIPTION

Figure 1:
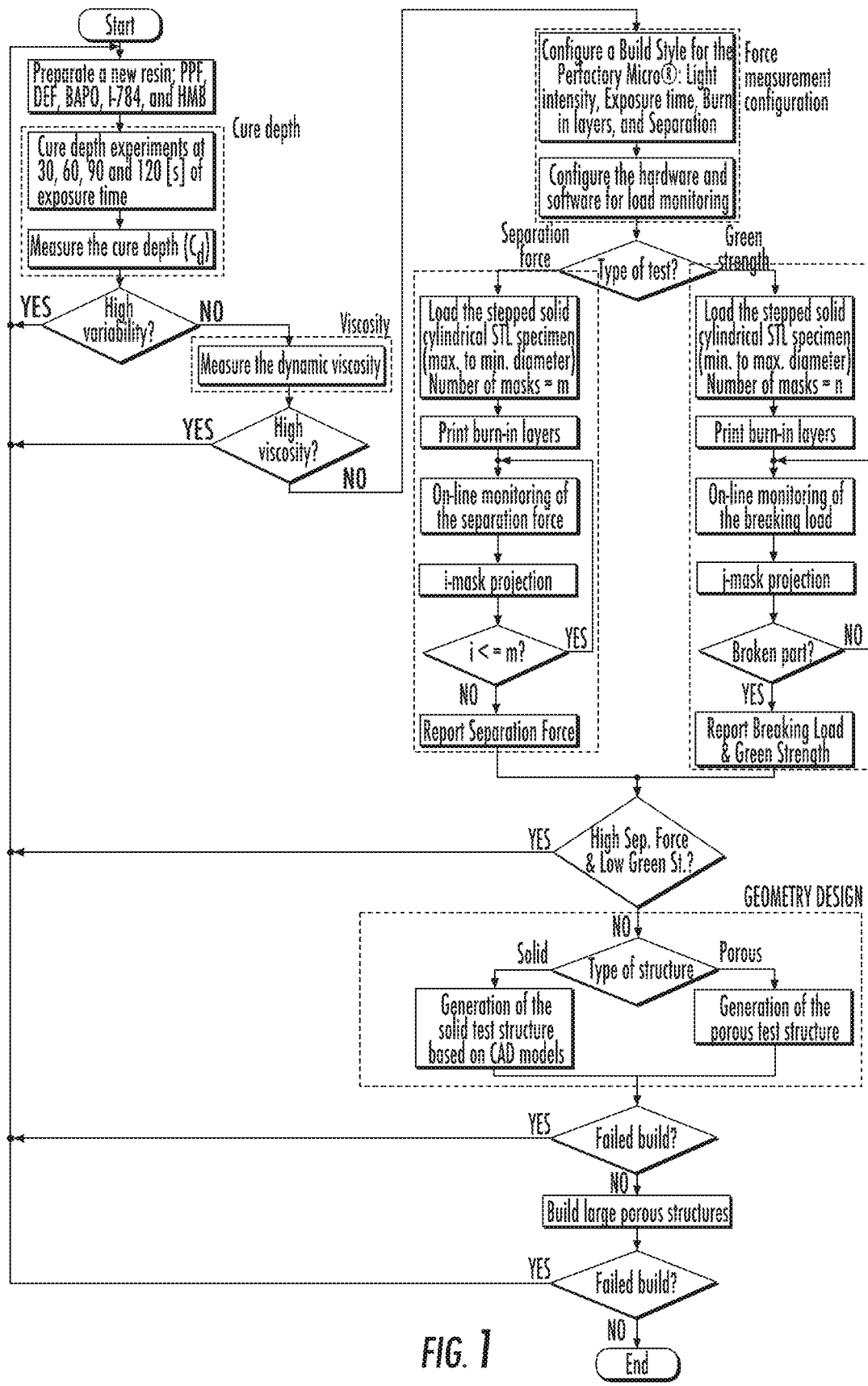
FIG. 1 is a flowchart of the model strategy for the optimization of manufacturing processes using continuous digital light processing. Several tests are necessary to evaluate the printability of a resin made with PPF. Cure depth, resin viscosity, separation force and green strength were evaluated as printability criteria.

Unless defined otherwise, all technical and scientific terms used herein have the same meaning as commonly understood to one of ordinary skill in the art to which this invention belongs. The following definitions are provided for the full understanding of the terms used in the specification.

As used in the specification and claims, the singular form "a", "an", and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Breaking load" as used herein refers to the load applied at some point to a component or structure which leads to fracture.

"Build" as used herein refers to a 3-dimensional object being formed by a layer-by-layer additive manufacturing process.

"Burn-in layers" as used herein refers to the early layers needed to stick the printed part to the build platform. In some embodiments, the burn-in layers need 2×-4× times higher cure time than normal layers.

"Cure depth" refers to the thickness of a single layer of a photo resin exposed to a certain amount of exposure time.

"Dye-initiator" as used herein refers to a compound used to ensure accurate control of the depth of polymerization.

"Dynamic viscosity" as used herein refers to the ratio, for a fluid, of the viscous shear stress to the rate of strain. It may vary with temperature and pressure.

"Exposure time" as used herein refers to the amount of time used to project a digital mask using light to cure a layer during the 3D printing process with cDLP.

"Green strength" or "overall green strength" is a general term that comprises all the mechanical properties of the light-cured part including modulus, strain, strength, hardness, and layer-to-layer adhesion. It must be sufficiently large that a part will not distort before or during the final postcure.

"Growth factors" as used herein refers to a diverse group of proteins that are important in the regulation of cell proliferation (growth) and differentiation.

"Inter-layer green strength" or "Layer stitching" or "Inter-layer binding" as used herein refers to a grade of strength as an indication of crosslinking density during the exposure time of each layer during a layer-by-layer additive manufacturing process. In some cases, the additive manufacturing process can be continuous Digital Light Processing (cDLP).

"Layer thickness" as used herein is the nominal thickness of a single layer obtained in the cure depth experiment.

"Overcuring" as described herein is the thickness of the layer minus step size.

"Photoinitiator" as described herein is a chemical that undergoes a photoreaction on absorption of light, induces polymerization.

"Resin" refers to a viscous substance of organic or synthetic origin that is typically convertible into a polymer.

"Separation velocity" refers to the velocity of the build elevation as it pulls away from the basement.

"Solvent" as used herein refers to a compound used to reduce the viscosity of photopolymer resins.

"Step size" refers to the gap between the bottom part of basement (vat) and the last cured layer.

The terms additive manufacturing process and 3-d printing are used herein synonymously.

Additive Manufacturing Processes

Additive manufacturing comprises building a three-dimensional object from a computer-aided design (CAD) model, usually by successively adding material layer by layer. The term covers a variety of processes in which material is joined or solidified under computer control to create a three-dimensional object, with material being added together (such as liquid molecules or powder grains being fused together), typically layer by layer. 3D printing processes typically comprise the steps of modeling the object on a computer, printing using any of the processes described herein, and finishing the product as deemed necessary for the particular application.

3D printable models may be created with a computer-aided design (CAD) package, via a 3D scanner, or by a plain digital camera and photogrammetry software. 3D printed models created with CAD result in reduced errors and can be corrected before printing, allowing verification in the design of the object before it is printed. 3D scanning is a process of collecting data on the shape and appearance of a real object, creating a digital model based on it.

CAD models can be saved in the stereolithography (STL) file format, a de factor CAD file format for additive manufacturing that stores data based on triangulations of the surface of CAD models. STL is not tailored for additive manufacturing because it generates large file sizes of topology optimized parts and lattice structures due to the large number of surfaces involved. A new CAD file format, the Additive Manufacturing File (AMF) format, was introduced in 2011 to solve this problem.

Before printing a 3D model from an STL file, it must first be examining for errors. Most CAD application produce errors in output STL files of the following types: holes; face normal; self-intersections; noise shells; and manifold errors. A step in the STL generation known as "repair" fixes such problems in the original model. Generally, STLs that have been produced from a model obtained through 3D scanning often have more of these errors. This is due to how 3D scanning works. As it is often by point to point acquisition, 3D reconstruction will include errors in most cases.

Once completed, the STL file needs to be processed by a piece of software called a "slicer," which converts the model into a series of thin layers and produces a G-code file containing instructions tailored to a specific type of 3D printer (FDM printers). This G-code file can then be printed with 3D printing client software (which loads the G-code, and uses it to instruct the 3D printer during the 3D printing process).

Printer resolution describes layer thickness and X-Y resolution in dots per inch (dpi) or micrometers (μm). Typical layer thickness is around 100 μm (250 DPI), although some machines can print layers as thin as 16 μm (1,600 DPI). X-Y resolution is comparable to that of laser printers. The particles (3D dots) are around 50 to 100 μm (510 to 250 DPI) in diameter. For that printer resolution, specifying a mesh resolution of 0.01-0.03 mm and a chord length≤ 0.016 mm generate an optimal STL output file for a given model input file. Specifying higher resolution results in larger files without increase in print quality.

Though the printer-produced resolution is sufficient for many applications, greater accuracy can be achieved by printing a slightly oversized version of the desired object in standard resolution and then removing material using a higher-resolution subtractive process. The layered structure of all Additive Manufacturing processes leads inevitably to a strain-stepping effect on part surfaces which are curved or tilted in respect to the building platform. The effects strongly depend on the orientation of a part surface inside the building process. Some printable polymers such as ABS, allow the surface finish to be smoothed and improved using chemical vapor processes based on acetone or similar solvents. Some additive manufacturing techniques are capable of using multiple materials in the course of constructing parts. These techniques are able to print in multiple colors and color combinations simultaneously, and would not necessarily require painting. Some printing techniques require internal supports to be built for overhanging features during construction. These supports must be mechanically removed or dissolved upon completion of the print. All of the commercialized metal 3D printers involve cutting the metal component off the metal substrate after deposition. A new process for the GMAW 3D printing allows for substrate surface modifications to remove aluminum or steel.

A large number of additive processes are available. The main differences between processes are in the way layers are deposited to create parts and in the materials that are used. Some methods melt or soften the material to produce the layers, for example. selective laser melting (SLM) or direct metal laser sintering (DMLS), selective laser sintering (SLS), fused deposition modeling (FDM), or fused filament fabrication (FFF), while others cure liquid materials using different sophisticated technologies, such as stereolithography (SLA). With laminated object manufacturing (LOM), thin layers are cut to shape and joined together (e.g., paper, polymer, metal). Each method has its own advantages and drawbacks, which is why some companies offer a choice of powder and polymer for the material used to build the object. Others sometimes use standard, off-the-shelf business paper as the build material to produce a durable prototype. The main considerations in choosing a machine are generally speed, costs of the 3D printer, of the printed prototype, choice and cost of the materials, and color capabilities. Printers that work directly with metals are generally expensive. However less expensive printers can be used to make a mold, which is then used to make metal parts.

Fused deposition modeling (FDM), derives from automatic polymeric foil hot air welding system, hot-melt gluing and automatic gasket deposition. In fused deposition modeling, the model or part is produced by extruding small beads or streams of material which harden immediately to form layers. A filament of thermoplastic or other low melting point material or mixture is fed into an extrusion nozzle head (3D printer extruder), where the filament is heated to its melting temperature and extruded onto a build table. More recently, fused pellet deposition (or fused particle deposition) has been developed, where particles or pellets of plastic replace the need to use filament. The nozzle head heats the material and turns the flow on and off. Typically stepper motors or servo motors are employed to move the extrusion head and adjust the flow. The printer usually has 3 axes of motion. A computer-aided manufacturing (CAM) software package is used to generate the G-Code that is sent to a microcontroller which controls the motors.

Plastic is the most common material for such printing. Various polymers may be used, including acrylonitrile butadiene styrene (ABS), polycarbonate (PC), polylactic acid (PLA), high-density polyethylene (HDPE), PC/ABS, polyphenylsulfone (PPSU) and high impact polystyrene (HIPS). In general, the polymer is in the form of a filament fabricated from virgin resins. There are multiple projects in the open-sourced community aimed at processing post-consumer plastic waste into filament. These involve machines used to shred and extrude the plastic material into filament such as recyclebots. Additionally, fluoropolymers such as PTFE tubing are used in the process due to the material's ability to withstand high temperatures. This ability is especially useful in transferring filaments.

FDM is somewhat restricted in the variation of shapes that may be fabricated. For example, FDM usually cannot produce stalactite-like structures, since they would be unsupported during the build. Otherwise, a thin support must be designed into the structure, which can be broken away during finishing. Usually, the software that converts the 3D model into a set of flat layers, called slicer, takes care of the addition of these supports and some other resources to allow the fabrication of this kind of shapes.

Another 3D printing approach is the selective fusing of materials in a granular bed. The technique fuses parts of the layer and then moves upward in the working area, adding another layer of granules and repeating the process until the piece has built up. This process uses the unfused media to support overhangs and thin walls in the part being produced, which reduces the need for temporary auxiliary supports for the piece. For example, in selective heat sintering, a thermal printhead applies heat to layers of powdered thermoplastic; when a layer is finished, the powder bed moves down, and an automated roller adds a new layer of material which is sintered to form the next cross-section of the model; using a less intense thermal printhead instead of a laser, makes this a cheaper solution than using lasers, and can be scaled down to desktop sizes.

Laser sintering techniques include selective laser sintering (SLS), with both metals and polymers (e.g., PA, PA-GF, Rigid GF, PEEK, PS, Alumide, Carbonmide, elastomers), and direct metal laser sintering (DMLS).

Selective laser melting (SLM) does not use sintering for the fusion of powder granules but will completely melt the powder using a high-energy laser to create fully dense materials in a layer-wise method that has mechanical properties similar to those of conventional manufactured metals.

Electron beam melting (EBM) is a similar type of additive manufacturing technology for metal parts (e.g. titanium alloys). EBM manufactures parts by melting metal powder layer by layer with an electron beam in a high vacuum. Unlike metal sintering techniques that operate below melting point, EBM parts are void-free.

The binder jetting 3D printing technique is the deposition of a binding adhesive agent onto layers of material, usually powdered. The materials can be ceramic-based or metal. This method is also known as inkjet 3D printing system. To produce the piece, the printer builds the model using a head that moves over the platform base and deposits, one layer at a time, by spreading a layer of powder (plaster, or resins) and printing a binder in the cross-section of the part using an inkjet-like process. This is repeated until every layer has been printed. This technology allows the printing of full color prototypes, overhangs, and elastomer parts. The strength of bonded powder prints can be enhanced with wax or thermoset polymer impregnation.

The Stereolithography (SLA) process is based on light curing (photopolymerization) of liquid materials into a solid shape. In this process a vat of liquid polymer is exposed to controlled lighting (like a laser or a digital light projector) under safelight conditions. Most commonly the exposed liquid polymer hardens through cross-linking driven by the addition reaction of carbon carbon double bonds in acrylates. Polymerization occurs when photopolymers are exposed to light when photopolymers contain chromophores, otherwise, the addition of molecules that are photosensitive are utilized to react with the solution to begin polymerization. Polymerization of monomers lead to cross-linking, which creates a polymer. Through these covalent bonds, the property of the solution is changed. The build plate then moves down in small increments and the liquid polymer is again exposed to light. The process repeats until the model has been built. The liquid polymer is then drained from the vat, leaving the solid model. The EnvisionTEC Perfactory is an example of a DLP rapid prototyping system.

Inkjet printer systems like the Objet PolyJet system spray photopolymer materials onto a build tray in ultra-thin layers (between 16 and 30 μm) until the part is completed. Each photopolymer layer is cured with UV light after it is jetted, producing fully cured models that can be handled and used immediately, without post-curing. The gel-like support material, which is designed to support complicated geometries, is removed by hand and water jetting. It is also suitable for elastomers. There is another type of inkjet printing system available in the market that can print a photopolymer in a layer-by-layer manner, with intermediate UV curing, to produce ophthalmic corrective lenses. No support structures are required in this case, as ophthalmic lenses do not need overhangs. Luxexcel, a Dutch company, has commercialized this technology and printing platform.

Ultra-small features can be made with the 3D micro-fabrication technique used in multiphoton photopolymerisation. This approach uses a focused laser to trace the desired 3D object into a block of gel. Due to the nonlinear nature of photo excitation, the gel is cured to a solid only in the places where the laser was focused while the remaining gel is then washed away. Feature sizes of under 100 nm are easily produced, as well as complex structures with moving and interlocked parts. Yet another approach uses a synthetic resin that is solidified using LEDs.

In Mask-image-projection-based stereolithography, a 3D digital model is sliced by a set of horizontal planes. Each slice is converted into a two-dimensional mask image. The mask image is then projected onto a photocurable liquid resin surface and light is projected onto the resin to cure it in the shape of the layer. The technique has been used to create objects composed of multiple materials that cure at different rates. In research systems, the light is projected from below, allowing the resin to be quickly spread into uniform thin layers, reducing production time from hours to minutes. Commercially available devices such as Objet Connex apply the resin via small nozzles.

Continuous liquid interface production (CLIP) is another form of additive manufacturing that uses the DLP based photo polymerization process to create smooth-sided solid objects of a wide variety of shapes. The continuous process of CLIP begins with a pool of liquid photopolymer resin. Part of the pool bottom is transparent to ultraviolet light (the "window"). Like DLP systems before it, ultraviolet light beam shines through the window, illuminating the precise cross-section of the object. The light causes the resin to solidify. The object rises slowly enough to allow resin to flow under and maintain contact with the bottom of the object.[37] CLIP is different from traditional DLP processes, due to an oxygen-permeable membrane which lies below the resin, creating a "dead zone" (persistent liquid interface) preventing the resin from attaching to the window (photopolymerization is inhibited between the window and the polymerizer).

Unlike stereolithography, the printing process is considered continuous by its founders and considerably faster than traditional DLP processes, enabling the production of parts in minutes instead of hours.

Recently, the use of stereolithographic 3D printing techniques has been developed further to allow for the additive manufacturing of ceramic materials. Successful 3D printing of ceramics using stereolithography is achieved through the photopolymerisation of preceramic polymers to yield silicon based ceramics of a class known more widely as polymer derived ceramics, including silicon carbide and silicon oxycarbide.

Computed axial lithography is a method for 3D printing based on reversing the principle of computed tomography (CT) to create prints in photo-curable resin. Unlike other methods of 3D printing it does not build models through depositing layers of material like fused deposition modelling and stereolithography, instead it creates objects using a series of 2D images projected onto a cylinder of resin. It is notable for its ability to build objects much more quickly than other methods using resins and the ability to embed objects within the prints.

Liquid additive manufacturing (LAM) is an additive manufacturing technique which deposits a liquid or highly viscous material (e.g Liquid Silicone Rubber) onto a build surface to create an object, which is then vulcanised using heat to harden it.

In powder-fed directed-energy deposition, a high-power laser is used to melt metal powder supplied to the focus of the laser beam. The laser beam typically travels through the center of the deposition head and is focused to a small spot by one or more lenses. The build occurs on a X-Y table which is driven by a tool path created from a digital model to fabricate an object layer by layer. The deposition head is moved up vertically as each layer is completed. Metal powder is delivered and distributed around the circumference of the head or can be split by an internal manifold and delivered through nozzles arranged in various configurations around the deposition head. A hermetically sealed chamber filled with inert gas or a local inert shroud gas is often used to shield the melt pool from atmospheric oxygen for better control of material properties. The powder fed directed energy process is similar to Selective Laser Sintering, but the metal powder is applied only where material is being added to the part at that moment. The process supports a wide range of materials including titanium, stainless steel, aluminum, and other specialty materials as well as composites and functionally graded material. The process can not only fully build new metal parts but can also add material to existing parts for example for coatings, repair, and hybrid manufacturing applications. LENS (Laser Engineered Net Shaping), which was developed by Sandia National Labs, is one example of the Powder Fed-Directed Energy Deposition process for 3D printing or restoring metal parts.

Laser-based wirefeed systems, such as Laser Metal Deposition-wire (LMD-w), feed wire through a nozzle that is melted by a laser using inert gas shielding in either an open environment (gas surrounding the laser), or in a sealed chamber. Electron beam freeform fabrication uses an electron beam heat source inside a vacuum chamber.

It is also possible to use conventional gas metal arc welding attached to a 3D stage to 3-D print metals such as steel and aluminum. Low-cost open source RepRap-style 3-D printers have been outfitted with Arduino-based sensors and demonstrated reasonable metallurgical properties from conventional welding wire as feedstock.

Continuous Digital Light Processing cDLP is a type of the standardized additive manufacturing process called Vat photopolymerization, in which, liquid photopolymer in a vat is selectively cured by light-activated polymerization (ASTM-F2792). Synonyms as "constrained-surface stereolithography", "projection stereolithography", "bottom-up mask-projection stereolithography", "digital light processing stereolithography", "digital micromirror device-based printing", etc. have been used to describe cDLP. cDLP has great potential in the fabrication of high accuracy porous scaffolds for BTE in the micrometrical scale. cDLP employs ultraviolet light by projecting it to the resin activating initiators that crosslink the polymer layer, using dynamic masks to cure a whole layer at a time sequentially. Hence, this technique offers a significantly higher building speed than standard stereolithography (Dean et al. 2012).

A typical stereolithography system builds parts top down using a simple point laser. In cDLP, the vat is illuminated vertically upwards through a transparent window or "basement". After the system irradiates a binary layer, the cured resin sticks to the window and cures with the previous layer. The "build" platform pulls away from the window vertically or at a slight tilting angle to smoothly separate the part from the window. Three advantages of this system are remarkable. First, no separate recoating mechanism is needed since gravity forces refill the resin in the vat (i.e., region between the cured part and over the window). Second, the top vat surface being irradiated is a flat window, not a free surface, enabling more precise layers to be fabricated. Third, some cDLP systems have a build process that eliminates a regular vat as they have a supply-on-demand material feed system instead. The main disadvantage is that small or fine features may be damaged when the cured layer is separated from the window (Gibson, Rosen, and Stucker 2015).

A continuous digital light processing (cDLP) device includes a digital micro-mirror device (DMD) projector. A DMD consists of an array of micro-mirrors which controls the intensity of projected light in each pixel of the layer image, effectively polymerizing each voxel (volumetric pixel) of each layer of the implant IMP. The term "continuous" in continuous digital light processing indicates that all voxels within a layer can be projected simultaneously, as opposed to the successive drawing (i.e., moving of laser beam) of voxels that occurs in other additive manufacturing methods such as stereolithography. cDLP based additive manufacturing projects multiple voxels that may add up to a complete implant layer as one image, or "voxel mask." This allows for the entire layer to be cured simultaneously (i.e., continuous curing).

The projector projects light through a transparent or translucent basement plate above which is a resin including a liquid light-polymerizable material. Exposure to the light causes the resin to at least partially cure or polymerize to form layers of the implant IMP. In some embodiments, the device further includes a build plate to which the implant IMP operatively attaches. The build plate may operatively attach to a motor, the operation of which successively shifts or elevates the build plate away from the basement plate as the light successively cures or polymerizes the resin to form each layer of the implant IMP. The light further polymerizes or overcures previously rendered layers to bind or stitch newly polymerized layers to the previous layers.

In one embodiment, the cDLP device is the Perfactory® UV device produced by envisionTEC (Gladbeck, Germany). In another embodiment, the cDLP device would be a cDLP device other than the Perfactory® UV device produced by envisionTEC.

In one embodiment, each projected voxel mask also uses spatially varying irradiance, meaning that each pixel may be assigned a different light intensity value. Benefits of assigning each pixel a different intensity value include the ability of varying curing rates within a layer and allowing for anti-aliasing methods analogous to those found in image processing. In one embodiment, the cDLP device is equipped with an Enhanced Resolution Module (ERM) (not shown) which effectively doubles the within-layer (x-y) resolution through a process similar to pixel shifting, a technique which increases the true resolution of devices by moving the micro-mirrors by fractions of a pixel in the x and y directions.

The unique properties of cDLP rendering allow for improved accuracy defined as the similarity of the resulting implant or scaffold to the shape found in the design, or CAD, file. One source of increased accuracy is in-plane (x-y) resolution, which is a function of the projector lens magnification and the resolution of the DLP chip. Pixel sizes may be 75 micrometers or less. ERM, pixel shifting, anti-aliasing, or combinations thereof may further increase the in-plane resolution by at least a factor of 2.

The cDLP device further provides increased accuracy due to increased between-plane or (z) resolution. The between-plane (z) resolution is controlled by, among other factors, the motor (not shown), which shifts the build plate between serial layers. In one embodiment, the device has a motor capable of increments of 50 micrometers and as small as 15 micrometers. The between-plane (z) resolution may be further controlled by controlling the depth of penetration of the light to limit polymerizing energy into the resin or previously rendered layers of the implant IMP.

A model of the Perfactory® UV device has a motor capable of increments of 50 micrometers and a 60 millimeter lens, providing an in-plane (x-y) native resolution of 71 micrometers and 35.5 micrometers utilizing pixel shifting. Thus this model of the Perfactory® UV device is capable of continuously polymerizing 35.5×35.5×50 urn voxels. Another model of the Perfactory® UV device would have a 75 millimeter lens that would provide a 42 micrometer native in-plane (x-y) resolution and 21 micrometers resolution with pixel shifting.

Light-Polymerizable Materials

The cDLP process controls mechanical and other properties of the resulting implant IMP, in part, by controlling the molecular weight of the light-polymerizable material. Manipulation of the material's molecular weight adjusts the strength of the resulting implant IMP, with higher molecular weights generally being stronger. Thus, for applications where the implant IMP would bear significant mechanical stress, the light-polymerizable material may be chosen such that the rendered part may adequately handle and transmit the mechanical stress.

In applications such as implants or scaffolds, which are intended for implantation in a patient's body, it is important that components of the implant or scaffold including the light-polymerizable material as well as any initiators, dyes, solvents, and other substances be biocompatible, meaning that the implant poses no substantial risk of injury or toxicity to living cells, tissues, or organs, and poses no substantial risk of rejection by the immune system. In some instances, it is possible to use some non-biocompatible components or processes. However, they would usually be fully removed or rendered biocompatible prior to implantation. For example, some non-biocompatible chemicals may be used during the manufacturing process but be fully removed before implantation.

In applications such as tissue engineering scaffolds, resorbability of the scaffold, the ability of the part to break down in the host's body, is a very important consideration. It is important to the regeneration of tissue such as bone that the scaffold resorb in response to cell maturation and incoming host tissue. Well-timed scaffold resorption is important for successful integration of vasculature to allow unfettered remodeling and host incorporation of neotissue. Thus, predictable scaffold resorption is important including predictable rates of loss of material properties, predictable rates of scaffold degradation (e.g., it may be useful to choose polymers that fracture or erode at predictable rates rather than bulk degrade), and predictable rates pH change.

Strength and stiffness of the scaffold must be weighed against rates of resorbability of the scaffold. Manipulation of the material's molecular weight generally adjusts resorption levels versus strength of the scaffold with higher molecular weights resulting in stronger but less resorbable scaffolds and lower molecular weights resulting in weaker but more resorbable scaffolds.

Low molecular weight polymers are often capable of safely breaking down and be resorbed within the body. In general, resorbable polymers are often of very low molecular weight compared to polymers used in common automotive, aerospace, and industrial applications. Resorbable polymers usually have as low as 2-3 orders of magnitude lower molecular weight than the polymers used in those applications.

Low molecular weight polymers are often capable of safely breaking down and be resorbed within the body. In general, resorbable polymers are often of very low molecular weight compared to polymers used in common automotive, aerospace, and industrial applications. Resorbable polymers usually have as low as 2-3 orders of magnitude lower molecular weight than the polymers used in those applications.

In one embodiment, the cDLP process of the present disclosure uses the resorbable polymer poly(propylene fumarate) or PPF as the light-polymerizable material. PPF incorporates most of the characteristics discussed above for the light-polymerizable material including low molecular weight, no toxicity and resorbability. In another embodiment, the cDLP process of the present disclosure uses a resorbable light-polymerizable material other than PPF. In yet another embodiment, the cDLP process of the present disclosure uses a light-polymerizable material that although not resorbable is biocompatible or bioneutral. In one embodiment, the liquid light-polymerizable material has a molecular weight of approximately 4,000 Daltons or less. In another embodiment, the liquid light-polymerizable or light-curable material has a molecular weight of approximately 1,200 Daltons or less. In yet another embodiment, the light-curable material has a molecular weight in the range of 1,000 Daltons and 20,000 Daltons.

Some liquid light-polymerizable materials such as PPF are highly viscous. In cDLP, a missed layer may result if insufficient resin is available above the basement plate or if air bubbles form in that layer due to excessive viscosity of the resin incorporating the liquid light-polymerizable material. Viscous resins may also require a longer pause between layers, as more time is required for the flow into void spaces left in the areas where the previous layer was cured.

Use of a solvent may alleviate these issues by reducing the resin's viscosity. However, the use of a solvent may affect the rigidity of the implant or scaffold, with higher amounts of solvent making the implant less rigid. Ideally the resin's viscosity would be reduced without sacrificing implant rigidity. Moreover, any substance used to reduce the resin's viscosity would have to possess some of the same characteristics described above for the liquid light-polymerizable material including no toxicity.

In one embodiment where the liquid light-polymerizable material used in the resin 140 is PPF, diethyl fumarate (DEF) is added to the resin 140 to reduce the resin's viscosity. DEF is a monomer precursor to PPF. This monomer cross-links into the resulting implant or scaffold and once cross-linked poses little to no toxicity risk. In one embodiment, the proportion of DEF to PPF is 1:1 by weight. In one embodiment, the proportion of DEF to PPF is 1:2 by weight. In one embodiment, the proportion of DEF to PPF is 1:3 by weight. In another embodiment the proportion of DEF to PPF is less than 1:3 by weight. In yet another embodiment, the substance used to reduce the resin's viscosity is a substance other than DEF. In one embodiment, no substance is added to the resin to reduce the resin's viscosity.

Photoinitiators

Photo-initiators are added to the resin including the liquid light-polymerizable material to promote the polymerization reaction. In one embodiment, bis(2,4,6-trimethylbenzoyl) phenylphosphine oxide (BAPO) brand name Irgacure® 819 (BASF (Ciba Specialty Chemicals)) is used as the initiator. In one embodiment, the percentage by weight of initiator in a resin including the liquid light-polymerizable material is in the range of 0.5% and 1.0%. In another embodiment, the percentage by weight of initiator in a resin including the liquid light-polymerizable material is in the range of 1.0-2.0%. In another embodiment, the percentage by weight of initiator in a resin including the liquid light-polymerizable material is in the range of 2.0-3.0%. In other embodiments, the percentage by weight of initiator in a resin including the liquid light-polymerizable material is lower than 0.5% or higher than 3.0%.

As discussed above, the between-plane (z) resolution of the cDLP process may be further controlled by controlling the depth of penetration of polymerizing light energy into the light-polymerizable material being cured or previously cured implant layers. Some level of light penetration into previously rendered layers may be desired to ensure overcuring or stitching between layers, also known as interlayer binding. However, if light penetrates too deeply, previously cured layers may overcure resulting in undesired characteristics of the resulting implant or scaffold.

A property of the chosen dye to take into consideration is its ability to stay suspended in the resin throughout the rendering process. For some dyes, it may be necessary to stop the process and re-stir the resin if the dye is settling out.

In one embodiment, a dye is added to the resin including the liquid light-polymerizable material to at least in part control the depth of penetration of polymerizing light energy into the scaffold or implant layers and therefore assist in controlling interlayer binding. In one embodiment, the dye possesses some of the same characteristics described above for the liquid light-polymerizable material including no toxicity. For example, dyes such as azo chromium dye that may provide adequate control of the depth of penetration of polymerizing light energy into the scaffold or implant layers may be toxic and thus may not be well suited for implant applications.

The dye limits the depth of polymerization allowing for the option of using higher levels of irradiance without losing resolution in the z direction. The current layer may be cured at a high energy level without excessive overcuring of previously rendered layers. The use of higher levels of light energy in this way may increase implant green strength.

To further reduce the depth of penetration of light, the amount of dye in the resin may be increased. However, it may also be necessary to increase the amount of initiator present as the amount of dye is increased. Thus, the dye and initiator form a "dye-initiator package" because the amount of each included in the resin would depend upon the amount of the other. In some embodiments, other wavelengths of initiator, light source, or dye could be used.

In one embodiment, the dye concentration in the resin is between 1-5% by weight to reduce the depth of penetration of light to approximately 120 micrometers with 50 micrometer layers and 70 micrometers of overcuring to previously rendered layers. In another embodiment, the dye concentration in the resin is between 0.01 and 0.2% by weight in the resin. In another embodiment, the dye concentration in the resin is between 0.2 and 0.5% by weight in the resin. In yet another embodiment, the dye concentration in the resin is lower than 0.01% or higher than 5% by weight. In one embodiment, overcuring of previous layers is selected to be in the range of between 10% and 300%.

Separation Force and Inter-Layer Green Strength Measurements for Determining Manufacturing Process Reliability Provided herein are methods for determining the reliability of additive manufacturing processes when making three-dimensional object using continuous digital light processing (cDLP).

Thus in one aspect, a method for optimizing an additive manufacturing process for the production of a three-dimensional object using an additive manufacturing device is provided, the method comprising:

evaluating inter-layer green strength for two layers of a build;

evaluating forces acting on the build during the additive manufacturing process;

comparing the inter-layer green strength to the forces acting on the build; and altering one or more process parameters of the additive manufacturing process when the forces acting on the build are greater than the inter-layer green strength.

In some embodiment, the forces acting on the build comprise one or more of stretching of the build, torsion of the build, shrinking of the build, compression of the build, elongation of the build, adhesion of the build, or any combination thereof. In some embodiments, altering one or more process parameters comprises changing the orientation of the build with respect to the additive manufacturing device. In some embodiments, changing the orientation of the build comprises selecting a new orientation wherein the forces acting on the build are less than the inter-layer green strength. In some embodiments, altering one or more process parameters comprises selecting a different additive manufacturing device for production of the three-dimensional object. In some embodiments, altering one or more process parameters comprises modifying structural elements of the build. In some embodiments, modifying structural elements of the build comprises increasing cross-sectional overlap between the two layers of the build. In some embodiments, modifying structural elements of the build increases the inter-layer green strength such that it is greater than the forces acting on the build during the additive manufacturing process.

In some embodiments, wherein altering one or more process parameters comprises altering a material used to form the build during the additive manufacturing process. the material used to form the build during the additive manufacturing process comprises a light polymerizable material, and wherein altering the material comprises selecting a different light polymerizable material. In some embodiments, the different light polymerizable material exhibits different rheological properties than the material used to form the build during the additive manufacturing process. In some embodiments, the material used to form the build during the additive manufacturing process comprises a light polymerizable material, and wherein altering one or more process parameters comprises altering incident energy applied to the light polymerizable material to induce cross-linking. In some embodiments, altering incident energy comprises varying a wavelength of incident light, varying an intensity of incident light, varying a duration of incident light, or any combination thereof.

In some embodiments, evaluating inter-layer green strength for two layers of the build comprises measuring the inter-layer green strength. evaluating inter-layer green strength for two layers of the build comprises modeling the inter-layer green strength. In some embodiments, modeling the inter-layer green strength comprises computational modeling. In some embodiments, modeling the inter-layer green strength comprises measuring the inter-layer green strength of a model of the build.

In some embodiments, evaluating forces acting on the build comprises measuring forces acting on the build during the manufacturing process. In some embodiments, evaluating forces acting on the build comprises modeling the forces acting on the build. In some embodiments, modeling the forces acting on the build comprises computation modeling. In some embodiments, modeling the forces acting on the build comprises measuring forces acting on a model of the build. In some embodiments, the model of the build further comprises internal force sensors.

In another aspect, a method for optimizing the manufacture of a layer of an object using an additive manufacturing process is provided, wherein the object is subjected to one or more forces during its manufacture, the method comprising:
  (a) determining the inter-layer green strength of the layer;
  (b) determining each quantity of force applied to the layer as the object is built layer-by-layer;
  (c) comparing the inter-layer green strength to each quantity of force experience by the layer at any point of the manufacturing process;
  wherein if a quantity of force applied is greater than the inter-layer green strength, the design of the structure of the layer is modified to increase cross-sectional overlap of layer with one or more adjacent layers.

In another aspect, a method for optimizing the manufacture of a layer of an object using an additive manufacturing process, wherein the object is composed of a material, and wherein the object is subjected to one or more forces during its manufacture, the method comprising:
  (a) determining the inter-layer green strength of the layer;
  (b) determining each quantity of force applied to the layer as the object is built layer-by-layer;
  (c) comparing the inter-layer green strength to each quantity of force experience by the layer at any point of the manufacturing process;
  wherein if a quantity of force applied is greater than the inter-layer green strength, the manufacture of the object is modified to replace the material from which it is composed with a second material that has an inter-layer green strength greater than any quantity of force applied to the layer.

In another aspect, a method for selecting between a first orientation and a second orientation for manufacturing an object using an additive manufacturing process, wherein the object is manufactured in the first orientation out of a first plurality of layers and in the second orientation out of a second plurality of layers, and wherein the object is subjected to one or more forces during its manufacture, the method comprising:
  (a) determining the ratio of an average of the force applied to each layer of the first plurality of layers to the average of the inter-layer green strength of each layer of the first plurality of layers to provide a first force to green strength ratio;
  (b) determining ratio of an average of the force applied to each layer of the second plurality of layers to the average of the inter-layer green strength of each layer of the second plurality of layers to provide a second force to green strength ratio;
  (c) comparing the first force to green strength ratio to the second force to green strength ratio; and
  (d) selecting the orientation for manufacture that is associated with the lesser of the first force to green strength ratio and the second force to green strength ratio.

In some embodiments, the additive manufacturing process is selected from a material extrusion process, a powder bed fusion process, a binder jetting process, a stereolithography process, a computed axial lithography process, a liquid additive manufacturing process, or a directed energy deposition (DED) process. In some embodiments, the additive manufacturing process is continuous digital processing (cDLP).

In some embodiments, the force applied to the object is a separation force.

In some embodiments, the object is manufactured from a resin composition comprising a liquid light-curable material and a photoinitiator.

In some embodiments, the separation force of a layer is determined by:
  (a) providing an additive manufacturing apparatus including a Digital Micromirror Device (DMD), a transparent or translucent basement plate, and a build plate operatively coupled to a force sensor;
  (b) depositing an amount of the resin composition above the basement plate;
  (c) actuating the DMD to expose a portion of the resin composition to light to at least partially crosslink the liquid light-curable polymerizable material therein to form the layer of the three-dimensional object;
  (d) actuating the build plate or the basement plate to increase the distance between the build plate and the basement plate such that the layer of the three-dimensional object is separated from the basement plate;
  (e) measuring the separation force required to separate the layer of the three-dimensional object from the basement plate with the force sensor during step (d).

In some embodiments, the inter-layer green strength of the material is determined by:
  (a) providing an additive manufacturing apparatus including a Digital Micromirror Device (DMD), a transparent or translucent basement plate, and a build plate operatively coupled to a force sensor;

(b) depositing an amount of the resin composition above the basement plate;

(c) actuating the DMD to expose a portion of the resin composition to light to at least partially crosslink the liquid light-curable polymerizable material therein to form the first layer having a first cross-sectional area;

(d) actuating the build plate or the transparent or translucent basement plate to increase the distance between the build plate and the basement plate to separate the first layer from the basement plate;

(e) actuating the DMD to expose an additional portion of the resin composition to light to at least partially crosslink the liquid light-curable polymerizable material to form a second layer having a second cross-sectional area and to at least partially overcure at least some of the first layer to the second layer to cause at least some interlayer binding between the first layer and the second layer, wherein the second cross-sectional area is greater than the first cross-section area;

(f) actuating the build plate or the basement plate to separate the second from the basement plate, wherein the force sensor measures the separation force required to separate the second layer from the basement plate;

(g) measuring the separation force required to separate the second layer from the basement plate with the force sensor during step (f);

(h) repeating steps (e), (f) and (g) to form one or more additional layers have one or more additional cross-sectional areas until there is a failure of the interlayer binding of any two of the layers upon actuation of the build plate or basement plate, wherein each additional cross-sectional area is greater than the cross-sectional area of the previous layer;

(i) calculating the inter-layer green strength by dividing the separation force measured for the most recent additional layer manufactured during step (h) upon failure of interlayer binding by the additional cross-sectional area of the most recent additional layer.

In another aspect, a method for optimizing the manufacture of a layer of an object using continuous digital light processing (cDLP), wherein the layer has a cross-sectional area, and wherein the object is composed of a material manufactured from a resin composition comprising a liquid light-curable polymer and a photoinitiator, the method comprising:

(a) measuring the separation force for a test layer having substantially the same cross-sectional area as the layer of the three-dimensional object using the method described above;

(b) measuring the inter-layer green strength of the material using the method described above;

(c) calculating the probability of structural failure of the layer by comparing the separation force of the test layer with the inter-layer green force of the material, wherein if the separation force of the test layer is greater than the inter-layer green force of the material, the resin composition is modified.

In another aspect, a method for optimizing the manufacture of a layer of a three-dimensional object using continuous digital light processing (cDLP), wherein the layer has a cross-sectional area, and wherein the object is composed of a material manufactured from a resin composition comprising a liquid light-curable polymer and a photoinitiator, the method comprising:

(a) measuring the separation force for a test layer having substantially the same cross-sectional area as the layer of the three-dimensional object using the method described above;

(b) measuring the inter-layer green strength of the material using the method described above;

(c) calculating the probability of structural failure of the layer by comparing the separation force of the test layer with the inter-layer green force of the material, wherein if the separation force of the test layer is greater than the inter-layer green force of the material, the structure of the layer of the three-dimensional object such that cross-sectional overlap between the layer and one or more adjacent layers is increased.

Reliability is defined as the probability that an item will perform a required function without failure under stated conditions for a specified period of time ("Introduction to Reliability Engineering" 2011). Uncertainties are a central element when a new process or material is being developed. For instance, a new material, from which some component will be made, presents a wide range of its properties. Dynamic properties or time-dependent properties such as fatigue, fracture toughness, creep, and so on the variation can be even wider. In addition to the variation in the basic material properties, there will be further variations due to variation of the manufacturing process itself. Absolute dimensional accuracy within specified tolerances are a necessary feature of all manufactured products (Carter 1986). Dimensional accuracy can be affected by shrinkage, swelling, and residual stress.

The main sources of uncertainty in cDLP are associated with the variability of the process itself and the resins material properties. The paramount parameters selected for the present research were separation force and green strength. The failure of the printed part can be due to either of those parameters. It must be highlighted that, although both separation force and green strength have been represented by approximately normal distributions, in the real world their distributions will often be far from normal. Essentially, a failure will occur when the separation force to which a printed part is subjected is greater than the green strength. Because a part is weak does not imply that it will fail; it may never encounter a separation force which is greater than its green strength.

Previous attempts have been made to correlate the parameters described herein with the process failure during additive manufacturing via cDLP. Huang and Jiang monitored the separation force during the printing of solid parts using cDLP. A superelastic film of silicone was used to coat the bottom surface of the vat in order to reduce the separation force. Experiments with different film thickness were carried out. Using an exposure time of two minutes, a considerable reduction in the separation force was found as the film thickness increased (Y.-M. Huang and Jiang 2005). Additionally, the authors printed different solid geometries, and they concluded that the shape only affects the tendency curve of separation force. Kovalenko et al. reported an in-situ process monitoring for a cDLP with the objective to implement a linear feedback control system to predict the faults during the printing process of solid parts. They suggested an algorithm based on the computation of a minimum and maximum theoretical force and the comparison with the actual separation force measure of a load sensor. This method would avoid the failure during the printing process (Kovalenko et al. 2017). Zhou et al. reported a multi-material cDLP system named two-channel. This technology separates the bottom surface of the vat into two sections, with and without a PDMS film. An additional horizontal (x-axis) movement helps to reduce the separation force. However, a shear force is applied in the x-direction, and some parts could fail (Zhou et al. 2013).

The literature reports a few experiments that have been carried out to study the influence of the different variables and parameters related to cDLP process with biodegradable resins. The increase of separation velocity favors printing failure due to an increment of the separation force (Wu et al. 2017). Pan et al. measured the separation force varying the separation velocity and the thickness of the PDMS film. The separation force rises with the separation velocity; by increasing the thickness of the PDMS film, the separation force is decreased (Pan et al. 2017).

Precise control over the depth of curing of the resin is fundamental when manufacturing high-resolution porous structures by cDLP. For a given resin, the cure depth is determined by the light energy to which the photo resin is exposed. This energy can be adjusted by varying the exposure time or by regulating the light intensity (van Bochove et al. 2016). To allow accurate processing by cDLP, the viscosity of the photo-curable resin needs to be sufficiently low to warrant flow and adequate spread of the resin during the manufacturing of a part. van Bochove et al claim that while reactive diluents such N-vinyl pyrrolidone or DEF could be employed to reduce the viscosity of the resin, its use would lead to high concentrations of non-degradable polymeric chains (van Bochove et al. 2016). This aspect is critical in the manufacturing of medical devices and implants that are intended to be biodegradable. The reduction of the viscosity is led by the mixture of the pure PPF with the diluent DEF. High amounts of DEF changes the cross-linking mesh structure reducing rigidity (Dean et al. 2012), and producing diluent-swollen photo-cross-linked structures during the building process (van Bochove et al. 2016).

It is particularly challenging in using photo-curable resins in the preparation of porous structures by cDLP where mechanical (sticking) forces on the object being built are high. The stacked photo-polymerized resin layers not only need to be sufficiently strong to maintain adherence to each other during the building process but also the photo-polymerized layers need to separate from the bottom of the reservoir without failures while the structure is printed.

Pan et al. measured the separation force for regular porous structures with the same printing area. They found that the separation force increases with the degree of porosity of the print geometry (Pan et al. 2017). However, to establish a relationship between separation force and porosity is very complicated. Analyzing the results of these authors, we found that the area-perimeter ratio has an influence on the separation force and the strength of the printed part. That is, when the area-perimeter ratio decreases, the separation force increases, leading to failure of the part during its fabrication. Zhou et al. used cDLP to print different solid projection patterns with the same area. The tendency again is a reduction in the area-perimeter ratio as the separation force increases (Zhou et al. 2013).

Van Bochove et al. presented a method to optimize the construction of a highly porous structure with the shape of a meniscus using cDLP. The resin used was poly(trimethylene carbonate). The pore geometry was a structure had a TPMS shape with a porosity of 60% and a pore size of 630 µm. They found that pores smaller than 600 µm will lead to over-curing of the relatively viscous resin and inadvertent closing of pores, they concluded that the pores should be relatively large. They also found that manufacturing complex and large structures was more difficult than building designed porous cylinders with a similar pore network characteristic. They concluded that even though they used an optimized resin formulation in the building of meniscus implants, failed builds preparing these complex structures occurred very frequently, probably influenced by the high molecular weight of the photopolymer used (van Bochove et al. 2016).

Some approaches have been considered to reduce separation force. For example, an oxygen-inhibited free-radical photopolymerization method. This technique uses a film on the bottom surface of the vat that permits the oxygen permeability. However, this technology has certain restrictions on material type and viscosity (Lian et al. 2017).

The approach of reliability in the manufacturing of PPF parts with cDLP as described herein provides an initial point to reduce the failure rates, especially when complicated or porous geometries are intended to be built. The term reliability is used to express a certain degree of assurance that a device or system will operate successfully in a specified environment during a specific time. This study was focused on the study of two variables, the separation force, and the interlayer green strength, associated with the manufacturing process and material properties, respectively. Different models may be necessary for different failure mechanisms. However, these two parameters are now available for design and both correlate closely with surface area and molecular weight.

Tissue Engineering Scaffolds

A scaffold design may include an external shape that accurately fits a patient-specific defect site. Moreover, the design may require complex three-dimensional structures.

In some embodiments, the scaffold includes pores that are orthogonal or at right angles with the layers of the scaffold. The three-dimensional geometry of scaffolds including internal spaces may be important to the loading of cells and the establishment of vascular channels. In one embodiment, a scaffold includes pores or internal channels. In one embodiment, the diameter of pores and channels in the scaffold is between 150 micrometers and 1 millimeter. In another embodiment, the diameter of pores and channels in the scaffold is between 50 micrometers and 1.6 millimeters. In other embodiments, the diameter of pores and channels in the scaffold is smaller than 50 micrometers or larger than 1.6 millimeters. Modeling of scaffold pores at these ranges may require compensation in the CAD to correct for, among other factors, post-curing shrinkage of implants or swelling due to wetting caused by pre-implantation cell culturing or implantation itself.

In addition to the scaffold design parameters relating to pore size, the design may require complex porous structures that facilitate cell loading, neotissue growth, and host tissue ingrowth. For example, the design may require that pores or channels open toward the host tissue in the defect site to allow tissue ingrowth prior to the implant's full degradation. More accurate rendering makes it more likely that complex internal pore structures can be created.

In some embodiments, the scaffold includes pores that are oblique. Oblique is defined to be any direction that is not parallel to the x, y, and z directions by which scaffolds are rendered using the above described additive manufacturing techniques. Oblique construction may be important to make sure that the host's tissues do not encounter a wall (barrier) in the scaffold, which is more likely when pore structures are built orthogonally than when pores and/or channels are oriented towards the host tissue. The implant designer may want to orient pores and/or channels within a scaffold so that they open toward the host's tissue thereby facilitating growth of new tissue into the implant and active incorporation of the implant into the host's tissues.

Additive manufacturing devices with voxel resolution in the range of 100-1000 micrometers may be able to bring about orthogonally oriented pore structures, however they may provide insufficient resolution to produce obliquely oriented pores in these ranges. Resolution of the cDLP device is such that rendering of structures having obliquely oriented pores is possible.

Additionally, in tissue engineering scaffold applications where an initial goal is cell attachment, PPF's hydrophobic surface can be modified through radiofrequency glow-discharge (RFGD) or by soaking the implant in serum to provide for protein adsorption. Cell attachment can also be mediated by other factors embedded in the surface that mimic extracellular matrix components. This includes surface roughness, which may include indentations and protrusions having diameters ranging from 1 nanometer to 100 micrometers, as well as the material's compliance.

Once attached, the goal is likely to shift to cell proliferation and eventually maturation as host tissue integrates. In addition to the effect the dye has on surface roughness, other compounds, such as tricalcium phosphate crystals, can be added to the resin in the additive manufacturing device. However, as with the dye, depending on solubility, crystal size, and tendency to aggregate, it may be difficult to keep these crystals suspended in the resin at a relatively constant concentration throughout the scaffold rendering process.

Scaffold design features, such as wall thickness, affect the macro strain distribution and may be optimized to resist trauma. Moreover, it may be necessary to counterbalance desired resorption processes with the need for the implant to be loaded during tissue regeneration. The need to localize strain-bearing portions of a scaffold may necessitate the consideration of regions lacking porosity or regions rendered with composite materials, some of which may not degrade.

Final part accuracy may be dependent upon thorough part cleaning post rendering. This may be necessary to remove any residual uncured resin which would crosslink post rendering. The choice of washing procedures in turn relies on the mechanical integrity of the resin as cured by the cDLP process or green strength. Parts which are accurately rendered but remain soft may become damaged by improper handling or the use of harsh solvents. Once cleaned, final part strength may be improved by post-curing in a UV bath.

Engineered Bone Tissue Grafts

Recent interest in bioengineered scaffolds has inspired increased research in scaffold materials. They are being tested to see if they can achieve better results in the three categories mentioned. Other than the possibilities that new materials bring to the table, their architectural properties, such as porosity, cellular seeding capacity, growth factor seeding capacity, and fabrication options make for a virtually limitless range of possibilities (Langer and Vacanti 1993; P. X. Ma et al. 2001; Pangborn and Athanasiou 2005). With the addition of additive manufacturing (AM), there's even more possibilities in scaffold creating. All designs become possible, with the ability to create free-form porous scaffolds with custom tailored architectures (Giannitelli et al. 2015a). Depending on the mechanism they are based for working, they can be classified either into nozzle or laser-based printing systems (Hollister 2005a). Nozzle or extrusion-based 3D printers are based on the dispensation of a filament through an orifice, be it a binding base on a powder bed or the material using an inkjet printer-based technology, while laser-based printing systems use cross-linking of polymers by photopolymerization. While these techniques allow for very complex structures, tailored as far as the computer assisted design can allow for, there is a balance that gets difficult to maintain, such as porosity to mechanical strength (Giannitelli et al. 2014). Another big factor is that the materials need to comply with strict rules such as cytotoxicity in order to be eventually used in clinical practice.

Bone tissue engineering begins as a process with the fabrication of a biologically compatible scaffold that will support living cells for their attachment, proliferation and differentiation, and consequently promote tridimensional (3D) tissue regeneration both in vitro and in vivo (Thavornyutikarn et al. 2014). Ideally, a tissue engineering scaffold should be biocompatible, biodegradable, highly porous and interconnected, and mechanically reliable. Anatomically, the structure of bone tissue varies according to the bone in question, the segment in question and its depth. Thus, the selection of shapes and the suitable biomaterials should be dictated by the anatomic site for regeneration, the mechanical loads present at the site, and the desired rate of resorption/degradation (Karageorgiou and Kaplan 2005).

Manufacturing a satisfactory biomimetic bone substitute is still a challenge in the field of BTE. For the repair and regeneration of bone tissue some known key parameters of the design have been identified and it is accepted that the scaffolds need to have a high porosity and an appropriate pore size. Karageoriou and Kaplan claim that the minimum requirement for pore size is considered around 100 µm due to cell size, migration requirements and transport (Karageorgiou and Kaplan 2005). However, pore sizes >300 µm but less than 1 mm are recommended, with the purpose of having enhanced new bone formation and the capillary growth (Dean et al. 2012). Second, the anatomically shaped matrix should be designed as an optimal guide to new bone formation allowing osteoblast migration, differentiation and osteoclast remodeling (Hollister 2005b). Third, the scaffold's rate of degradation/resorption should match the healing rate of the new tissue, and this is a function of both design, material composition and manufacture procedures (Hutmacher 2000; Choi et al. 2009; Melchels, Feijen, and Grijpma 2009). Other functional features such as surface roughness, scaffold stiffness, or hydrophilicity may be designed to affect the cells behavior (Karande, Ong, and Agrawal 2004). It is also possible to determine some features of cell response by adjusting the scaffold's polymer composition/chemistry (Dean et al. 2012).

Bone tissue engineering (BTE) provides opportunities to create functional constructs for bone tissue repair and the study of stem cell behavior and also provides models for studying numerous diseases (Nerem and Schutte 2014). Bone is the second most transplanted tissue after blood (Ibrahim 2018). Due to the risks and constraints of reconstruction of defects with foregoing-body implants, autologous bone grafts and allogeneic tissue transfer, tissue engineering provides the promise of regenerating autologous bone tissue free of limitations and morbidities associated with current treatment options (Salgado, Coutinho, and Reis 2004).

Bone is a complex tissue that has mechanical, hematopoietic, and metabolic functions (Ibrahim 2018). A definition for a natural bone is: "Bone is an electrically active polymer-ceramic hybrid composite material comprising different components e.g. inorganic (hydroxyapatite), organic (collagen), cellular (osteoblast, osteoclast, osteocytes) and water." (Basu 2017).

Anatomically, natural bone consists of cortical bone, cancellous bone and bone marrow. While cortical bone has a high mechanical strength and modulus, cancellous bone is mechanically weak. The outer cover of membrane of the bone is called periosteum, Structurally, cortical bone is synonymous with compact bone and cancellous bone, synonymous with trabeculas/spongy bone are the two osseous tissues that comprises natural bone. The major functions of cortical bone are to provide mechanical support and to protect underlying organs or internal bone structure. Cancellous bone is highly vascular and often contains bone marrow, in which blood cells are produced (Sipos, Föger-Samwald, and Pietschmann 2014).

"Critical size defect" or "large bone defect" is defined as an extensive bone loss that prevents spontaneous healing. The gap in these cases is clinically determined to be twice the diameter of the injured bone (Sela and Bab 2012). On the other hand, ASTM-F2721 defines the critical size defect as a bone defect, either naturally occurring or artificially created, which will not heal without intervention. In the clinical setting, this term applies to exceeding a healing period of approximately 6 months. BTE has been trying to generate an answer for these defects by fabrication of inserts that can integrate to the native bone and as previously mentioned, cell coated scaffolds seen to be the best bet.

A large tissue engineered construct fabricated for BTE application needs to receive sufficient nutrients and to have effective waste product removal. In static culture, cells seeded on the periphery of the 3D constructs grow readily; however, those that reside in the center of a construct tend to undergo necrosis (Haj and Cartmell 2010).

Perhaps the most exciting potential of additive manufacturing in BTE is the effort to create biological scaffolds for cell seeding, which lays the foundation for the development of bone organ printing in the future (Cheng et al. 2017). Additive manufacturing presents a new frontier for complex designs that were previously impossible to create. The resolution they provide has proven to affect cell adhesion, as well as migration, proliferation and differentiation (Giannitelli et al. 2015a). This becomes a limiting factor, because the Nano metric features are needed to better mimic the native extracellular matrix and some macroscopic aspects of the design such as pore size, distribution and design seem to affect tissue growth and migration as well as vascularization (Holzapfel et al. 2013a). Different processes, biomaterials, and their combinations could be used to obtain potential clinical applications.

The combination of additive manufacturing with other conventional scaffold fabrication methods emerges as a new promising procedure (Giannitelli et al. 2015b). Also, different materials can be combined into porous structures to exploit the inherent properties of each of them, converging different technologies to build a single microarchitecture can represent an effective path to overcome disadvantages of the simple techniques. For instance, BTE approach is an inherently sound strategy for regenerating the hierarchical structures of the periodontium, given its complexity, whereby periodontal tissues would be constructed in the laboratory under controlled conditions and then surgically implanted (Ivanovski et al. 2014).

Some advanced additive manufacturing processes, like continuous Digital Light Processing (DLP), have gained popularity in BTE applications for its high precision, reproducibility, and controllable pore structure. Another consideration for BTE constructs is nutrient transport and waste removal from the scaffold's interior. Critical to the problem of nutrient transport within the scaffold is scaffold porosity and permeability. Without flow transport within the scaffold is mainly a function of diffusion, careful design of the diffusion characteristics of the scaffold is critical (Karande, Ong, and Agrawal 2004). Several studies have emphasized the need for high porosity and a high surface-area-to-mass ratio for ensuring uniform cell seeding, nutrient delivery, and tissue ingrowth. A representative structure with unique mechanical and fluid transport characteristics is Schoen's gyroid structure, a non-intersecting, triply periodic minimal surface. The main advantage of triply periodic minimal surface scaffold pore geometry is the reduced resistance to flow, considered to facilitate cell seeding, migration, waste products removal, and nutrient delivery. The gyroid may also preserve a high degree of structural stiffness (Walker et al. 2017). The existence of minimal surface geometries in in-vivo biological tissue is considered a sign that this is an optimum design.

The role of computer-aided and digital manufacturing of scaffolding techniques has been extensively studied in recent years. Since complex 3D structures can be produced directly from a CAD model, additive manufacturing methods provide exceptional spatial control over the architecture of fabricated scaffolds.

Direct Perfusion Bioreactor for Tissue Engineering Applications

In another aspect, systems and methods are provided for culturing cells within (e.g., porous) tissue engineering scaffolds by continuous flow processes.

Thus, in one aspect, a direct perfusion bioreactor system for three-dimensional tissue culture of a tissue engineering scaffolds is provided comprising:

At least one perfusion chamber for housing the tissue engineering scaffold having a chamber flow inlet and a chamber flow outlet;

An in-line peristaltic pump having a pump flow inlet and a pump flow outlet;

a culture medium reservoir having a reservoir flow inlet and a reservoir flow outlet;

wherein the pump flow outlet is in fluid communication with the chamber flow inlet;

wherein the chamber flow outlet is in fluid communication with the reservoir flow inlet; and wherein the reservoir flow outlet is in fluid communication with the pump flow inlet.

In some embodiments, the perfusion chamber is composed of a disposable material. In some embodiments, the perfusion chamber is composed of a syringe. In other embodiments, the perfusion chamber is composed of soft tubing. In some embodiments, the perfusion chamber is composed to soft tubing that is subjected to an external pressure to conform to the shape of the tissue engineering scaffold housed within the tissue engineering scaffold. In some embodiments, the bioreactor may comprise two or more perfusion chambers. In some embodiments, the tissue engineering scaffold is held in place within the at least one perfusion chamber by a pair of conical springs.

In another embodiment, a method for culturing cells in a tissue engineering scaffold is provided comprising:
(a) providing a direct perfusion bioreactor as described herein;
(b) placing a tissue engineering scaffold into the perfusion chamber of the bioreactor;
(c) placing a culture medium comprising a plurality of cells and optionally one or more nutrients or growth factors into the culture medium reservoir of the bioreactor; and (d) circulating by action of the peristaltic pump the culture medium from the culture medium reservoir through the perfusion chamber until at least some of the plurality of cells in the culture medium have implanted on the tissue engineering scaffold.

In some cases, these methods and/or chambers can (i) successfully split lines of nutrients and growth factors to cells; (ii) support custom shaped bioreactor which predictable CFD so that guarantee of flow through center of tissue engineering scaffold at similar or same rate as rest of tissue engineering scaffold, not quickly around the tissue engineering scaffold due to poorly fitting chamber; (iii) place the pump outside incubator chamber with high $CO_2$ and high humidity so pump doesn't corrode; (iv) maintain the bioreactor and media reservoir inside incubator; or any combination thereof.

A bioreactor can be defined as a device that uses mechanical means to influence biological processes under strictly monitored operating conditions. In bone tissue engineering (BTE) bioreactors can be used to aid in the in vitro development of a new bone tissue. The main reason to use bioreactors is to deliver nutrients and/or grow factors, and to remove waste products. Secondary functions are providing biochemical and physical regulatory signals to cells and stimulating them to undergo differentiation and/or to produce extracellular matrix before in vivo implantation (Rosser and Thomas 2018).

For BTE purposes, dynamic culture bioreactors, such as spinner flasks, rotating wall bioreactors, and flow perfusion systems, have shown promising results. In general, dynamic culture produces a much more homogeneous distribution of cells and matrix, while systems enabling shear stress applied by the medium flow may stimulate the cells to proliferate and differentiate. Furthermore, these systems enhance mass transport, ensuring continuous nutrition of cells, and removal of waste products (Gardel et al. 2014).

BTE researchers are interested in studying how to design of a perfusion bioreactor that can influence cell culture. Therefore, the optimal operating conditions of a bioreactor should not be determined through a trial and error approach but should be instead defined by integrating experimental data and computational models (Wendt et al. 2009).

Bioreactors that use a pump system to perfuse media directly through a scaffold are known as perfusion bioreactors (Yeatts and Fisher 2011). Many different perfusion bioreactor systems have been developed but most systems consist of a similar basic design consisting of a media reservoir, a pump, a tubing circuit, and a perfusion chamber. Perfusion bioreactors can be used for cell seeding and/or cell culture protocols. Perfusion bioreactors are typically classified into indirect or direct systems, depending on whether the culture medium is perfused around or throughout the scaffolds/grafts (Sladkova and de Peppo 2014).

In indirect perfusion bioreactors, the scaffold/graft are loosely placed in the perfusion chamber, and the culture medium preferentially follows the path of least resistance around the constructs, resulting unpredictable mass transfer in central regions. In direct perfusion bioreactors, the scaffold/construct are placed into the perfusion chamber in a press-fit manner so that the culture medium is forced to pass through the pores of the constructs. Direct perfusion bioreactors are suitable to treat large skeletal defects. However, obtaining this level of sealing, so that media cannot flow around is challenging. The perfusion chamber must be custom made to fit a scaffold/graft tightly, and the scaffold/graft must be highly interconnected pores (Yeatts and Fisher 2011). Despite these difficulties, many perfusion bioreactor systems have been developed and tested for bone tissue engineering experiments.

Perfusion bioreactors employ circulatory flow throughout the system with a singular input and output to provide sufficient nutrient transfer, removal of waste products, and application of mechanical stimuli. To establish such a system, three major components have been identified by review of literature: the culture encasing bioreactor chamber, a vessel containing the oxygenated nutrient-rich medium, and a pump capable of generating flow through the system.

Flow phenomena occurring within the bioreactor are approximated by solution of the Navier-Stokes equations for the applicable boundary conditions in conjunction with the Continuity equation. The Navier-Stokes and Continuity equations represent the conservation of momentum and mass, respectively.

By way of non-limiting illustration, examples of certain embodiments of the present disclosure are given below.

EXPERIMENTAL EXAMPLES

Example 1. Mechanical Reliability Approach of Continuous Digital Light Processing (cDLP) of Poly(Propylene) Fumarate (PPF) Scaffolds Materials and Methods An overview of the separation force experiment and green strength is present in FIG. 1.

Calibration of the cDLP Process

A typical calibration of the cDLP process consists of the next steps suggested by Dean et al. (2012):
1) Perform cure tests to determine parameters that result in a desirable cure (Z direction) depth of polymerization (Mott et al. 2016).
2) Assure that the material formulation determined in step 1 will result in useful scaffolds.
3) Develop strategy for the attachment to the build plate, which may require manual transfer of initial burn-in layers.
4) Transfer CAD design file to cDLP device, including any support structures.
5) Render test scaffolds and evaluate accuracy.
6) Perform experiments to analyze scaffold functional properties.

PPF Resin Formulation

Specimens for the experiments were fabricated using a poly(propylene fumarate) (PPF)-based resin was characterized according to specifications by Mott et al. (2016). PPF resin was diluted with diethyl fumarate (DEF, Sigma-Aldrich, St. Louis, MO) in a 1:1 ratio in order to reduce the viscosity for 3D cDLP process. Photoinitiators Phenyl bis (2,4,6-trimethylbenzoyl)-phosphine oxide (BAPO, Sigma-Aldrich, St. Louis, MO) and bis[2,6-difluoro-3-(1-hydropyrrol-1-yl)phenyl]titanocene (Irgacure 784, BASF, Ludwigshafen, Germany) were added in concentration of 3 and 0.4% by mass, respectively. Finally, 0.7% of 2-Hydroxy-4-methoxybenzophenone (HMB, Sigma-Aldrich) was added to mitigate light scattering within layers. Seven batches were prepared using PPF of different average molecular weight (MWavg), namely R1 (1800 Da), R2 (1600 Da), R3 (1100 Da), R4 (1200 Da), R5 (1600 Da), R6 (1200 Da) and R7 (1900 Da). The resin was calibrated by cure tests with a 150 μm cure depth.

PPF Resin Viscosity

The dynamic (absolute) viscosity of seven different batches of PPF were measured using a falling ball viscometer (Barnant GV2100, Thermo Fisher Scientific, Waltham, MA, USA). The resins were warmed to 45° C. and the viscosity readings were conducted immediately. The temperature of 45° C. was used as this is the initial temperature of the PPF resins during our 3D printing experiments. The room temperature and the relative humidity during the experiments were 25° C. and ~35%, respectively.

Cure Depth

The depth of penetration of the light and the critical energy at photoinitiation are important parameters that must be controlled during cDLP 3D printing fabrication. Polymerization takes place when the energy to which the resin is exposed is greater than the photo initiator's critical energy (Jacobs 1992). Otherwise, no polymerization occurs. The energy delivered on the resin surface ($E_{max}$) penetrates into the resin. The energy inside the solution at depth (z), $E_{max}$ and the cure depth ($C_d$) are related by Beer-Lambert law (Sun et al. 2005) as described follow:

$$C_d = z \cdot E_{max}$$

In the case of PPF resins, Mott et al. (2016) suggest a cure depth (Cd) between 120 and 150 μm based on their experience and manufacturer recommendation. This range of cure depths allows for 70-100 μm of overcure, when printing at 50 μm/layer, such that adequate layer-layer lamination (interlayer cross linkage) occurs.

Figure 2:
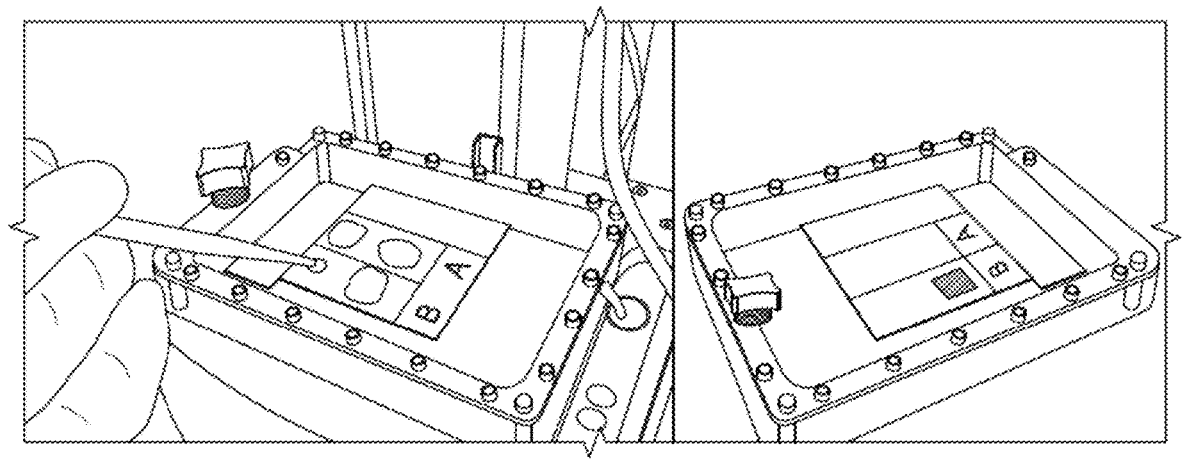
FIG. 2 are photographs demonstrating the procedure for estimating $C_d$. Four layers were cured in each run at exposure times of 30, 60, 90 and 120 seconds.

In order to carry out this experiment, squares of 1 cm² area were designed for the mask projection. A commercial cDLP machine (Perfactory picro, EnvisionTEC®, Inc., Dearbon, MI, USA) was used. Two slides were placed on the bottom surface of the vat. Using a 3 mL transfer-pipet, three to five drops of the resin being tested were placed in four different regions (2/slide) as FIG. 2 shows. Each region was used to cure the resin at a different exposure time, e.g., 30, 60, 90 and 120 s. Four randomized replicates were carried out for each exposure time. Then the curing test was initiated. After the curing test was complete, the slides were removed and covered with one slide each forming a sandwich in order to measure $C_d$ accurately. Using a digital caliper (Digimatic Series 500 digital, Miyutoyo, Kawasaki, Japan), the thickness of the cured-test samples was measured. The thickness of the two slides are subtracted from the cure test measurement to determine cure depth ($C_d$).

Experimental Setup for Separation Force

Figure 3:
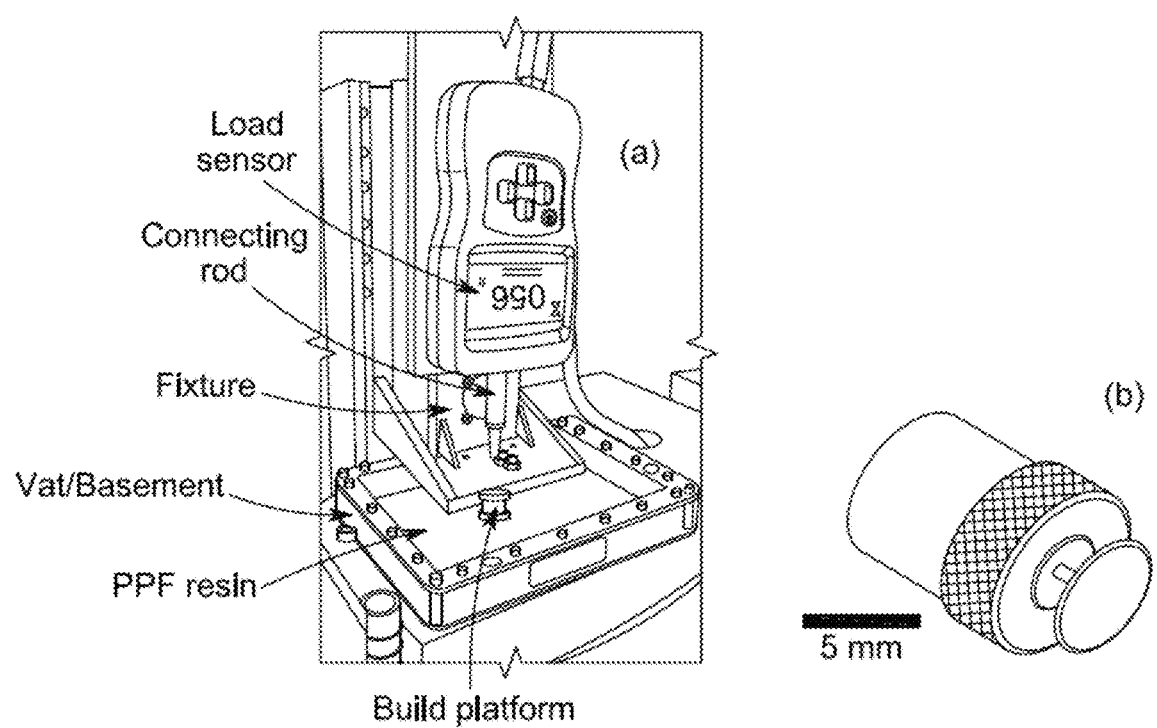
FIG. 3 are photographs depicting the separation force measurement experimental setup (a) and the build platform (b). For the experiments, the test specimens were adapted to a circular build platform of 12 mm diameter to avoid any effect of the moment due to eccentricity.

The Perfactory picro (EnvisionTEC®, Inc., Dearbon, MI, USA) is used to test separation force. The irradiation intensity in all experiments is set at 350 W/dm². The resin container is coated with a 2 mm-thick PDMS film. A calibrated digital force gauge (FG-3003, Shimpo Instruments Inc., Glendale Heights, IL, USA) is mounted directly on the build platform to measure the force during the overall printing process FIG. 3). Data acquisition software (EDMS, Shimpo Instruments Inc., Glendale Heights, IL, USA) is used to collecting the data from the sensor. The sample rate is set at 10 samples/s. In this experiment, the separation force and the breaking load under different cross-sectional areas is monitored and recorded. For all experiments, the separation (pulling-up) velocity is fixed to 1 mm/s.

Figure 4:
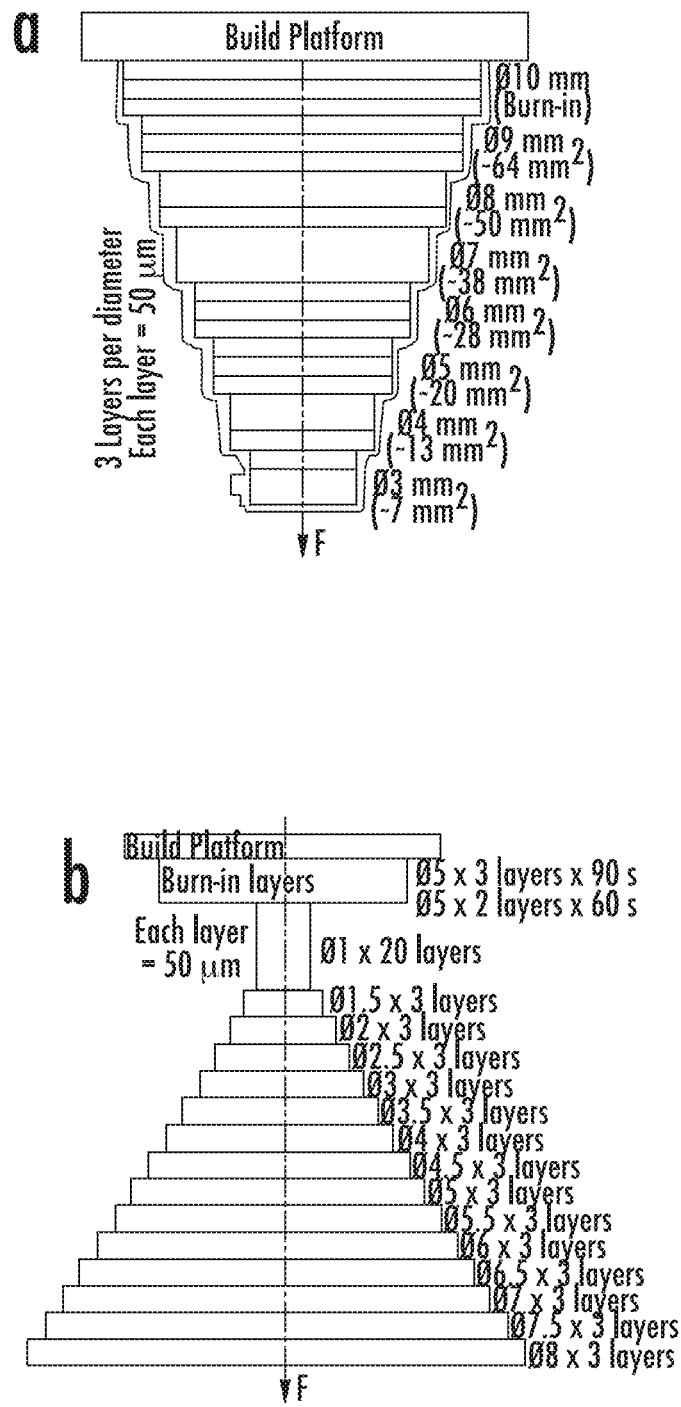
FIG. 4 depicts (a) a depiction of the separation force experiment specimen; (b) a depiction of the breaking load/inter-layer green experiment specimen; (c) a chart of the separation force data collected; and (d) a chart of the breaking load data collected.
Figure 4:
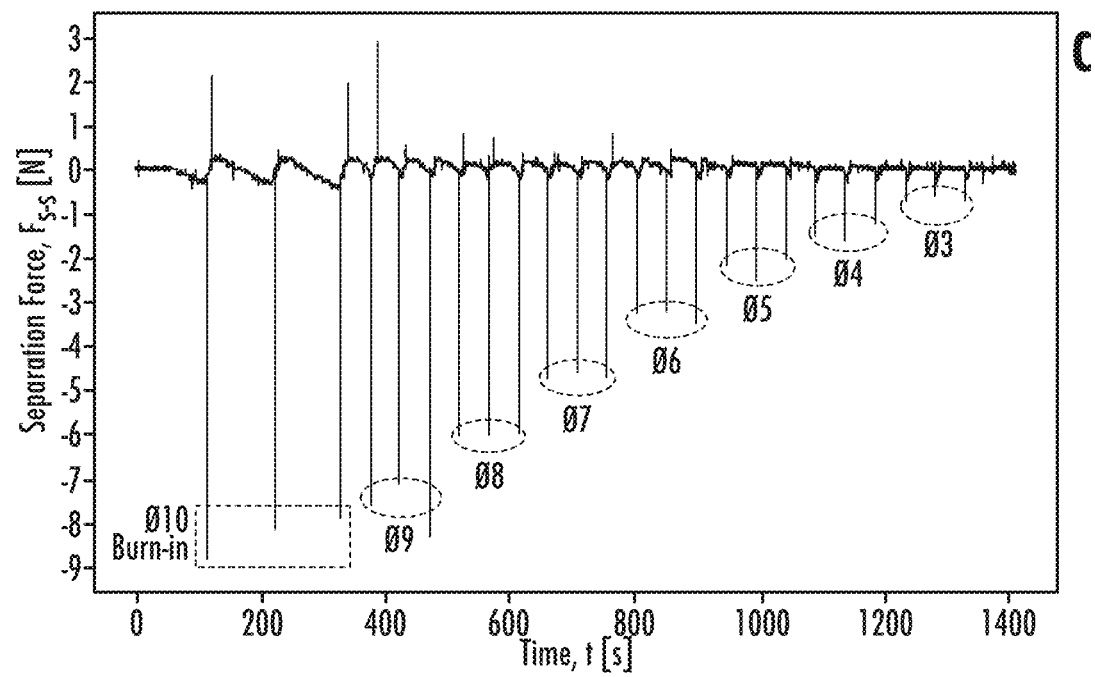
Figure 4:
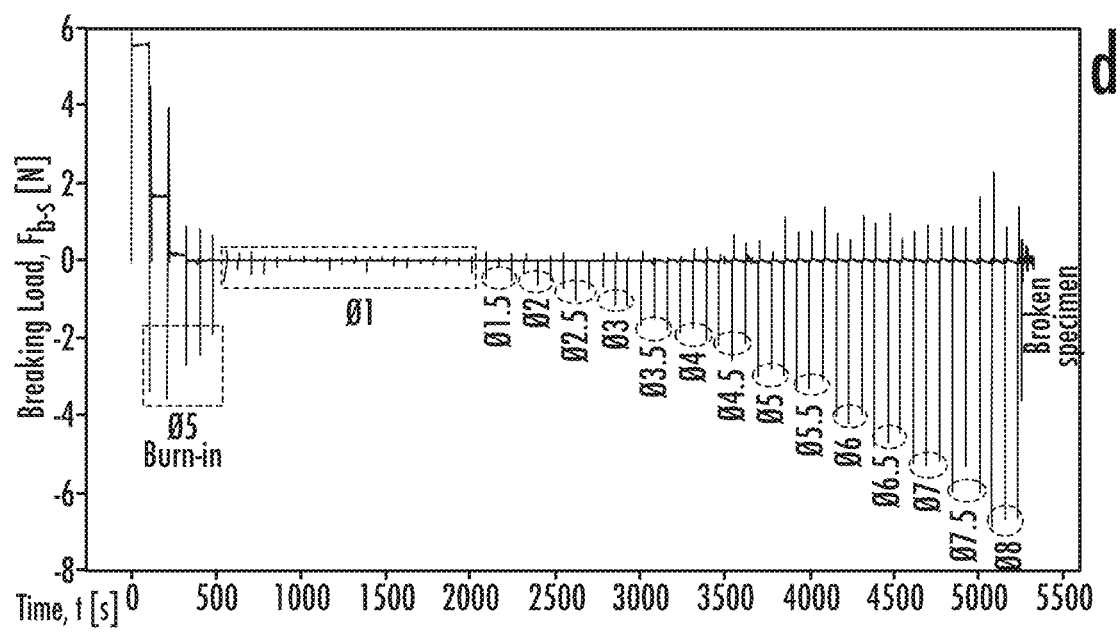

FIGS. 4 (a) and (b) show the specimens used to determine separation force and the load experiment, respectively. The specimens are stepped solid cylinders with incremented diameters. These shapes were designed using SolidWorks CAD software (SolidWorks Corp., Dassault Systemes, Concord, MA, USA).

In the building process, the first 3 layers were used as burn-in layers (90s of exposure time). The function of these layers is to fully coat the elevator in order to achieve a strong attachment between the part and the build platform.

Separation Force of Regular Shapes. As shown on FIG. 4 (a), the diameters for each successive step green strength test part in this experiment were 9, 8, 7, 6, 5, 4 and 3 mm. Their correspondent cross-sectional areas are 64, 50, 38, 28, 20, 13 and 7 mm². Each step is formed by 3 layers (50 μm each). Four different PPF resins (R1, R3, R5 and R7) were used to conduct the separation force experiment. Throughout the build process, separation force occurs after in every layer is cured. The completeness and accuracy of the cured layer being peeled off the basement influences the precision of the next layer and all subsequent layers. An inaccurate peel will cause the part to fail. The relationship between layer area and separation force as well as the green strength of all previous layers will determine the success of the build process.

Inter-Layer Green Strength Stimate. For the purpose of this study, an inverted stepped solid cylinder (FIG. 4 (c)) was used as a specimen to measure the breaking load of the resin as a sumagate for green strength. This experiment measured the green strength of the cured PPF while a part is being built. After the burn-in layers, a cylinder of diameter and height of 1 mm (1 mm implies 20 layers of 50 μm each) was printed as a test specimen. Next, disks with increments of 0.5 mm in diameter and 150 μm in thickness were printed. This design allows for a separation force that gradually increments upward potentially inducing construct failure at some point. This separation force is named "breaking load", and the quotient of breaking load and the cross-sectional area of the test specimen (π/4 mm²) is called inter-layer green strength.

Figure 9:
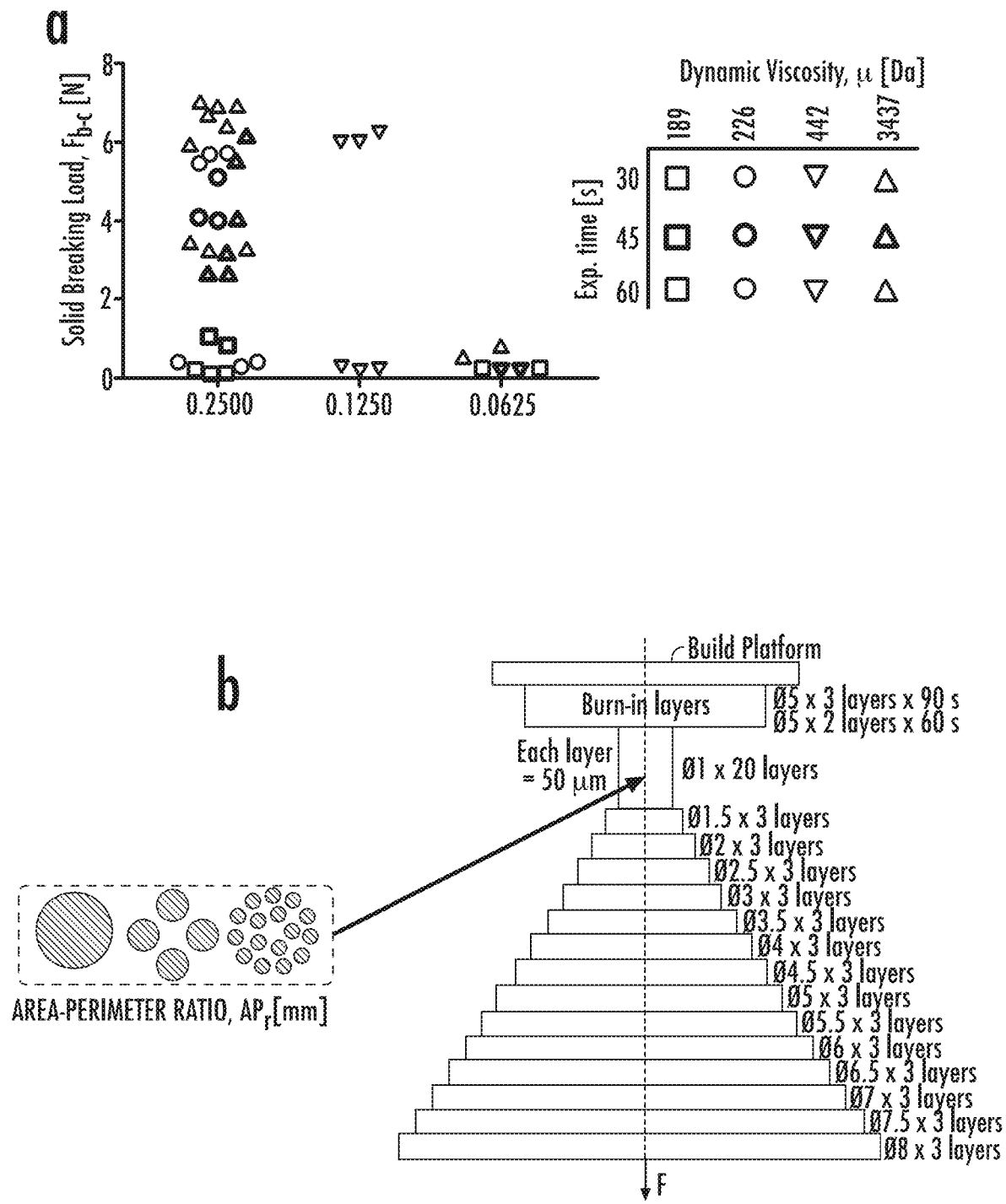
FIG. 9 depicts the breaking load of a solid part as a function of the exposure time, average molecular weight, and area-perimeter ratio.

An additional experiment was conducted in order to study the influence of the area-perimeter ratio in inter-layer green strength. The cylindrical test specimen was modified in order to keep constant the cross-sectional area while changing the perimeter. FIG. 9 shows the cross-section of the three area/perimeter specimens used. The area of the three specimens were π/4 mm², and the area-perimeter ratio was 0.25, 0.125, and 0.0625 mm. Four resins with different viscosities were tested randomly in this experiment.

Separation Force of Porous Structures. Scaffolds should guide the infusion of host tissue long enough for it to span the defect. The scaffold material must then resorb optimizing integration into surrounding tissue. Triply periodic minimal surfaces (TPMS) are of special interest to many scientists in the field of design and fabrication for bone tissue engineering applications due to the high area-volume ratio, high porosity, modulated structure, among others. These properties improve characteristics such as mechanical properties, permeability, cell adhesion, degradation and resorption. TPMS is defined by the equation, $$f(x, y, z) = \sum_{hkl} |F(hkl)| \cos(hX + kY + lZ - \alpha_{hkl}) = t$$

where X=2πx/a, Y=2πy/a, Z=2πz/a, (x, y, z) are the positions of the structure in the space, a denotes the length of the unit cell, $a_{hkl}$ denotes the phase angle, and |F(hkl)| denotes the symmetry of the structure (Michielsen and Kole 2003).

To generate the TPMS cylindrical porous scaffolds of 10 mm diameter and 5 mm height, MathMod V7.0 software was used. The TPMS geometries used as proof-of-concept to measure the separation force were the surfaces of Schoen's gyroid (G0) and the Inverse Tubular (IT). The following trigonometric functions were used:

$$G0: \cos(2.2x)\cdot\sin(2.2y)+\cos(2.2y)\cdot\sin(2.2z)+\cos(2.2z)\cdot\sin(2.2x)-0.75=0$$

$$IT: 10(\cos(3x)+\cos(3y)+\cos(3z))-5.1(\cos(3x)\cdot\cos(3y)+\cos(3y)\cdot\cos(3z)+\cos(3z)\cdot\cos(3x))-9.6=0$$

with boundary conditions x, y=[−5, 5] and z=[−2.5, 2.5]. The structures were generated without rotation around the origin of the cartesian coordinates system. The coefficients of the TPMS equations were modulated in order to obtain porous features suitable to build and monitoring the separation force. The gyroid structure exhibits porosity and pore size and an average strut size of 81%, 800 μm and 1000 μm, respectively. The inverse tubular structure has a porosity, pore size and a maximum strut size of 68%, 700 μm and 1400 μm, respectively.

The models with extension .obj modeled in Mathmod were exported to Meshlab (Cignoni et al. 2008) and converted in .stl format. Finally, Perfactory software 3.0 (EnvisionTEC®, Inc., Dearbon, MI, USA) was used to load the jobfile with the masks for printing. During the printing process of the porous structures, the separation force was recorded. The area and the perimeter of the projected masks were computed using the NIH software ImageJ (Schneider, Rasband, and Eliceiri 2012).

Results

PPF Resin Viscosity

Figure 5:
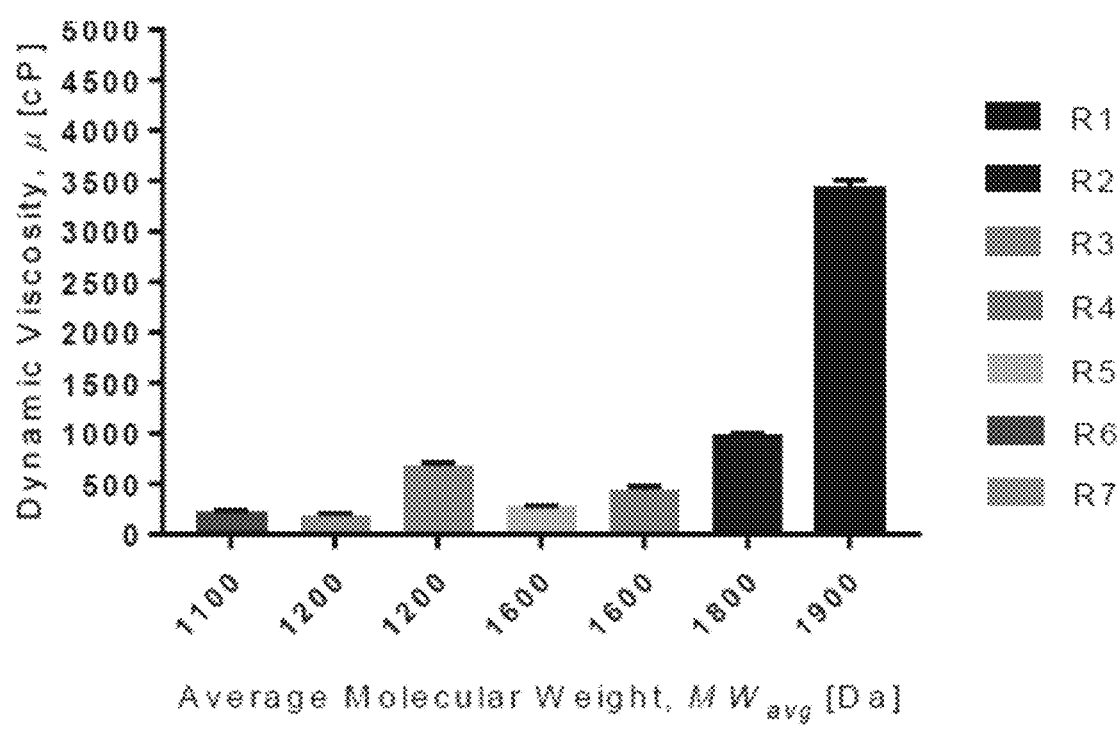
FIG. 5 is a bar chart showing the PPF resin dynamic viscosity at different average polymer molecular weights (n=5).

It was observed that the viscosity of PPF resin at 45° C. changes significantly for different molecular weights (FIG. 5). Surprisingly, resins prepared with PPF of the same average molecular weight (1200 and 1600 Da) from different batches presented variations in viscosity. These variations could not be explained by data recorded during the synthesis process of PPF. However, we will investigate this phenomenon.

Lu et al. synthetized PPF and the average molecular weight was tested using gel permeation chromatography. Using the refractive index mode, the average molecular weight was 1268 Da, and applying the ultraviolet mode the average molecular weight was 1592 Da. The authors consider that this difference is an acceptable range. The resin for cDLP 3D printing was prepared in combination con DEF (PPF/DEF 1:1) (Lu et al. 2015). The dynamic viscosity of this resin at 45° C. was ~1500 cP. (Choi et al. 2009) prepared a solution of PPF/DEF (7:3) with a pure PPF of ~1200 Da. They found that the dynamic viscosity at 45° C. was ~200 cP. On the other hand, the viscosity of our resins with average molecular weight between 1200 and 1600 cP is less than 1000 cP. Melchels, et al. (2009) suggest using viscosity values between 250 and 5000 cP for resorbable polymer resins in cDLP 3D printing processes.

Cure Depth

Figure 6:
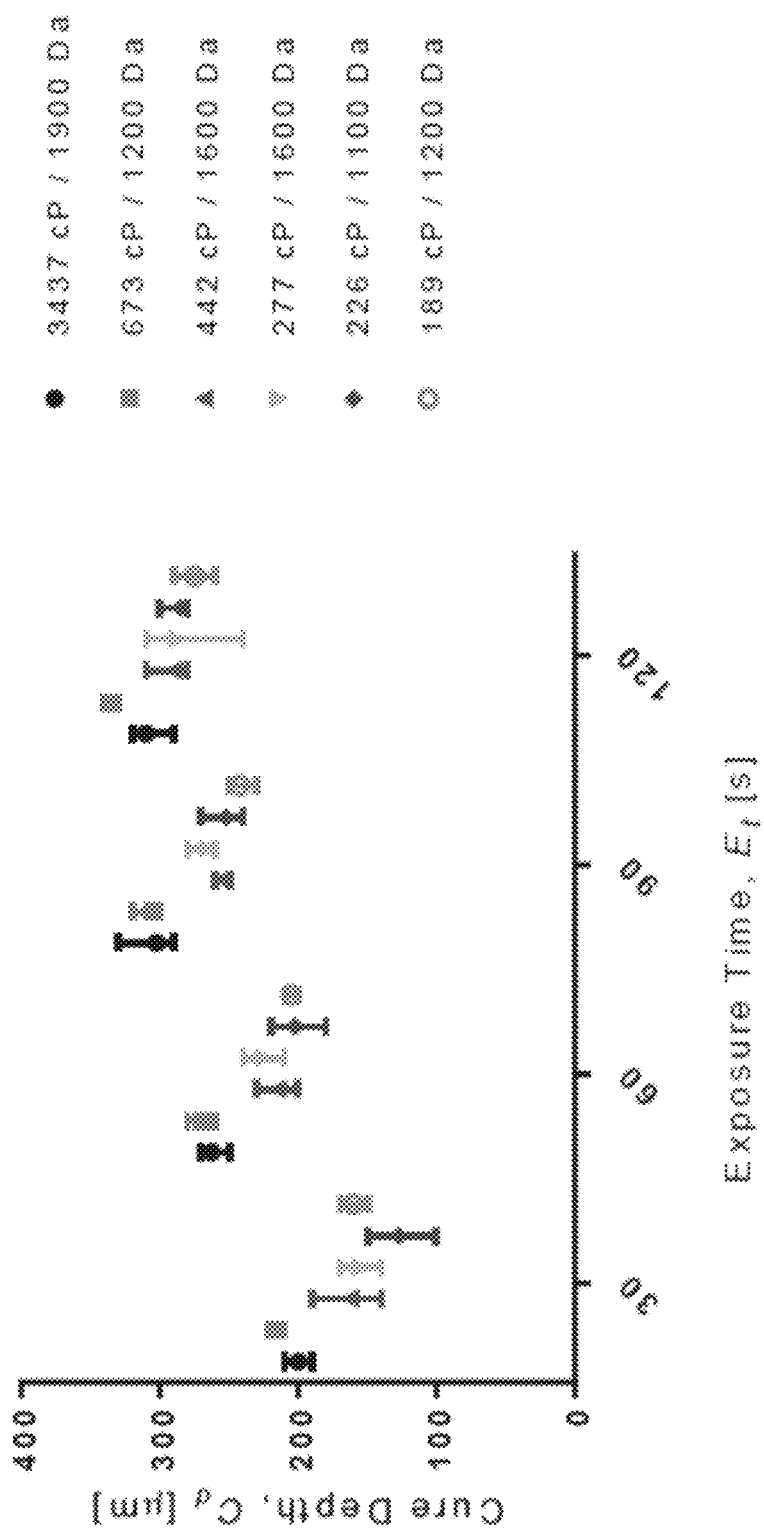
FIG. 6 is a scatterplot showing the cure depth for different exposure times (n=4).

From the curing experiment, a cure depth versus exposure time was obtained, as shown in FIG. 6. As noted, $C_d$ is modified with the viscosity and it is difficult to find a pattern. However, for an exposure time of 30 s, the resins with low viscosity (189 to 442 cP) are in the range proposed by Mott et al., that is ~150 μm (Mott et al. 2016). Even though the data acquired from this experiment does not directly correspond with ideal 3D printing conditions, the resulting data provides important insight into potential setting of manufacturing parameters and resin chemistry that will result in successful 3D printing.

Separation Force of Regular Shapes

Figure 7:
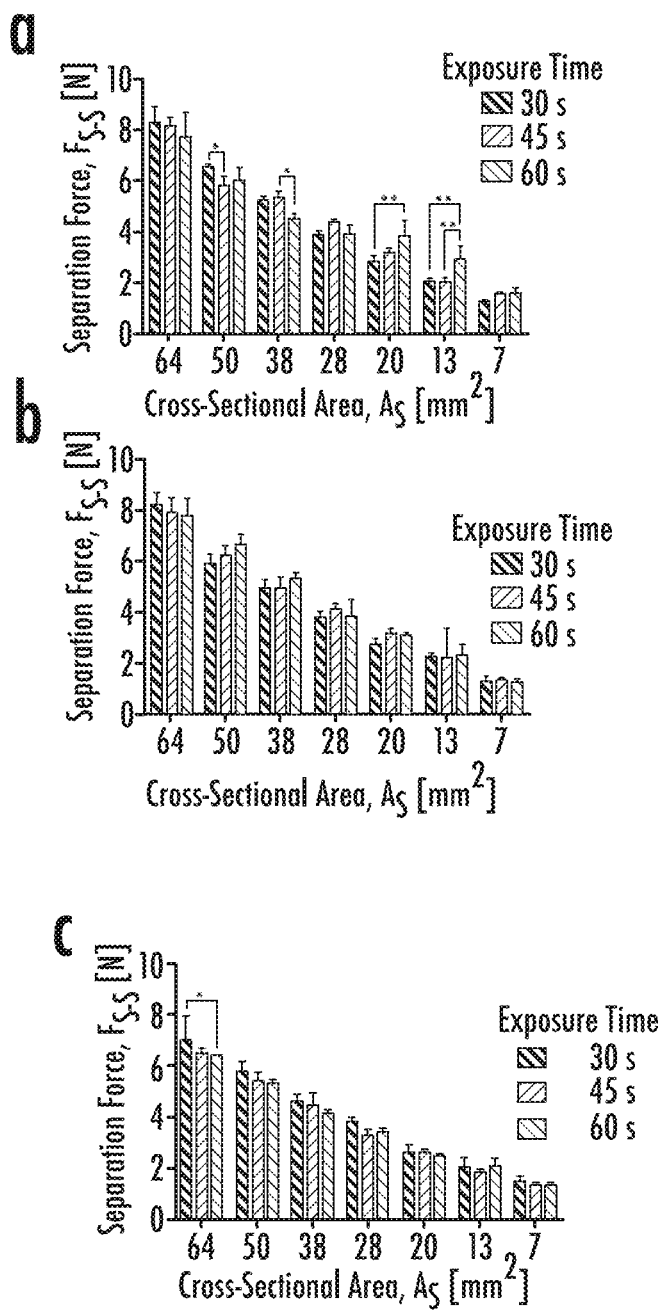
FIG. 7 depicts: the separation force versus cross-sectional area of a solid structure of (a) 189 cP/1200 Da, (b) 277 cP/1600 Da, (c) 673 cP/1200 Da, and (d) 3437 cP/1900 Da; and (e) a representative depiction of the separation force experiment specimen (n=3). (**P≤0.01, *P≤0.05).
Figure 7:
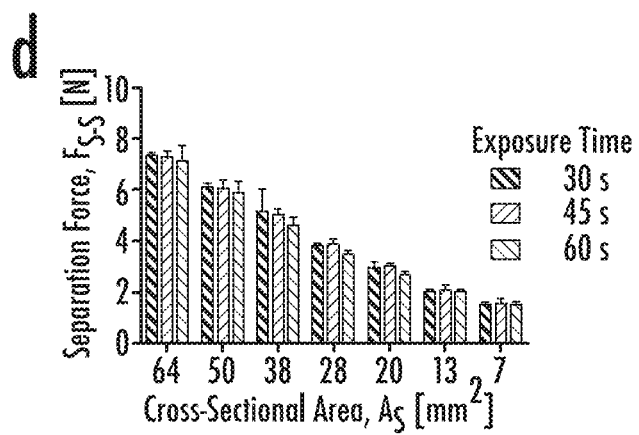
Figure 7:
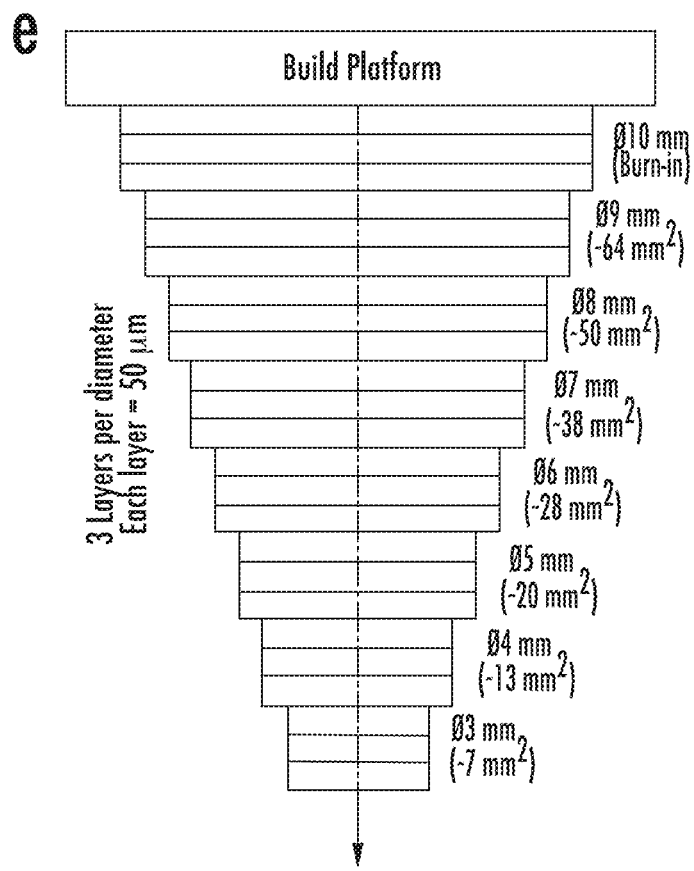

As noted in FIG. 7, the viscosity does not affect the separation force, that is the adhesive force with the basement, which in turn can lead to low yield or complete build failure. In FIG. 7 (a) with the resin of 1200 Da and a viscosity of 189 cP presents significance in the separation force values respect to the exposure time. In the rest of the resins, the exposure time practically has no statistical significance.

Inter-Layer Green Strength of Regular Shapes

Figure 8:
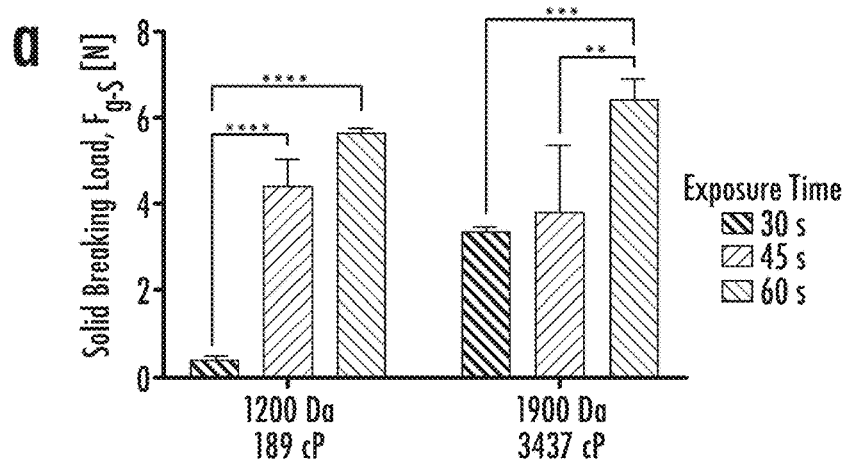
FIG. 8 depicts: the maximum loads and stress of a solid-cured part of PPF resin by (a) breaking load and (b) inter-layer green strength; and (c) a representative depiction of the breaking load experiment specimen (n=3). (**P≤0.0001, *P≤0.001, **P≤0.01)
Figure 8:
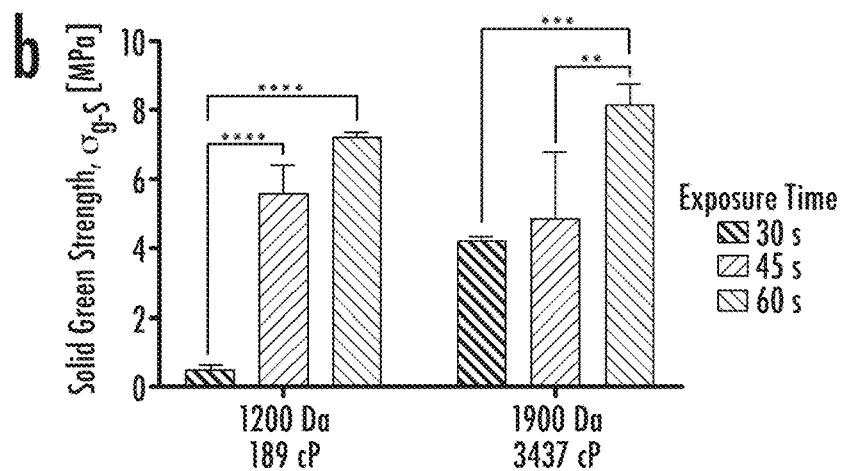
Figure 8:
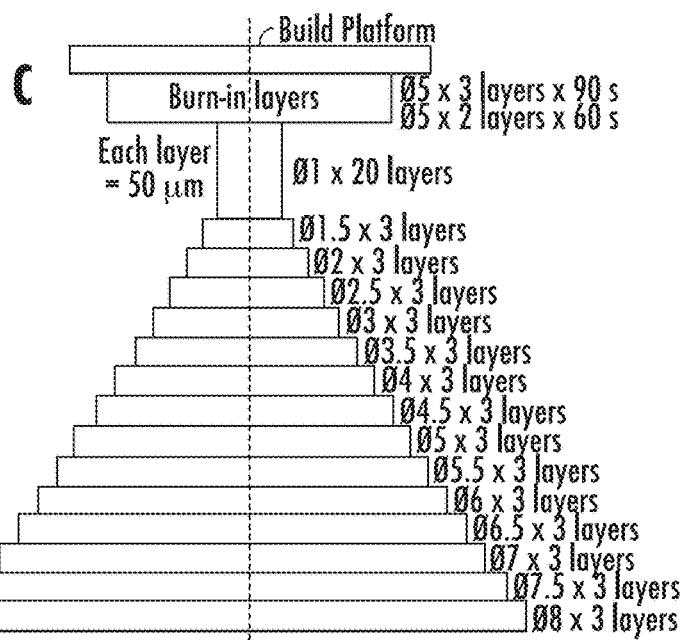

To the best of our knowledge, this is the first attempt to measure in line the breaking load and therefore the inter-layer green strength of a cured part during its printing using cDLP and PPF. The breaking load is the load applied at some point to a component of structure which leads to fracture. We consider as green strength to the quotient of the breaking load and the minimal cross-sectional area. FIG. 8 provides preliminary evidence that the green strength of the cured PPF is affected by the viscosity, average molecular weight and the exposure time.

FIG. 9 shows the breaking load for four resins with different viscosity as a function of the area-perimeter ratio and the exposure time. A reduction in the viscosity, exposure time and area-perimeter ratio leads to premature failure of the printed parts.

Separation Force of Porous Structures

Figure 10:
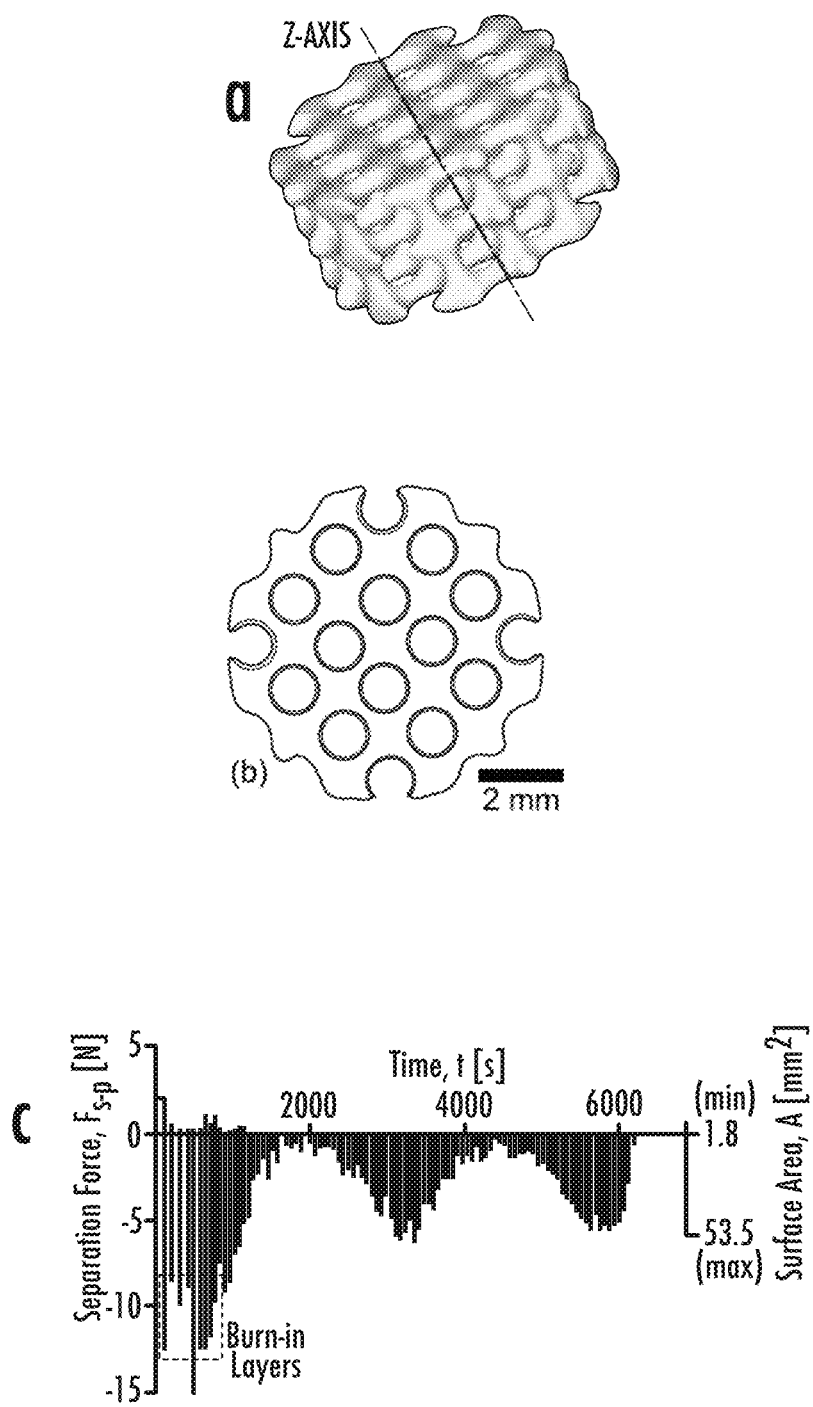
FIG. 10 depicts an inverted tubular porous scaffold printed with a resin of 226 cP/1100 Da using 45 second exposure time by (a) the CAD file, (b) a photograph of the printed scaffold, and (c) the measured force during the printing process.
Figure 11:
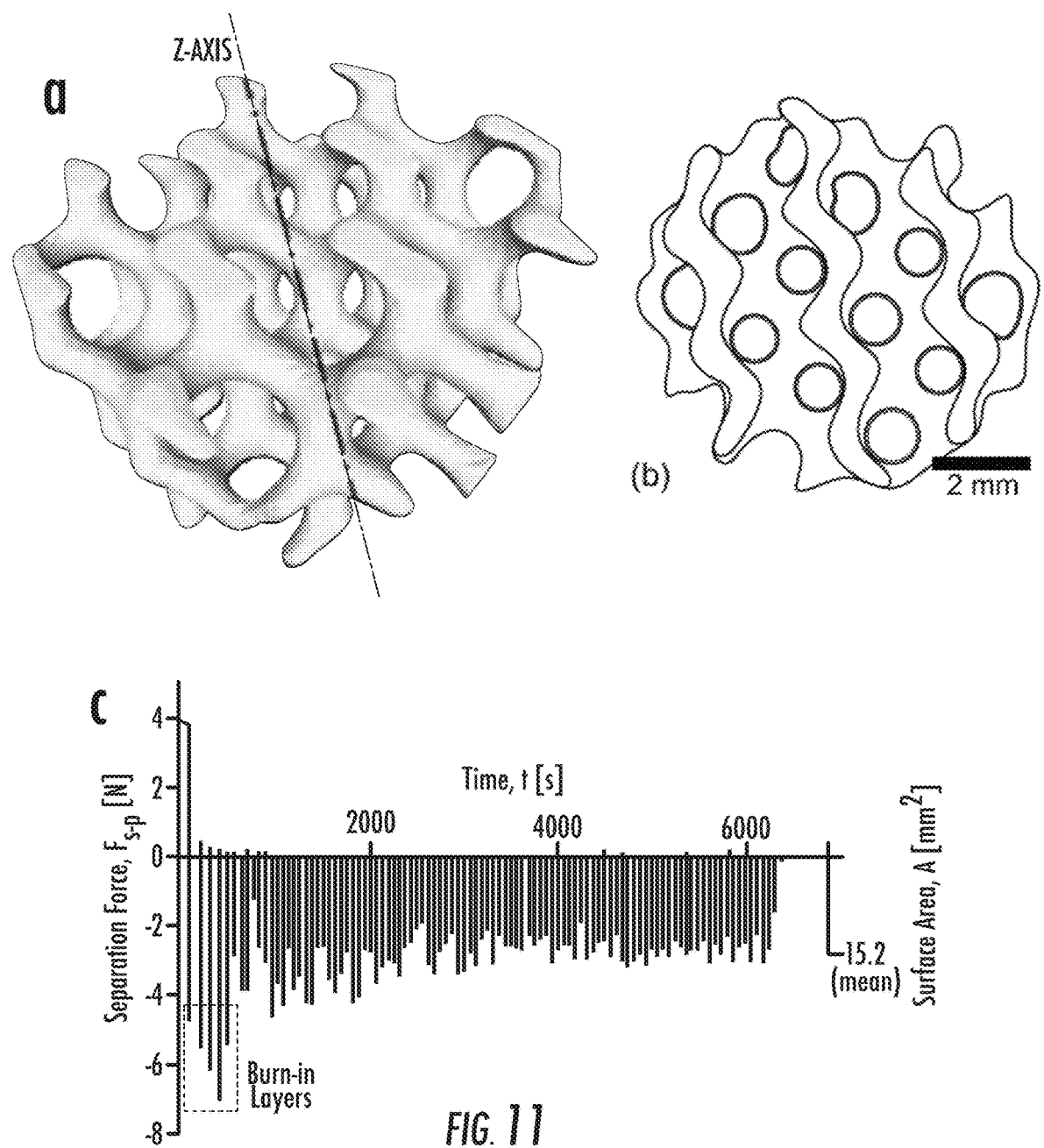
FIG. 11 depicts a 0°-gyroid porous scaffold printed with a resin of 44s cP/1600 Da using 45 s of exposure time by (a) the CAD file, (b) a photograph of the printed scaffold, and (c) the measured force during the printing process.

The architecture of the scaffold will directly impact its physical properties. In the field of bone tissue engineering, it is well known that pore size and shape influence tissue regeneration while strut size dramatically affects mechanical strength and resorption kinetics (Walker et al. 2017). For porous structures, the influence of print geometry on separation force becomes more complicated, as the uncured resin must be removed from the pores after printing and constrained surface deformations are more complicated than when printing solid structures. FIG. 10 shows a cylindrical scaffold with an inverted tubular (IT) surface pore geometry. The projection masks show a high variability in the cross-sectional area and its perimeter. That means when a mask with a large area is printing, its corresponding separation force (local separation force) will be higher and could lead to the failure of the previous printed regions that have less surface area. FIG. 11 shows a cylindrical porous scaffold based on a 0°-gyroid TPMS. The area and the perimeter distribution among the projection masks from layer to layer is more regular. Therefore, the separation force applied will be more constant, decreasing the probability of failure.

Figure 12:
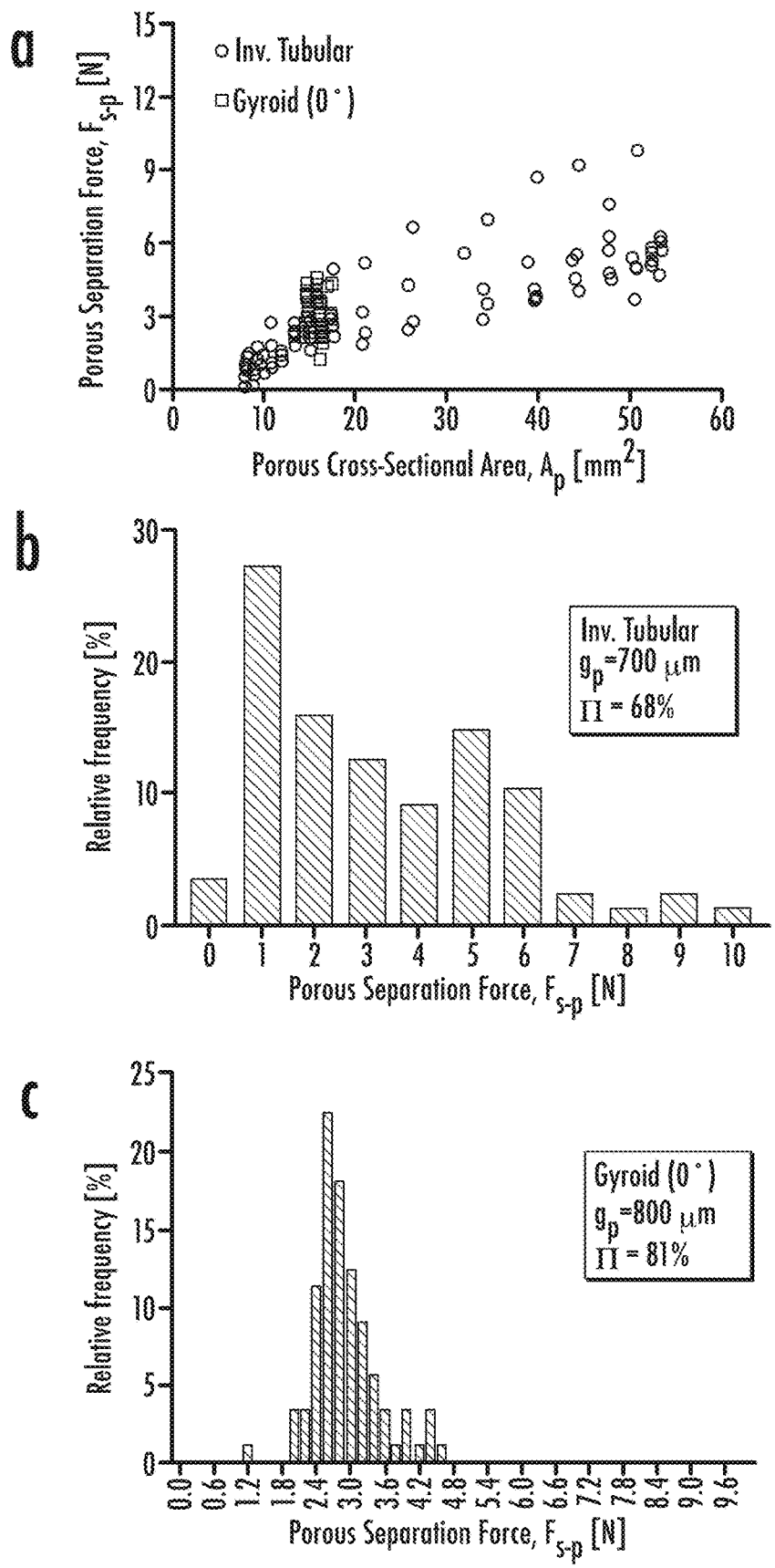
FIG. 12 depicts: (a) the breaking load of porous structures as a function of the cross-sectional area; (b) the distribution of separation force of the inverted tubular porous scaffold; and (c) the distribution of separation force of the 0°-gyroid porous scaffold.
Figure 13:
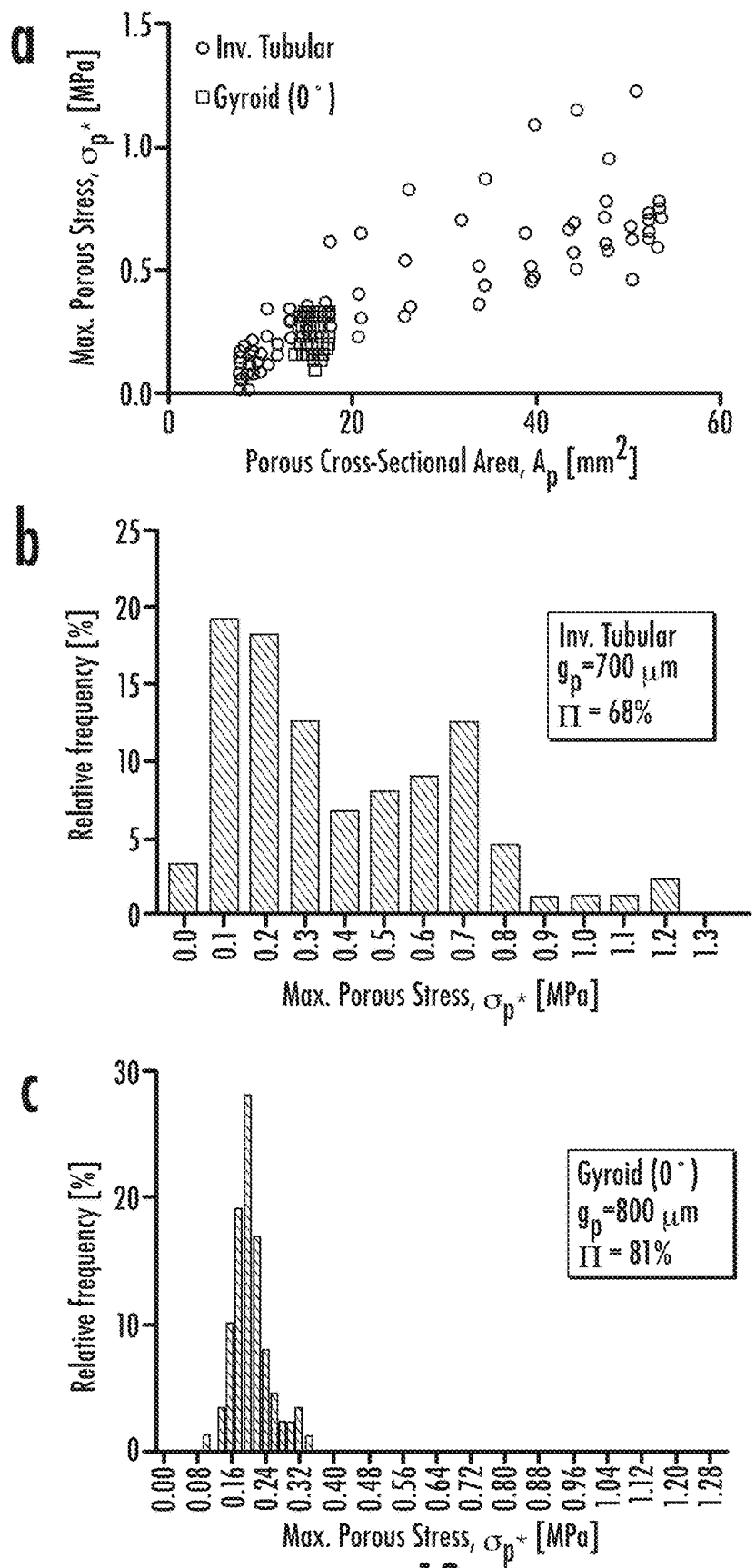
FIG. 13 depicts: (a) the maximum porous stress produced by the local separation force (separation force divided by the minimum cross-sectional area of the printed layers); (b) the distribution of maximum stress of the inverted tubular porous scaffold; and (c) the distribution of the maximum stress of the 0°-gyroid porous scaffold.

FIG. 12 shows the distribution of the separation force during the construction of the inverse tubular and 0°-gyroid scaffolds. It is challenging to print structures with a considerable variation between the printed layers. The distribution of the maximum stress produced by the local separation force on the minimum cross-sectional area of the porous scaffolds is shown in FIG. 13. As it was discussed previously, the large areas will cause relatively high separation forces, and therefore produce a high-stress concentration in the structure with less surface area from layer to layer.

Figure 14:
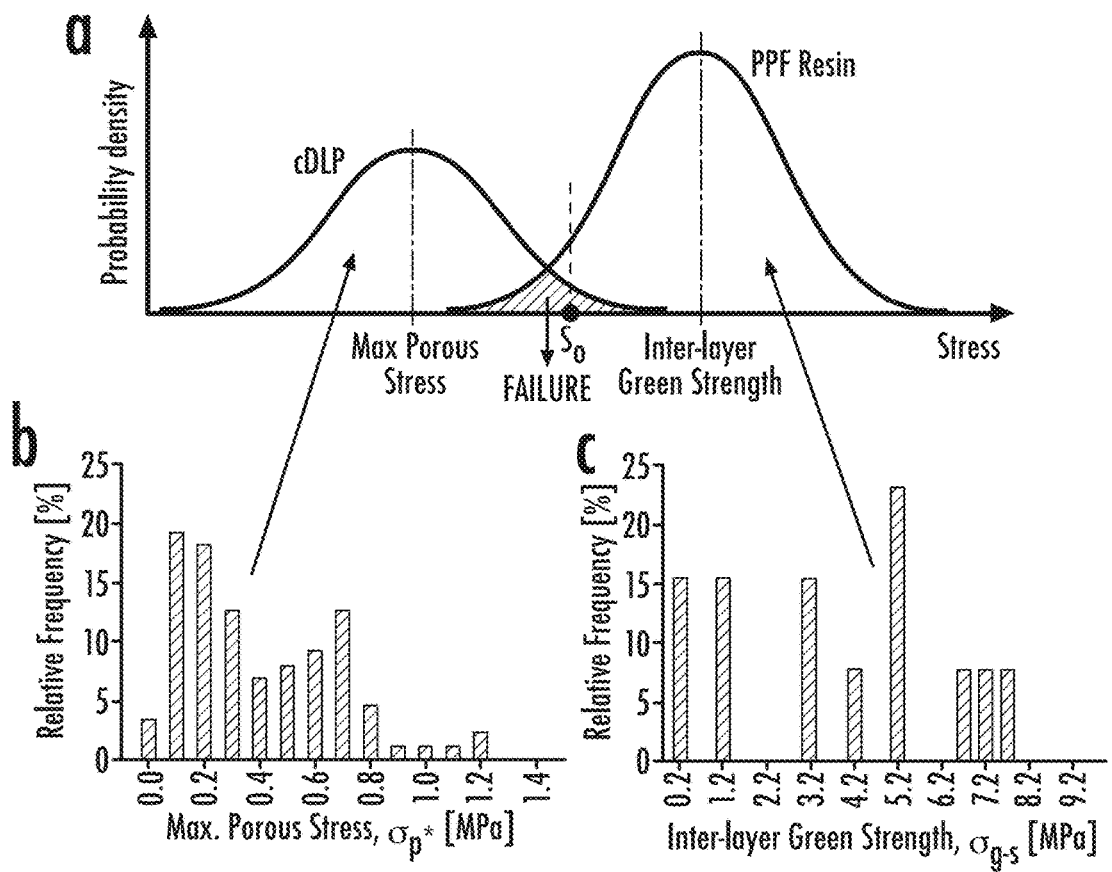
FIG. 14 depicts: (a) the load/strength interference model for PPF porous structures; (b) the distribution of the maximum stress for an inverted tubular porous scaffold (porosity 68%, pore size 800 μm, and maximum strut size 1400 μm); and (c) the distribution of green strength.

FIG. 14 (a) shows the concept of the load/strength interference model proposed by (Carter 1986) during the printing of PPF porous scaffolds using cDLP. This statistical design proposes that the failure-inducing stress arising from the load is not assumed to be unique (deterministic) but is allowed to vary according to some distribution. FIG. 14 (b) shows the distribution of the maximum porous stress for an inverted tubular porous scaffold (porosity 68%, pore size 700 μm, and maximum strut size 1400 μm). FIG. 14 (c)

shows the inter-layer green strength distribution of the PPF resin used for printing the inverted tubular porous scaffold.

Example 2. Direct Perfusion Bioreactor for Synthetic Bone Grafts

Material and Methods

Direct Perfusion Bioreactor

Figure 15:
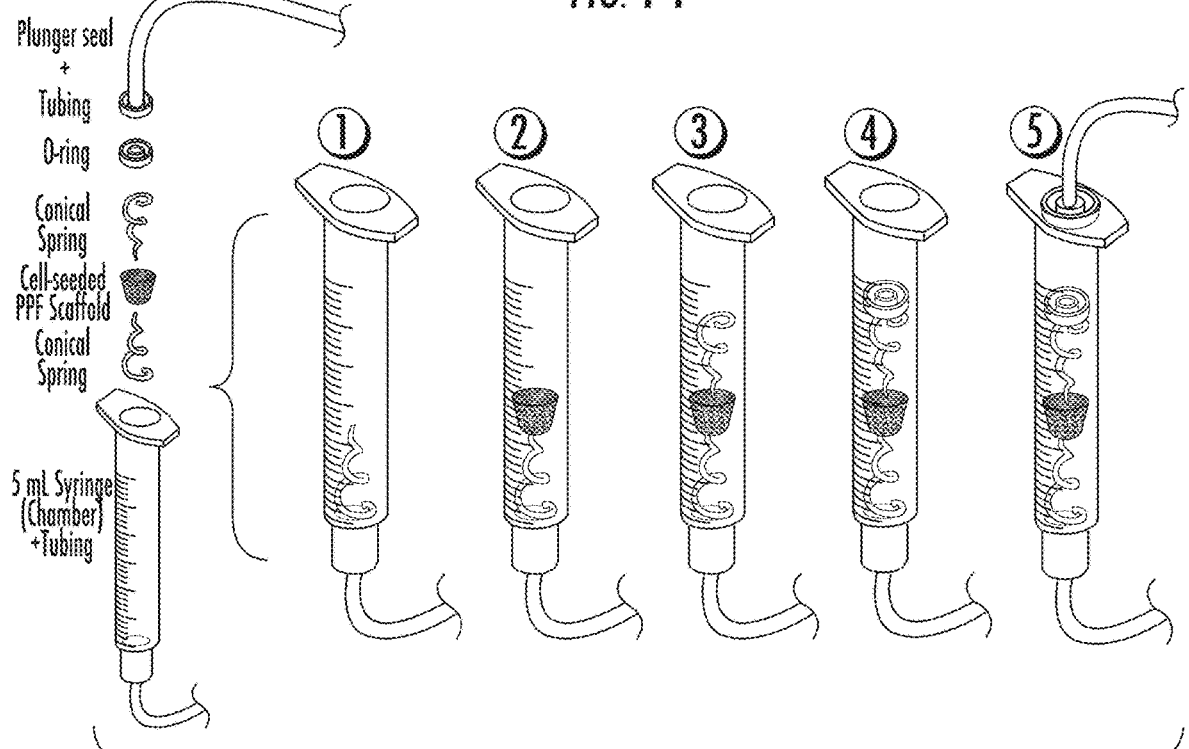
FIG. 15 depicts the perfusion chamber assembly as described in Example 2.

The present study describes a proof-of-concept to develop a modular perfusion bioreactor for BTE made with commercially available parts and it is suitable for sterilization with steam or some throw-away parts that can be bought sterile (FIG. 15). This system can be modular and inexpensive when use throw away bioreactor chambers or throw away and custom shape adapters (implant sleeve) for CFD modeling of non-cylindrical chambers and porous scaffolds, with high number of chambers. That is aided by splitting lines. The perfusion bioreactor system was formed by three chambers. Each chamber is formed by a 5 mL plastic syringe, one plunge seal, and two ⅛" Luer adapters. All the components used in the bioreactor can be autoclaved and hence can be sterilized easily and reliably. ⅛"-diameter permeable tubing (C-Flex, Cole-Parmer, Vernon Hills, IL, USA) was used for the connections inside of the incubator, and commercial ⅛"-diameter PVC tubing was used to connect the system with the pump located outside the incubator. After each culture, the perfusion chamber can be discarded. The design presented here has been refined and some components have been modified based on the problems presented in a previous attempt (Tramp 2015).

A peristaltic pump (Simply Pumps PM200N, Manor, PA, USA) was adapted to connect to a NEMA-17 planetary geared stepper motor (17HS 19-1684S-PG27 Stepperonline, Nanjing, China). In order to drive the peristaltic pump, a Stepper Motor Driver Board (WINGONEER TB6560 3A Single-Axis Controller, China) was used. To command the driver board an Arduino UNO microcontroller board (HiLetgo, Shenzhen, China). The peristaltic pump was assembled in a lateral part of the case of the incubator.

Porous Scaffolds

Six PPF porous scaffolds with diameter 12 mm, 5 mm height, 400 μm strut size, 1400 μm pore size, and ~88% porosity were fabricated according to (Walker et al. 2017). To design of porous scaffolds, a triply periodic minimal surface (TPMS) geometry called Schoen's gyroid was used. The equation of the Schoen's gyroid is:

$$\sin(Nx)\cos(Ny)+\sin(Ny)\cos(Nz)+\sin(Nz)\cos(Nx)-C=0$$

with N, and C are constants. An algorithm implemented in MATLAB® (MathWorks, Natick, MA, USA) was used to generate the cylindrical porous scaffolds in a tessellated format (STL). The geometries obtained were used for additive manufacturing fabrication and for finite element analysis after a preprocessing stage to obtain a tetrahedral meshing.

Perfusion Culture Cytotoxicity

An L929 cell line was used to seed the scaffolds with a density of 1 million cells/scaffold they were allowed to attach for 4 h before putting them in the perfusion chambers. Three scaffolds were used for perfusion, and three without flow as controls.

The bioreactor parts: connectors, O-rings, conical springs, and tubing were autoclaved using an instruments cycle. A test tube rack was used to keep the perfusion chambers (syringes) vertically. The rack was cleaned with 70% ethanol and UV sterilized for 3 hours inside a laminar air flow hood.

The perfusion bioreactor was assembled inside a laminar flow hood maintained in sterile conditions. Briefly, the hood was sterilized using a UV lamp for 15 minutes, then the sterilization pouches were placed inside the hood. Carefully, the pouches were opened and using a tweezer, the conical springs were place in the bottom of the chambers. The cell-seeded scaffolds were inserted in the chamber to contact with the conical spring. A second group of conical springs were placed to support the other side of the cell-seeded scaffolds. These springs were fixed using the O-rings. Finally, the plungers were connected to seal the perfusion chamber (FIG. 15).

Three syringes were used to prime the perfusion chambers. The upper side of the chambers was connected to the priming syringes and the opposite side were connected to the media reservoir. When media reached the scaffold, it was necessary to assure the absence of air bubbles. If some air bubble appears, we use the priming syringes to remove the bubbles pushing the media back through to force the bubbles into the media reservoir. Finally, the syringes were removed and the recirculation tubing for perfusion was connected.

The final assembly was carefully moved into the incubator. As soon as possible, the recirculation tubing was connected to the peristaltic pump. Perfusion was started inside the incubator and the flow rate of the pump was set to 10 mL/min to prime the complete assembly (~20 min), and finally it was set to 5.5 mL/min for perfusion during 24 h. The incubator was maintained at temperature of 37° C. and 5% of $CO_2$.

Live-Dead Assay

Cell viability was evaluated using Prestoblue® Cell Viability Reagent (Invitrogen, USA). Each scaffold was submerged in a solution made with 2 mL of Prestoblue and 18 mL of media, and the scaffolds were incubated at 37° C. and 5% of $CO_2$. After 1 hour of incubation, viability was quantified by fluorescence acquisition using a plate reader equipped with appropriate excitation and emission filters. Higher relative fluorescence units (RFU) are indicative of more metabolic activity which can be related to increased cell numbers having migrated.

Computational Fluid Dynamics

The media flowing throughout the system was regarded as a three-dimensional inviscid and incompressible Newtonian fluid modeled by the Navier-Stokes equations.

Preprocessing

This step comprises of input off the required data in the finite element software. The required data comprises the problem formulation stage: geometry, governing equations, boundary conditions, initial conditions and properties, and the implementation stage: meshing, time steps, approach for solving algebraic equations and tolerances (Datta and Rakesh 2009). STL triangulation cannot be used directly in the finite element method, mainly because it requires specific characteristics in the geometrical description of the domain to be compute. (Béchet, Cuilliere, and Trochu 2002). The STL mesh was cleaned using Meshlab, using a Taubin algorithm (Taubin 1995). Finally, Amira software (Mercury Computer Systems/3D Viz group, San Diego, CA) or Gmsh (Geuzaine and Remacle 2009) were used to create the mesh for FEM. The quality factor of the triangles was evaluated using COMSOL. A detailed procedure is explained in the Appendices A7-7, A7-24, and A7-31.

Processing

Figure 16:
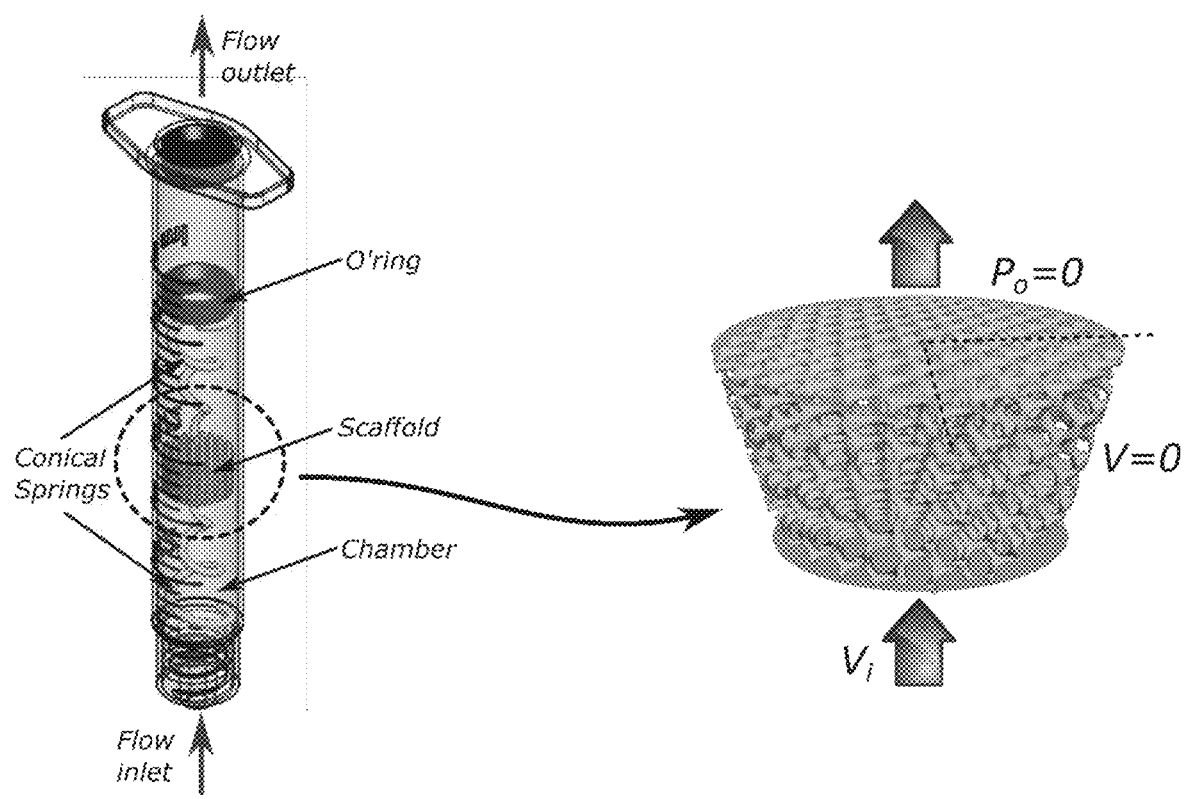
FIG. 16 is a schematic view of the perfusion chamber designed for cell culture and boundary conditions.

The shear stress on the cells induced by fluid flow could be estimated using simulation techniques. The fluid velocity was obtained by numerically solving for Navier-Stokes Equations on the fluid inside the perfusion chamber. Water properties were used as media properties. Density of the media (1000 kg/m$^3$), and viscosity of the media (0.6915×10$^{-3}$ Pa·s). The media was assumed to be an incompressible and Newtonian fluid. Other assumptions like no-slip boundary condition on the boundaries, uniform velocity of 1 mm/s at the inlet of the chamber, and zero-gauge pressure at the outside of the chamber were made (FIG. 16). Flow inside of the bioreactor was assumed to be laminar. The flow from the pump was assumed to be uniform and any pulsatile action was neglected. Stationary approach was used in the numerical simulation was done using the CFD Module in COMSOL Multiphysics 5.2 (COMSOL, Burlington, MA, USA).

Post-Processing

Figure 17:
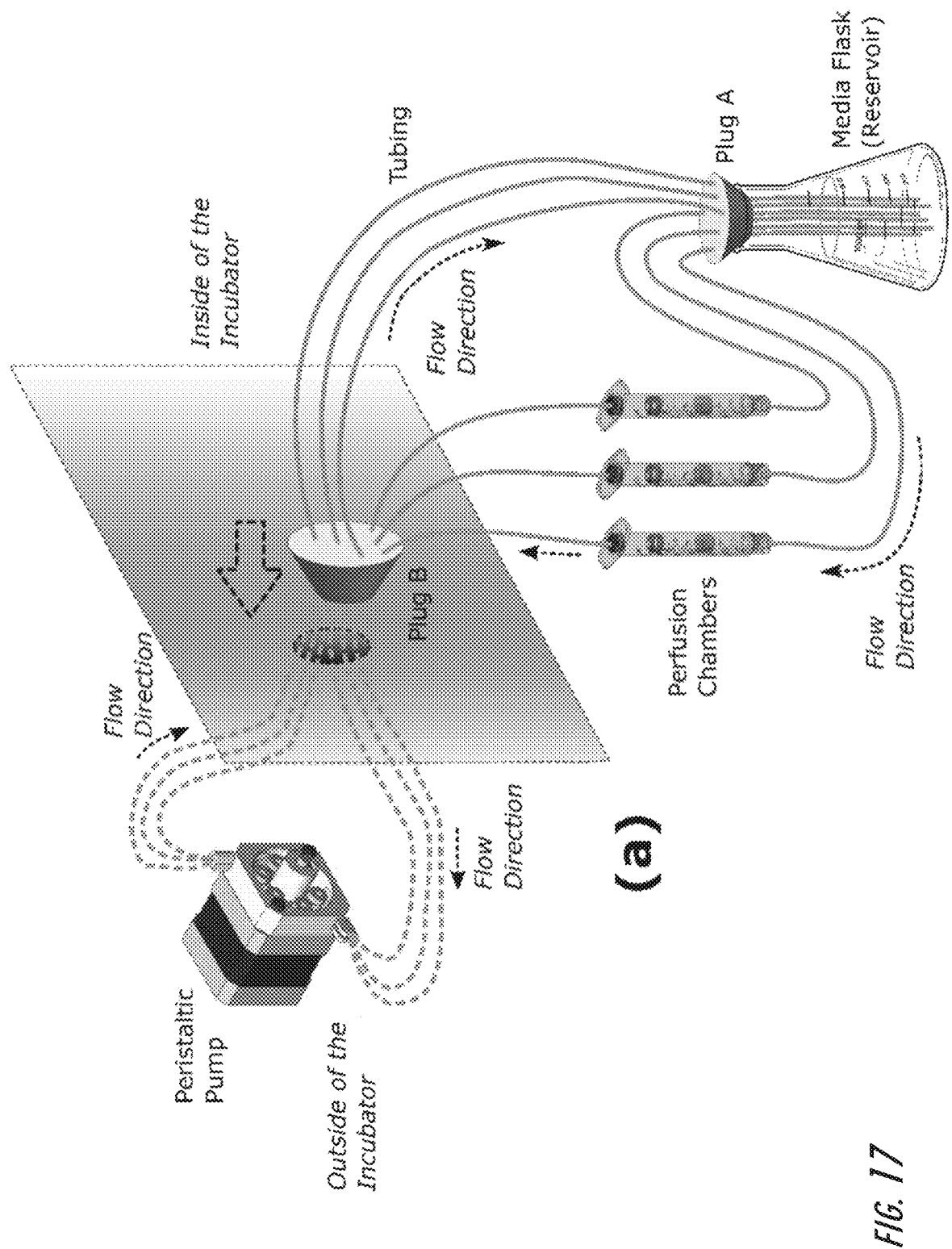
FIG. 17 depicts the perfusion culture setup by: (a) a schematic presentation of the perfusion bioreactor system used in Example 2 to provide perfusion through three cell-seeded scaffolds that were press-fit into the chambers (syringes); (b) a photograph of the assembly of the perfusion bioreactor system inside of an incubator at 37° C. and 5% $CO_2$; and (c) the peristaltic pump system installed outside the incubator.
Figure 17:
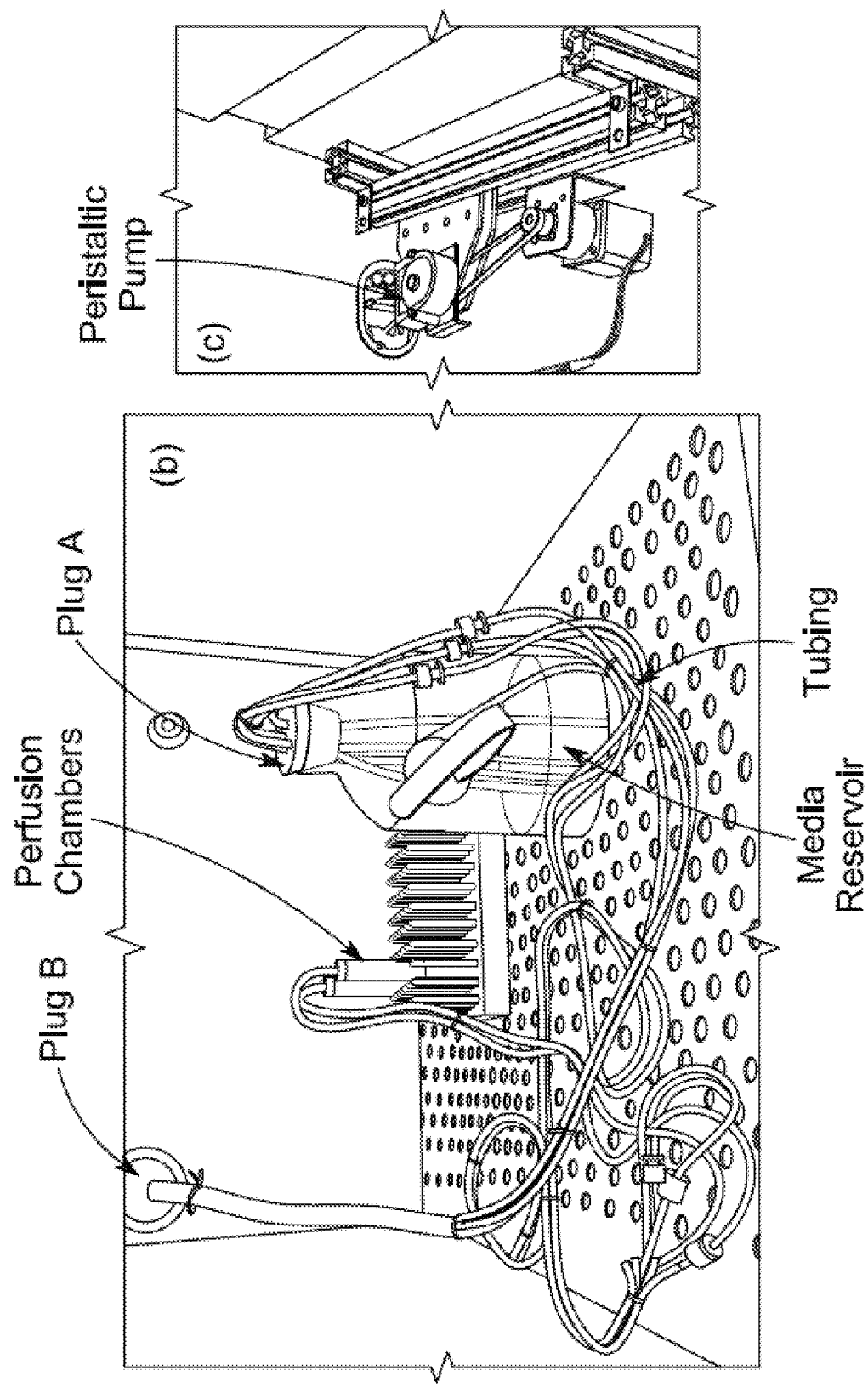

The convergence of the numerical solution and the element quality was evaluated. A quarter of the scaffold was simulated, computing the distribution of the velocity and shear stress. A goal of flow was to provide sufficient nutrients and growth factors throughout scaffold and remove waste products sufficiently from all parts, especially deep interior which may not get adequate growth factors and nutrients and may be site of waste product build-up in static culture, especially as porous scaffolds increase in size Results Perfusion Culture Setup The perfusion bioreactor system was configured as a closed-loop system (FIG. 17). The peristaltic pump head was adapted to drive three lines at the same time. The geared-box stepper motor supplied enough torque for the peristaltic movement. The bioreactor chambers sealed the scaffolds and allowed direct perfusion through the porous scaffolds. The conical springs reduced the formation of bubbles during the priming stage due to the superficial tension forces produced in the internal wall of the chamber. As the media flows through the scaffolds, shear stresses occur on the surfaces, nutrients are supplied, and waste is extracted from the culture areas. It is possible to create different levels or gradients of shear stress controlling the flow rate with the peristaltic pump. The permeable tubing promoted gaseous exchange between the media and the CO$_2$ of the incubator.

Live-Dead Assay

Static culture scaffolds showed 4500 RFU of fluorescence intensity. Perfused scaffolds exhibited 2500, 4500 and 3500 RFU. These preliminary results demonstrate that the design and implementation of the perfusion culture system is suitable for dynamic cell culture. The main objective of this assay was to validate the perfusion system. There are several criteria that determine the performance of a cell culture protocol, i.e., cell type, cell source, scaffold type, objective of the study, etc. However, this analysis is beyond the scope of the present study.

Computational Fluid Dynamics

Figure 18:
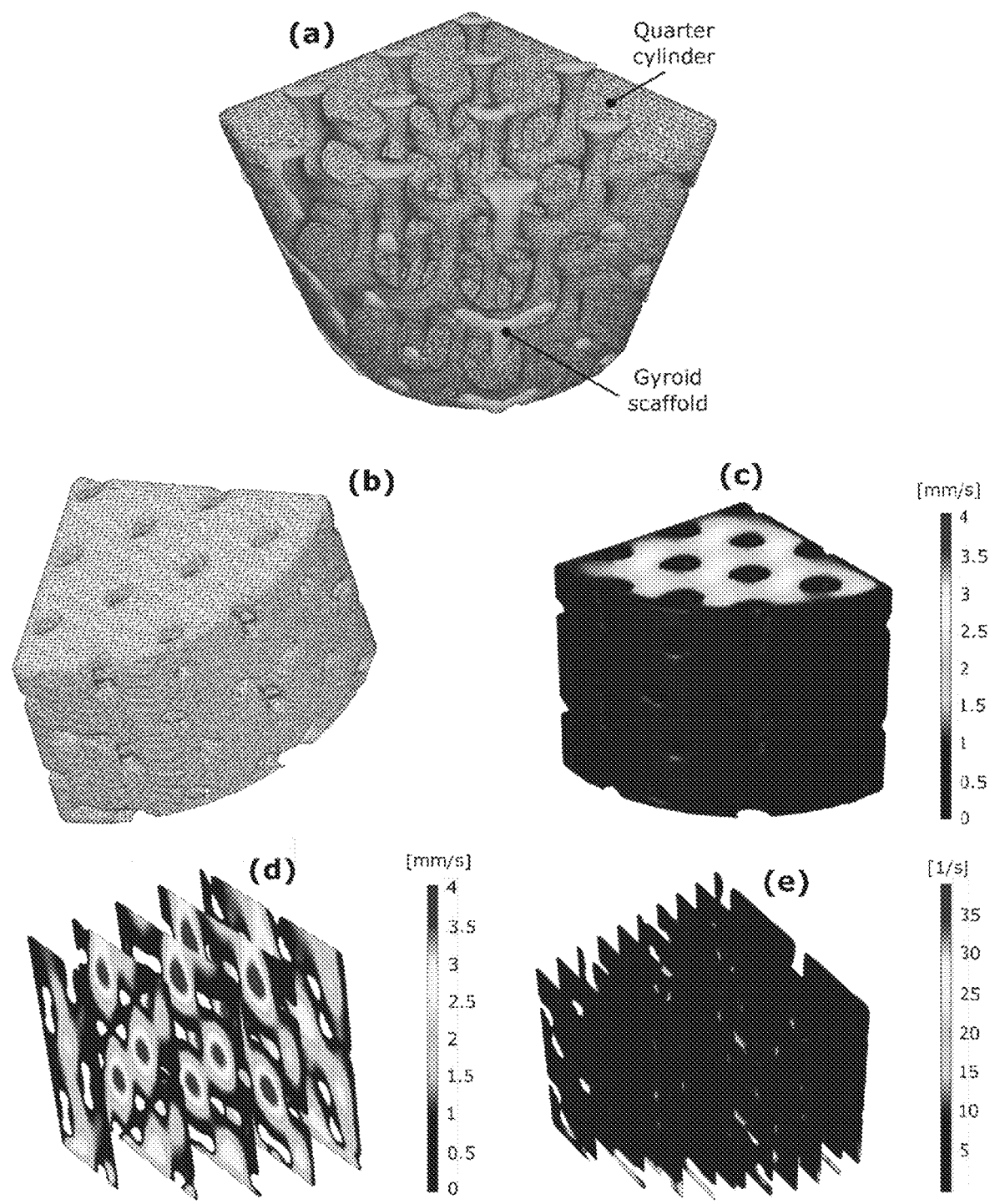
FIG. 18 depicts the computation modeling of the perfusion flow through the gyroid scaffold by: (a) Boolean difference operation between a quarter cylinder domain and quarter cylindrical gyroid scaffold; (b) 3D unstructural mesh with tetrahedral elements generated with Gmsh for the finite element study; (c) velocity magnitude of the flow through the domain; (d) the velocity contours of the flow medical showing high profiles of velocity and probable vortices in some regions of the porous structures; and (e) the shear stress distribution produced by the perfused flow.

The domain for the finite element analysis was obtained using difference as geometric Boolean operation, (FIG. 18 (a)). It is critical to select adequate parameters when the refinements and smoothing filters (e.g., Taubin filter) are applied in the preprocessing stage. Before full CFD simulation, a mesh convergence study was performed to maximize the result accuracy. The final unstructured mesh with uniform mesh distribution and average element quality of 0.7085 was concluded as suitable for our purposes. The optimal mesh was obtained using 565372 tetrahedral elements (FIG. 18 (b)). If the priority of a direct perfusion bioreactor is to ensure homogeneous flow conditions throughout the scaffolds. Computational modeling of the perfusion bioreactor allowed for flow characteristics identification (FIGS. 18 (c) and (d)) in the bioreactor and the resulting mechanical stimulation (FIG. 18 (e)). Shear stress is caused by the flow of fluid across the surface and its value is directly proportional to the velocity of the surrounding fluid. Shear stress cannot be sensed, it is only approximated with CFD techniques. Due to the complexity of the porous geometry and the physical model used in the present research, a validation of the model is mandatory to define if the level of agreement of the results is desirable for future improvements of the 3D-cell culture protocols.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

REFERENCES CITED

Abhay, Sanan, and Stephen J. Haines. 1997. "Repairing Holes in the Head: A History of Cranioplasty." *Neurosurgery*, March.

"Atlas of Human Anatomy-6th Edition." n.d. Accessed Feb. 19, 2018.

Banic, Andrej, and Ralph Hertel. 1993. "Double Vascularized Fibulas for Reconstruction of Large Tibial Defects." *Journal of Reconstructive Microsurgery* 9 (06): 421-28.

Basu, Bikramjit. 2017. "Natural Bone and Tooth: Structure and Properties." In *Biomaterials for Musculoskeletal Regeneration*, 45-85. Indian Institute of Metals Series. Springer, Singapore.

Béchet, E., J.-C. Cuilliere, and F. Trochu. 2002. "Generation of a Finite Element MESH from Stereolithography (STL) Files." *Computer-Aided Design* 34 (1): 1-17.

Bochove, Bas van, Gerjon Hannink, Pieter Buma, and Dirk W. Grijpma. 2016. "Preparation of Designed Poly(Trimethylene Carbonate) Meniscus Implants by Stereolithography: Challenges in Stereolithography." *Macromolecular Bioscience* 16 (12): 1853-63.

Burr, David B., A. G. Robling, and C. H. Turner. 2002. "Effects of Biomechanical Stress on Bones in Animals." *Bone* 30 (5): 781-86.

Choi, Jae-Won, Ryan Wicker, Seok-Hee Lee, Kyung-Hyun Choi, Chang-Sik Ha, and Ildoo Chung. 2009. "Fabrication of 3D Biocompatible/Biodegradable Micro-Scaffolds Using Dynamic Mask Projection Microstereolithography." *Journal of Materials Processing Technology* 209 (15): 5494-5503.

Cignoni, Paolo, Marco Callieri, Massimiliano Corsini, Matteo Dellepiane, Fabio Ganovelli, and Guido Ranzuglia. 2008. *MeshLab: An Open-Source Mesh Processing Tool.* The Eurographics Association.

Datta, Ashim, and Vineet Rakesh. 2009. "An Introduction to Modeling of Transport Processes: Applications to Biomedical Systems." Cambridge Core. November 2009.

Dean, David, Jonathan Wallace, Ali Siblani, Martha O. Wang, Kyobum Kim, Antonios G. Mikos, and John P. Fisher. 2012. "Continuous Digital Light Processing (CDLP): Highly Accurate Additive Manufacturing of Tissue Engineered Bone Scaffolds." *Virtual and Physical Prototyping* 7 (1): 13-24.

DeCoster, Thomas A., Rick J. Gehlert, Elizabeth A. Mikola, and Miguel A. Pirela-Cruz. 2004. "Management of Post-traumatic Segmental Bone Defects." *The Journal of the American Academy of Orthopaedic Surgeons* 12 (1): 28-38.

Gardel, Leandro S., Luís A. Serra, Rui L. Reis, and Manuela E. Gomes. 2014. "Use of Perfusion Bioreactors and Large Animal Models for Long Bone Tissue Engineering." *Tissue Engineering. Part B, Reviews* 20 (2): 126-46.

Geuzaine, Christophe, and Jean-François Remacle. 2009. "Gmsh: A 3-D Finite Element Mesh Generator with Built-in Pre- and Post-Processing Facilities." *International Journal for Numerical Methods in Engineering* 79 (11): 1309-31.

Giannitelli, S. M., D. Accoto, M. Trombetta, and A. Rainer. 2014. "Current Trends in the Design of Scaffolds for Computer-Aided Tissue Engineering." *Acta Biomaterialia* 10 (2): 580-94.

Giannitelli, S. M., P. Mozetic, M. Trombetta, and A. Rainer. 2015a. "Combined Additive Manufacturing Approaches in Tissue Engineering." *Acta Biomaterialia* 24 (September): 1-11.

Giannoudis, Peter V., Haralambos Dinopoulos, and Eleftherios Tsiridis. 2005. "Bone Substitutes: An Update." *Injury* 36 Suppl 3 (November): S20-27.

Gibson, Ian, David Rosen, and Brent Stucker. 2015. *Additive Manufacturing Technologies: 3D Printing, Rapid Prototyping, and Direct Digital Manufacturing.* 2nd ed. New York: Springer-Verlag. Griffin, Kaitlyn S., Korbin M. Davis, Todd O. Mckinley, Jeffrey O. Anglen, Tien-Min G. Chu, Joel D. Boerckel, and Melissa A. Kacena. 2015. "Evolution of Bone Grafting: Bone Grafts and Tissue Engineering Strategies for Vascularized Bone Regeneration." *Clinical Reviews in Bone and Mineral Metabolism* 13 (4): 232-44.

Haj, A. J. El, and S. H. Cartmell. 2010. "Bioreactors for Bone Tissue Engineering." *Proceedings of the Institution of Mechanical Engineers, Part H: Journal of Engineering in Medicine* 224 (12): 1523-32.

Hollister, Scott J. 2005a. "Porous Scaffold Design for Tissue Engineering." *Nature Materials* 4 (7): 518-24.

Holzapfel, Boris Michael, Johannes Christian Reichert, Jan-Thorsten Schantz, Uwe Gbureck, Lars Rackwitz, Ulrich Noth, Franz Jakob, Maximilian Rudert, Jürgen Groll, and Dietmar Werner Hutmacher. 2013a. "How Smart Do Biomaterials Need to Be? A Translational Science and Clinical Point of View." *Advanced Drug Delivery Reviews*, Bionics—Biologically inspired smart materials, 65 (4): 581-603.

Huang, You-Min, and Cho-Pei Jiang. 2005. "On-Line Force Monitoring of Platform Ascending Rapid Prototyping System." *Journal of Materials Processing Technology* 159 (2): 257-64.

Hutmacher, D. W. 2000. "Scaffolds in Tissue Engineering Bone and Cartilage." *Biomaterials* 21 (24): 2529-43.

Ibrahim, A. 2018. "13-3D Bioprinting Bone." In *3D Bioprinting for Reconstructive Surgery*, edited by Daniel J. Thomas, Zita M. Jessop, and Iain S. Whitaker, 245-75. Woodhead Publishing.

"Introduction to Reliability Engineering." 2011. In *Practical Reliability Engineering*, by Patrick D. T. O'Connor and Andre Kleyner, 1-18. Chichester, UK: John Wiley & Sons, Ltd.

Ivanovski, S., C. Vaquette, S. Gronthos, D. W. Hutmacher, and P. M. Bartold. 2014. "Multiphasic Scaffolds for Periodontal Tissue Engineering." *Journal of Dental Research* 93 (12): 1212-21.

Jacobs, Paul. 1992. *Rapid Prototyping & Manufacturing Fundamentals of StereoLithography.* First. Society of Manufacturing Engineers.

Jariwala, Shailly H., Gregory S. Lewis, Zachary J. Bushman, James H. Adair, and Henry J. Donahue. 2015. "3D Printing of Personalized Artificial Bone Scaffolds." *3d Printing and Additive Manufacturing* 2 (2): 56-64.

Karageorgiou, Vassilis, and David Kaplan. 2005. "Porosity of 3D Biomaterial Scaffolds and Osteogenesis." *Biomaterials* 26 (27): 5474-91. https://doi.org/10.1016/j.biomaterials.2005.02.002.

Karande, Tejas S., Joo L. Ong, and C. Mauli Agrawal. 2004. "Diffusion in Musculoskeletal Tissue Engineering Scaffolds: Design Issues Related to Porosity, Permeability, Architecture, and Nutrient Mixing." *Annals of Biomedical Engineering* 32 (12): 1728-43.

Kinaci, Ahmet, Valentin Neuhaus, and David C. Ring. 2014. "Trends in Bone Graft Use in the United States." *Orthopedics* 37 (9): e783-788.

Kovalenko, Iaroslav, Sylvain Verron, Maryna Garan, Jiří Šafka, and Michal Moučka. 2017. "Implementation of Non-Destructive Evaluation and Process Monitoring in DLP-Based Additive Manufacturing." *Open Engineering* 7 (1): 100-105.

Langer, R., and J. P. Vacanti. 1993. "Tissue Engineering." *Science* (New York, N.Y.) 260 (5110): 920-26.

Laurencin, Cato, Yusuf Khan, and Saadiq F. El-Amin. 2006. "Bone Graft Substitutes." *Expert Review of Medical Devices* 3 (1): 49-57.

Lian, Qin, Fei Yang, Hua Xin, and Dichen Li. 2017. "Oxygen-Controlled Bottom-up Mask-Projection Stereolithography for Ceramic 3D Printing." *Ceramics International* 43 (17): 14956-61.

Melchels, Ferry P. W., Jan Feijen, and Dirk W. Grijpma. 2009. "A Poly(D,L-Lactide) Resin for the Preparation of Tissue Engineering Scaffolds by Stereolithography." *Biomaterials* 30 (23-24): 3801-9.

Meyer, Ulrich. 2009. "The History of Tissue Engineering and Regenerative Medicine in Perspective." In *Fundamentals of Tissue Engineering and Regenerative Medicine,* 5-12. Springer, Berlin, Heidelberg.

Meyer, Ulrich, Hans Peter Wiesmann, Jörg Handschel, and Norbert R. Kübler. 2009. "Bone Tissue Engineering." In *Fundamentals of Tissue Engineering and Regenerative Medicine,* 211-32. Springer, Berlin, Heidelberg.

Mott, Eric J., Mallory Busso, Xinyi Luo, Courtney Dolder, Martha O. Wang, John P. Fisher, and David Dean. 2016. "Digital Micromirror Device (DMD)-Based 3D Printing of Poly(Propylene Fumarate) Scaffolds." *Materials Science & Engineering. C. Materials for Biological Applications* 61 (April): 301-11.

Nerem, Robert M., and Stacey C. Schutte. 2014. "Chapter 2—The Challenge of Imitating Nature." In *Principles of Tissue Engineering (Fourth Edition)*, 9-24. Boston: Academic Press.

Ng, Vincent Y. 2012. "Risk of Disease Transmission with Bone Allograft." *Orthopedics* 35 (8): 679-81.

Pan, Yayue, Haiyang He, Jie Xu, and Alan Feinerman. 2017. "Study of Separation Force in Constrained Surface Projection Stereolithography." *Rapid Prototyping Journal* 23 (2): 353-61.

Pangborn, Christine A., and Kyriacos A. Athanasiou. 2005. "Growth Factors and Fibrochondrocytes in Scaffolds." *Journal of Orthopaedic Research: Official Publication of the Orthopaedic Research Society* 23 (5): 1184-90.

Rodriguez, Ciro A., Hernan Lara-Padilla, and David Dean. 2018. "Bioceramics for Musculoskeletal Regenerative Medicine: Materials and Manufacturing Process Compatibility for Synthetic Bone Grafts and Medical Devices." In 3*D Printing and Biofabrication*, 1-33. Reference Series in Biomedical Engineering. Springer, Cham.

Rosser, J., and D. J. Thomas. 2018. "10-Bioreactor Processes for Maturation of 3D Bioprinted Tissue." In 3*D Bioprinting for Reconstructive Surgery*, 191-215. Woodhead Publishing.

Salgado, António J., Olga P. Coutinho, and Rui L. Reis. 2004. "Bone Tissue Engineering: State of the Art and Future Trends." *Macromolecular Bioscience* 4 (8): 743-65.

Schneider, Caroline A., Wayne S. Rasband, and Kevin W. Eliceiri. 2012. "NIH Image to ImageJ: 25 Years of Image Analysis." *Nature Methods* 9 (7): 671-75.

Sela, Jona J., and Itai A. Bab. 2012. "Healing of Bone Fracture: General Concepts." In *Principles of Bone Regeneration*, 1-8. Springer, Boston, MA.

Sipos, Wolfgang, Ursula Föger-Samwald, and Peter Pietschmann. 2014. "Supporting Apparatus of Vertebrates: Skeleton and Bones." In *Comparative Medicine*, 35-44. Springer, Vienna.

Sladkova, Martina, and Giuseppe Maria de Peppo. 2014. "Bioreactor Systems for Human Bone Tissue Engineering." *Processes* 2 (2): 494-525.

Sun, C., N. Fang, D. M. Wu, and X. Zhang. 2005. "Projection Micro-Stereolithography Using Digital Micro-Mirror Dynamic Mask." *Sensors and Actuators A: Physical* 121 (1): 113-20.

Taubin, G. 1995. "Curve and Surface Smoothing without Shrinkage." In *Proceedings of IEEE International Conference on Computer Vision*, 852-57.

Walker, Jason M., Emily Bodamer, Alex Kleinfehn, Yuanyuan Luo, Matthew Becker, and David Dean. 2017. "Design and Mechanical Characterization of Solid and Highly Porous 3D Printed Poly(Propylene Fumarate) Scaffolds." *Progress in Additive Manufacturing* 2 (1-2): 99-108.

Wendt, D., S. A. Riboldi, M. Cioffi, and I. Martin. 2009. "Bioreactors in Tissue Engineering: Scientific Challenges and Clinical Perspectives." *Advances in Biochemical Engineering/Biotechnology* 112:1-27.

Wu, Xiangquan, Qin Lian, Dichen Li, and Zhongmin Jin. 2017. "Tilting Separation Analysis of Bottom-up Mask Projection Stereolithography Based on Cohesive Zone Model." *Journal of Materials Processing Technology* 243 (May): 184-96.

Yeatts, Andrew B., and John P. Fisher. 2011. "Bone Tissue Engineering Bioreactors: Dynamic Culture and the Influence of Shear Stress." *Bone* 48 (2): 171-81.

Zhou, Chi, Yong Chen, Zhigang Yang, and Behrokh Khoshnevis. 2013. "Digital Material Fabrication Using Mask-image-projection-based Stereolithography." *Rapid Prototyping Journal* 19 (3): 153-65.

A number of embodiments of the disclosure have been described. Nevertheless, it will be understood that various modifications may be made without departing from the spirit and of the invention. Accordingly, other embodiments are within the scope of the following claims.

What is claimed is:

1. A method for optimizing a stereolithographic additive manufacturing process for the production of a three-dimensional object using a stereolithographic additive manufacturing device, the method comprising:
   (a) actuating a build plate to separate a test layer from the build plate;
   (b) measuring a separation force required to separate the test layer from the build plate with a force sensor during step (a);
   (c) repeating steps (a) and (b) to form one or more additional layers having one or more additional cross-sectional areas until there is a failure of interlayer binding of any two of the layers upon activation of the build plate;
   (d) calculating an interlayer green strength by dividing the separation force measured for a most recent additional layer manufactured during step (c) upon failure of interlayer binding by the additional cross-sectional area of the most recent additional layer; and
   (e) calculating a probability of structural failure of the test layer by comparing the separation force of the test layer with the interlayer green force;
   wherein if the separation force of the test layer is greater than the interlayer green force, then a resin composition is modified, a cross-sectional overlap between the test layer and one or more adjacent layers is increased, an incident energy generated by the stereolithographic additive manufacturing device during the stereolithographic additive manufacturing process is modified, or a combination thereof.

2. The method of claim 1, wherein the stereolithographic additive manufacturing process comprises a Vat photopolymerization.

3. The method of claim 1, wherein the stereolithographic additive manufacturing process comprises continuous digital light processing (cDLP).

4. The method of claim 1, wherein the stereolithographic additive manufacturing device comprises a digital micromirror device (DMD), a transparent or translucent basement plate, and the build plate operatively coupled to the force sensor.

5. The method of claim 1, wherein the resin composition comprises a liquid light-curable material and a photoinitiator.

6. The method of claim 5, wherein the liquid light-curable material comprises a polymer.

7. The method of claim 6, wherein the polymer comprises poly(propylene fumarate) (PPF).

8. The method of claim 6, wherein the polymer has a molecular weight of 4,000 Daltons or less.

9. The method of claim 1, wherein the resin composition comprises a first liquid light-curable material and a photoinitiator, and wherein modification of the resin composition comprises selecting a different liquid light-curable material.

10. The method of claim 9, wherein the different liquid light-curable material exhibits different rheological properties than the first liquid light-curable material.

11. The method of claim 1, wherein the resin composition comprises a liquid light-curable material, a photoinitiator, and a dye.

12. The method of claim 11, wherein modification of the resin composition comprises altering a ratio of the dye to the photoinitiator.

13. The method of claim 11, wherein the dye comprises 2-hydroxy-4-methoxybenzophenone.

14. The method of claim 5, wherein the photoinitiator is selected from the group consisting of bis(2,4,6-trimethylbenzoyl)phenylphosphine oxide (BAPO), bis[2,6-difluoro-3-(1-hydroxypyrrol-1-yl)phenyl]titanocene, or a combination thereof.

15. The method of claim 1, wherein the resin composition further comprises a solvent.

16. The method of claim 1, wherein the resin composition further comprises a reactive diluent.

17. The method of claim 16, wherein the reactive diluent is selected from the group consisting of N-vinyl pyrrolidone, diethyl fumarate (DEF), or a combination thereof.

18. The method of claim 1, wherein modification of the incident energy generated by the stereolithographic additive manufacturing device during the stereolithographic additive manufacturing process is selected from the group consisting of varying a wavelength of incident light, varying an intensity of incident light, varying a duration of incident light, or a combination thereof.

* * * * *